(12) United States Patent
Meng et al.

(10) Patent No.: US 11,370,842 B2
(45) Date of Patent: Jun. 28, 2022

(54) ANTI-IL1RAP ANTIBODIES

(71) Applicant: CITY OF HOPE, Duarte, CA (US)

(72) Inventors: Weixu Meng, San Diego, CA (US); Guido Marcucci, Azusa, CA (US)

(73) Assignee: CITY OF HOPE, Duarte, CA (US)

( * ) Notice: Subject to any disclaimer, the term of this patent is extended or adjusted under 35 U.S.C. 154(b) by 30 days.

(21) Appl. No.: 16/635,534

(22) PCT Filed: Aug. 1, 2018

(86) PCT No.: PCT/US2018/044890
§ 371 (c)(1),
(2) Date: Jan. 30, 2020

(87) PCT Pub. No.: WO2019/028190
PCT Pub. Date: Feb. 7, 2019

(65) Prior Publication Data
US 2020/0247893 A1  Aug. 6, 2020

Related U.S. Application Data

(60) Provisional application No. 62/539,895, filed on Aug. 1, 2017.

(51) Int. Cl.
*C07K 16/28* (2006.01)
*A61P 35/02* (2006.01)

(52) U.S. Cl.
CPC .......... *C07K 16/2866* (2013.01); *A61P 35/02* (2018.01); *C07K 16/2809* (2013.01); *C07K 2317/31* (2013.01); *C07K 2317/52* (2013.01); *C07K 2317/55* (2013.01); *C07K 2317/622* (2013.01); *C07K 2317/92* (2013.01); *C07K 2319/03* (2013.01); *C07K 2319/33* (2013.01)

(58) Field of Classification Search
CPC ............ C07K 16/2866; C07K 16/2809; C07K 2317/31; C07K 2317/52; C07K 2317/55; C07K 2317/622; C07K 2317/92; A61P 35/02
See application file for complete search history.

(56) References Cited

U.S. PATENT DOCUMENTS

| | | |
|---|---|---|
| 2012/0114665 A1 | 5/2012 | Martin et al. |
| 2012/0167237 A1 | 6/2012 | Bradley et al. |
| 2014/0017167 A1 | 1/2014 | Fioretos et al. |
| 2017/0121420 A1 | 5/2017 | Heidrich et al. |

FOREIGN PATENT DOCUMENTS

| | | |
|---|---|---|
| WO | WO-2015/132602 A1 | 9/2015 |
| WO | WO-2016/020502 A1 | 2/2016 |

OTHER PUBLICATIONS

Agerstam, H. et al. (Aug. 25, 2015, e-published Aug. 10, 2015). "Antibodies targeting human IL1RAP (IL1R3) show therapeutic effects in xenograft models of acute myeloid leukemia," *PNAS USA* 112(34):10786-10791.
Agerstam, H. et al. (Dec. 8, 2016, e-published Sep. 12, 2016). "IL1RAP antibodies block IL-1-induced expansion of candidate CML stem cells and mediate cell killing in xenograft models," *Blood* 128(23):2683-2693.
Askmyr, M. et al. (May 2, 2013, e-published Mar. 11, 2013). "Selective killing of candidate AML stem cells by antibody targeting of IL1RAP," *Blood* 121(18):3709-3713.
Berthon, C. et al. (Dec. 2010, e-published Sep. 4, 2010). "In acute myeloid leukemia, B7-H1 (PD-L1) protection of blasts from cytotoxic T cells is induced by TLR ligands and interferon-gamma and can be reversed using MEK inhibitors," *Cancer Immunol Immunother* 59(12):1839-1849.
Grupp, S.A. et al. (Apr. 18, 2013, e-published Mar. 25, 2013). "Chimeric antigen receptor-modified T cells for acute lymphoid leukemia," *N Engl J Med* 368(16):1509-1518.
International Search Report dated Oct. 16, 2018, for PCT Application No. PCT/US2018/044890, filed Aug. 1, 2018, 3 pages.
Jaras, M. et al. (Sep. 14, 2010, e-published Aug. 30, 2010). "Isolation and killing of candidate chronic myeloid leukemia stem cells by antibody targeting of IL-1 receptor accessory protein," *PNAS USA* 107(37):16280-16285.
Maus, M.V. et al. (Apr. 24, 2014, e-published Feb. 27, 2014). "Antibody-modified T cells: CARs take the front seat for hematologic malignancies," *Blood* 123(17):2625-2635.
Partial Supplementary European Search Report dated Apr. 8, 2021, for EP Patent Application No. 18842068.1, 16 pages.
Walter, R.B. (Jun. 2014, e-published Mar. 11, 2014). "Biting back: BiTE antibodies as a promising therapy for acute myeloid leukemia," *Expert Rev Hematol* 7(3):317-319.
Wang, Q-S. et al. (Jan. 2015, e-published Sep. 1, 2014). "Treatment of CD33-directed chimeric antigen receptor-modified T cells in one patient with relapsed and refractory acute myeloid leukemia," *Molecular Therapy* 23(1):184-191.
Written Opinion dated Oct. 16, 2018, for PCT Application No. PCT/US2018/044890, filed Aug. 1, 2018, 3 pages.

*Primary Examiner* — Brad Duffy
*Assistant Examiner* — Cheom-Gil Cheong
(74) *Attorney, Agent, or Firm* — Mintz, Levin, Cohn, Ferris, Glovsky and Popeo, P.C.

(57) ABSTRACT

Provided herein are, inter alia, antibodies capable of binding Interleukin-1 receptor accessory protein (IL1RAP). The antibodies provided herein include novel light chain and heavy chain sequences and bind IL1RAP with high efficiency and specificity. The anti-IL1RAP antibodies provided herein are, inter alia, useful for the treatment of IL1RAP-expressing cancers such as AML.

20 Claims, 45 Drawing Sheets
Specification includes a Sequence Listing.

SEQUENCE LISTING

```
<160> NUMBER OF SEQ ID NOS: 90

<210> SEQ ID NO 1
<211> LENGTH: 11
<212> TYPE: PRT
<213> ORGANISM: Artificial sequence
<220> FEATURE:
<223> OTHER INFORMATION: Synthetic polypeptide
```

<400> SEQUENCE: 1

Gln Ser Leu Leu His Ser Asn Gly Tyr Lys Tyr
1               5                   10

<210> SEQ ID NO 2
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 2

Leu Gly Ser
1

<210> SEQ ID NO 3
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 3

Met Gln Ala Leu Gln Thr Pro Leu Thr
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 4

Gly Tyr Ser Phe Ser Ser His Trp
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 5

Ile Tyr Pro Gly Asp Ser Asp Thr
1               5

<210> SEQ ID NO 6
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 6

Ala Arg Gly Glu Leu Pro Gly Glu Ala Tyr Tyr Phe Asp Asn
1               5                   10

<210> SEQ ID NO 7
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 7

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 8
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 8

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser His
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Glu Leu Pro Gly Glu Ala Tyr Tyr Phe Asp Asn Trp Gly
            100                 105                 110

Gln Gly Thr Leu Val Thr Val Ser Ser
        115                 120

<210> SEQ ID NO 9
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 9

Glu Ile Val Met Thr Gln Ser Pro Leu Ser Leu Pro Val Thr Pro Gly
1               5                   10                  15

Glu Pro Ala Ser Ile Ser Cys Arg Ser Ser
            20                  25

<210> SEQ ID NO 10
<211> LENGTH: 17
<212> TYPE: PRT
<213> ORGANISM: Artificial sequence
<220> FEATURE:

```
<223> OTHER INFORMATION: Synthetic polypeptide

<400> SEQUENCE: 10

Leu Asp Trp Tyr Leu Gln Lys Pro Gly Gln Ser Pro Gln Leu Leu Ile
1               5                   10                  15

Tyr

<210> SEQ ID NO 11
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 11

Asn Arg Ala Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 12
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 12

Phe Gly Gly Gly Thr Lys Val Glu Ile Lys
1               5                   10

<210> SEQ ID NO 13
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 13

Gln Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 14
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 14

Ile Gly Trp Val Arg Gln Met Pro Gly Lys Gly Leu Glu Trp Met Gly
1               5                   10                  15

Ile

<210> SEQ ID NO 15
<211> LENGTH: 38
<212> TYPE: PRT
<213> ORGANISM: Artificial sequence
<220> FEATURE:
<223> OTHER INFORMATION: Synthetic polypeptide
```

<400> SEQUENCE: 15

Arg Tyr Ser Pro Ser Phe Gln Gly Gln Val Thr Ile Ser Ala Asp Lys
1               5                   10                  15

Ser Ile Ser Thr Ala Tyr Leu Gln Trp Ser Ser Leu Lys Ala Ser Asp
            20                  25                  30

Thr Ala Met Tyr Tyr Cys
        35

<210> SEQ ID NO 16
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 16

Trp Gly Gln Gly Thr Leu Val Thr Val Ser Ser
1               5                   10

<210> SEQ ID NO 17
<211> LENGTH: 248
<212> TYPE: PRT
<213> ORGANISM: Artificial sequence
<220> FEATURE:
<223> OTHER INFORMATION: Synthetic polypeptide

<400> SEQUENCE: 17

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser His
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Glu Leu Pro Gly Glu Ala Tyr Tyr Phe Asp Asn Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Glu Ile Val Met Thr Gln Ser Pro
    130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Lys Tyr Leu Asp Trp
                165                 170                 175

Tyr Leu Gln Lys Pro Gly Gln Ser Pro Gln Leu Leu Ile Tyr Leu Gly
            180                 185                 190

Ser Asn Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Val
    210                 215                 220

Gly Val Tyr Tyr Cys Met Gln Ala Leu Gln Thr Pro Leu Thr Phe Gly
225                 230                 235                 240

Gly Gly Thr Lys Val Glu Ile Lys
            245

<210> SEQ ID NO 18
<211> LENGTH: 744
<212> TYPE: DNA
<213> ORGANISM: Artificial sequence
<220> FEATURE:
<223> OTHER INFORMATION: Synthetic polynucleotide

<400> SEQUENCE: 18
caggtgcagc tggtgcagag cggcgccgaa gtgaagaagc ccggcgagag cctgaagatc      60
agctgcaagg gcagcggcta cagcttcagc agccactgga tcggctgggt caggcagatg     120
cccggcaaag gcctggagtg gatgggcatc atctatcccg gcgacagcga caccaggtac     180
tcccccagct tccagggcca ggtgaccatc tccgccgaca gagcattgg caccgcctac     240 ctgcagtgga gcagcctcaa agccagcgac accgccatgt actactgcgc cagaggcgaa     300
ctgccccgga aggcctacta cttcgataac tggggccagg gcaccctggt gacagtgagc     360
agcggaggag cggcagcgg cggcggcgga tccggaggag cggctccga tcgtgatg        420 acccagagcc ctctgagcct gcccgtgaca cctggcgaaa ctgccagcat cagctgcaga     480
agcagccaga gcctgctcca ctccaacggc tacaaatacc tggactggta tctccagaag     540
cctggccaga gccccagct gctcatctac ctgggcagca ataggccag cggagtgccc     600 gacaggttta gcggctccgg aagcggcacc gatttcaccc tgaaaatcag cagagtggag     660
gccgaggacg tgggcgtgta ctactgcatg caggctctgc agacacccct gaccttcggc     720
ggaggcacca aggtggagat caag                                            744

<210> SEQ ID NO 19
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 481
<212> TYPE: PRT
<213> ORGANISM: Artificial sequence
<220> FEATURE:
<223> OTHER INFORMATION: Synthetic polypeptide

<400> SEQUENCE: 20

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser His
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85              90                  95

Ala Arg Gly Glu Leu Pro Gly Glu Ala Tyr Tyr Phe Asp Asn Trp Gly
                100                 105                 110

Gln Gly Thr Leu Val Thr Val Ser Ser Gly Gly Gly Ser Gly Gly
                115                 120                 125

Gly Gly Ser Gly Gly Gly Ser Glu Ile Val Met Thr Gln Ser Pro
    130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Lys Tyr Leu Asp Trp
                165                 170                 175

Tyr Leu Gln Lys Pro Gly Gln Ser Pro Gln Leu Leu Ile Tyr Leu Gly
                180                 185                 190

Ser Asn Arg Ala Ser Gly Val Pro Asp Arg Phe Ser Gly Ser Gly Ser
                195                 200                 205

Gly Thr Asp Phe Thr Leu Lys Ile Ser Arg Val Glu Ala Glu Asp Val
    210                 215                 220

Gly Val Tyr Tyr Cys Met Gln Ala Leu Gln Thr Pro Leu Thr Phe Gly
225                 230                 235                 240

Gly Gly Thr Lys Val Glu Ile Lys Cys Ala Pro Lys Ser Cys Asp Lys
                245                 250                 255

Thr His Thr Cys Pro Pro Cys Pro Ala Pro Glu Ala Ala Gly Gly Pro
                260                 265                 270

Ser Val Phe Leu Phe Pro Pro Lys Pro Lys Asp Thr Leu Met Ile Ser
                275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
                340                 345                 350

Tyr Lys Cys Lys Val Ser Asn Lys Ala Leu Pro Ala Pro Ile Glu Lys
                355                 360                 365

Thr Ile Ser Lys Ala Lys Gly Gln Pro Arg Glu Pro Gln Val Tyr Thr
                370                 375                 380

Leu Pro Pro Ser Arg Glu Glu Met Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
                420                 425                 430

Asp Ser Asp Gly Ser Phe Phe Leu Val Ser Lys Leu Thr Val Asp Lys
                435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 21
<211> LENGTH: 482
<212> TYPE: PRT
<213> ORGANISM: Artificial sequence
<220> FEATURE:
<223> OTHER INFORMATION: Synthetic polypeptide

<400> SEQUENCE: 21

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Cys Ala Pro Lys Ser Cys Asp
                245                 250                 255

Lys Thr His Thr Cys Pro Pro Cys Pro Ala Pro Glu Ala Ala Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365
```

```
Lys Thr Ile Ser Lys Ala Lys Gly Gln Pro Arg Glu Pro Gln Val Tyr
        370                 375                 380

Thr Leu Pro Pro Ser Arg Glu Glu Met Thr Lys Asn Gln Val Ser Leu
385                 390                 395                 400

Trp Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 22
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 22

Ala Arg Asp Glu Ser His Ser Thr Ile Thr Pro Arg His
1               5                   10

<210> SEQ ID NO 23
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 23

Ala Arg Val Gly Pro His Tyr Ser Asp Ser Ser Gly Tyr Tyr Tyr Ile
1               5                   10                  15

Asp Asp Asn Ser Tyr Asp Met Asp Val
            20                  25

<210> SEQ ID NO 24
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 24

Ala Arg Asp Val Trp Val Val Pro Ala Ala Pro Leu Tyr Tyr Tyr Tyr
1               5                   10                  15

Gly Met Asp Val
            20

<210> SEQ ID NO 25
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 25

Ala Arg Asp Gly Asp Tyr Gly Val Trp Trp Phe Asp Pro
1               5                   10

<210> SEQ ID NO 26
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 26

Ala Arg Gly Arg Leu Ala Ser Gly Ser Trp Asn Gly Phe Asp Ile
1               5                   10                  15

<210> SEQ ID NO 27
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 27

Ala Ala Glu Ser Gly Arg Pro Gly Phe Gly Ser Tyr Trp Gly Val Phe
1               5                   10                  15

Tyr Tyr Asn His Ala Met Asp Val
            20

<210> SEQ ID NO 28
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 28

Ala Arg Asp Gly Asn Val Pro Met Ala Ser Asp Phe Tyr Gly Met Asp
1               5                   10                  15

Leu

<210> SEQ ID NO 29
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 29

Ala Arg Gly Lys Gly Asp Ser Tyr Ala Phe Asp Ile
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 30

Ala Lys Gly His Tyr Tyr Tyr Tyr Gly Met Asp Val
1               5                   10

<210> SEQ ID NO 31
<211> LENGTH: 13
```

```
<212> TYPE: PRT
<213> ORGANISM: Artificial sequence
<220> FEATURE:
<223> OTHER INFORMATION: Synthetic polypeptide

<400> SEQUENCE: 31

Ala Arg Ala Gly Ser Gly Trp Tyr Gly Tyr Phe Asp Ser
1               5                   10

<210> SEQ ID NO 32
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 32

Ala Arg Asp Ser Glu Arg Val Val Ser Gly Trp Tyr Val Tyr Tyr Tyr
1               5                   10                  15

Tyr Tyr Tyr Met Asp Val
            20

<210> SEQ ID NO 33
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 33

Ala Lys Asp Leu Arg Gly Tyr Ser Tyr Gly Asn Tyr Asn Arg Asp Ala
1               5                   10                  15

Phe Asp Ile

<210> SEQ ID NO 34
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 34

Ala Arg Gly Lys Gly Asp Tyr Leu Tyr Tyr Gly Met Asp Val
1               5                   10

<210> SEQ ID NO 35
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 35

Ala Arg Pro Glu Gly Gly Ser Ser Leu Val Gly Gly Phe Asp Tyr
1               5                   10                  15

<210> SEQ ID NO 36
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 36

Ala Arg Phe Gly Gly Ala Thr Phe Asp Gly Pro Phe Asp Ile
1               5                   10
```

```
<210> SEQ ID NO 37
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 37

Ala Arg Arg Asp Thr Ala Met Glu Asn Phe Asp Tyr
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 38

Ala Arg Leu Tyr Tyr Asp Phe Trp Ser Gly Ser Ala
1               5                   10

<210> SEQ ID NO 39
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 39

Ala Arg Arg Ser Pro Asp Cys Ser Leu Thr Thr Cys Leu Pro Leu His
1               5                   10                  15

<210> SEQ ID NO 40
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 40

Val Arg Asp Val Ser Pro Gly Gly Ala Asp Val
1               5                   10

<210> SEQ ID NO 41
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 41

Ala Lys Gly Gly Thr Leu Asp Ala Phe Gly Ile
1               5                   10

<210> SEQ ID NO 42
<211> LENGTH: 23
<212> TYPE: PRT
<213> ORGANISM: Artificial sequence
<220> FEATURE:
<223> OTHER INFORMATION: Synthetic polypeptide

<400> SEQUENCE: 42

Ala Arg Ala Phe Asn Arg Tyr Cys Ser Gly Gly Ser Cys Tyr Pro Pro
1               5                   10                  15
```

Gly Arg Tyr Gly Met Asp Val
            20

<210> SEQ ID NO 43
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 43

Ala Arg Asp His Glu Ser Arg Ser Pro Gly Asp Tyr His Met Asp Val
1               5                   10                  15

<210> SEQ ID NO 44
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 44

Ala Ser Leu Asp Leu Thr Ala Ala Arg Ser Val Ile Ala Ala Phe Asp
1               5                   10                  15

Ile

<210> SEQ ID NO 45
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 45

Ala Arg Gly Asp Ser Ser Asp Tyr Trp Thr Ser Thr Asp Ala Phe Asp
1               5                   10                  15

Ile

<210> SEQ ID NO 46
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 46

Ala Ile Pro Tyr Gly Asp Tyr Pro Pro Ala Phe Ala Val
1               5                   10

<210> SEQ ID NO 47
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 47

Ala Arg Asp Ser Pro Glu Gly Ala Phe Asp Ile
1               5                   10

<210> SEQ ID NO 48
<211> LENGTH: 15
<212> TYPE: PRT
<213> ORGANISM: Artificial sequence
<220> FEATURE:
<223> OTHER INFORMATION: Synthetic polypeptide

```
<400> SEQUENCE: 48

Ala Arg Phe Asn Cys Tyr Ser Ser Gly Cys Pro Leu Met Asp Tyr
1               5                   10                  15

<210> SEQ ID NO 49
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 49

Ala Arg Asp Ser Gly Ser Tyr Leu Phe Asp Tyr
1               5                   10

<210> SEQ ID NO 50
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 50

Ala Arg Thr Leu Pro Tyr Asp Phe Trp Ser Gly Tyr Ser Ala Tyr Tyr
1               5                   10                  15

Tyr Tyr Tyr Tyr Tyr Met Asp Val
            20

<210> SEQ ID NO 51
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 51

Ala Arg Glu Asp Gly His Thr Gly Ile Tyr Asp Tyr
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 52

Ala Arg Gly Ala Glu Tyr Ser Ser Ser Ser Pro Asp Tyr
1               5                   10

<210> SEQ ID NO 53
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 53

Ala Arg Gln Gly Asn Ile Val Val Val Ala Asn Asp Ala Phe Asp
1               5                   10                  15

Ile

<210> SEQ ID NO 54
<211> LENGTH: 30
```

<212> TYPE: PRT
<213> ORGANISM: Artificial sequence
<220> FEATURE:
<223> OTHER INFORMATION: Synthetic polypeptide

<400> SEQUENCE: 54

Ala Lys Glu Val Arg Pro Gly His Cys Ser Gly Gly Ser Gly Gly Ser
1               5                   10                  15

Cys Tyr Ser Val Pro Gly Arg Asp Tyr Tyr Gly Met Asp Val
            20                  25                  30

<210> SEQ ID NO 55
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 55

Ala Gly Pro Ser Gly Pro Ala Lys Lys Asp Ala Phe Asp Ile
1               5                   10

<210> SEQ ID NO 56
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 56

Gln Cys Gly Ile Val Val Val Ile Ile Phe Met
1               5                   10

<210> SEQ ID NO 57
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 57

Leu Gln His Arg Ser Gly Tyr Leu
1               5

<210> SEQ ID NO 58
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 58

Met Gln Gly Ile His Leu Pro Arg Tyr Thr
1               5                   10

<210> SEQ ID NO 59
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 59

Gln Gln Tyr Tyr Ser Ser Pro Leu Thr
1               5

```
<210> SEQ ID NO 60
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 60

Gln Gln Tyr Tyr Ser Met Val Ser Leu Thr
1               5                   10

<210> SEQ ID NO 61
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 61

Leu Val Trp His Asn Arg Ala Trp Val
1               5

<210> SEQ ID NO 62
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 62

Gln Gln Tyr Asp Asn Leu Leu Leu Thr
1               5

<210> SEQ ID NO 63
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 63

Gln Ala Trp Asp Asn Thr Ser Gln Tyr Val
1               5                   10

<210> SEQ ID NO 64
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 64

Gln Gln Ser Tyr Thr Val Pro Tyr Thr
1               5

<210> SEQ ID NO 65
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 65

Gln Lys Tyr Asn Ser Ala Pro Tyr Thr
1               5

<210> SEQ ID NO 66
```

```
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 66

Gln Val Trp Asp Arg Ser Gly Asp His Gln Gly Val
1               5                   10

<210> SEQ ID NO 67
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 67

Gln Ser Tyr Asp Ser Ser Leu Ser Gly Ser Gly Val Val
1               5                   10

<210> SEQ ID NO 68
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 68

Gln Tyr Tyr Asn Thr Tyr Ser Pro Trp Thr
1               5                   10

<210> SEQ ID NO 69
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 69

Ala Val Trp Asp Asp Ser Leu Lys Gly Val Val
1               5                   10

<210> SEQ ID NO 70
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 70

Leu Gln His Asn Thr Tyr Pro Trp Thr
1               5

<210> SEQ ID NO 71
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 71

Gln Gln Arg Ser Asn Trp Pro Glu Leu Thr
1               5                   10

<210> SEQ ID NO 72
<211> LENGTH: 9
```

```
<212> TYPE: PRT
<213> ORGANISM: Artificial sequence
<220> FEATURE:
<223> OTHER INFORMATION: Synthetic polypeptide

<400> SEQUENCE: 72

Met Gln Ala Leu Gln Thr Pro Trp Thr
1               5

<210> SEQ ID NO 73
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 73

Gln Gln Tyr Ala Asp Ser Pro Leu Thr
1               5

<210> SEQ ID NO 74
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 74

Gln Gln Tyr Gly Arg Ser Pro Pro Phe Ala
1               5                   10

<210> SEQ ID NO 75
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 75

Gln Gln Ser His Ser Ser Ser Arg
1               5

<210> SEQ ID NO 76
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 76

Cys Ser Tyr Ala Gly Ala Tyr Thr Glu Ile
1               5                   10

<210> SEQ ID NO 77
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 77

His Gln Tyr Gly Ser Ile Pro His Thr
1               5

<210> SEQ ID NO 78
<211> LENGTH: 13
<212> TYPE: PRT
```

```
<213> ORGANISM: Artificial sequence
<220> FEATURE:
<223> OTHER INFORMATION: Synthetic polypeptide

<400> SEQUENCE: 78

Gly Ala Asp His Gly Ser Gly Ser Asn Phe Leu Tyr Val
1               5                   10

<210> SEQ ID NO 79
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 79

Gln Val Trp Asp Ser Gly Ser Asp Gln Gly Val
1               5                   10

<210> SEQ ID NO 80
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 80

Gln Gln Tyr His Thr Ile Pro Tyr Ser
1               5

<210> SEQ ID NO 81
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 81

Gln Gln Tyr Gly Ser Ser Pro Arg Thr
1               5

<210> SEQ ID NO 82
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 82

Leu Gln Tyr Gly Arg Ser Pro Phe Thr
1               5

<210> SEQ ID NO 83
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 83

Cys Ser Met Gly Cys His Pro Lys Cys Leu Trp Ala
1               5                   10

<210> SEQ ID NO 84
<211> LENGTH: 9
<212> TYPE: PRT
<213> ORGANISM: Artificial sequence
```

```
<220> FEATURE:
<223> OTHER INFORMATION: Synthetic polypeptide

<400> SEQUENCE: 84

Met Gln Gly Leu Gln Thr Pro Ile Gly
1               5

<210> SEQ ID NO 85
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 85

Cys Ser Tyr Val Gly Arg Tyr Thr Tyr Val
1               5                   10

<210> SEQ ID NO 86
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 86

Gln Gln Tyr Asn Thr Tyr Pro Arg Ala
1               5

<210> SEQ ID NO 87
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 87

Gln His Tyr Gly Ser Ser Leu Trp Pro
1               5

<210> SEQ ID NO 88
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 88

Met Gln Ala Leu Gln Thr Pro Val Thr
1               5

<210> SEQ ID NO 89
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 89

Gln Arg Tyr Asn Asn Trp Pro Pro Gly Ile Thr
1               5                   10

<210> SEQ ID NO 90
<211> LENGTH: 517
<212> TYPE: PRT
<213> ORGANISM: Artificial sequence
<220> FEATURE:
```

<223> OTHER INFORMATION: Synthetic polypeptide

<400> SEQUENCE: 90

```
Met Leu Leu Leu Val Thr Ser Leu Leu Leu Cys Glu Leu Pro His Pro
1               5                   10                  15
Ala Phe Leu Leu Ile Pro Gln Val Gln Leu Val Gln Ser Gly Ala Glu
            20                  25                  30
Val Lys Lys Pro Gly Glu Ser Leu Lys Ile Ser Cys Lys Gly Ser Gly
        35                  40                  45
Tyr Ser Phe Ser Ser His Trp Ile Gly Trp Val Arg Gln Met Pro Gly
    50                  55                  60
Lys Gly Leu Glu Trp Met Gly Ile Ile Tyr Pro Gly Asp Ser Asp Thr
65                  70                  75                  80
Arg Tyr Ser Pro Ser Phe Gln Gly Gln Val Thr Ile Ser Ala Asp Lys
                85                  90                  95
Ser Ile Ser Thr Ala Tyr Leu Gln Trp Ser Ser Leu Lys Ala Ser Asp
            100                 105                 110
Thr Ala Met Tyr Tyr Cys Ala Arg Gly Glu Leu Pro Gly Glu Ala Tyr
        115                 120                 125
Tyr Phe Asp Asn Trp Gly Gln Gly Thr Leu Val Thr Val Ser Ser Gly
    130                 135                 140
Gly Gly Gly Ser Gly Gly Gly Ser Gly Gly Gly Ser Glu Ile
145                 150                 155                 160
Val Met Thr Gln Ser Pro Leu Ser Leu Pro Val Thr Pro Gly Glu Pro
                165                 170                 175
Ala Ser Ile Ser Cys Arg Ser Ser Gln Ser Leu Leu His Ser Asn Gly
            180                 185                 190
Tyr Lys Tyr Leu Asp Trp Tyr Leu Gln Lys Pro Gly Gln Ser Pro Gln
        195                 200                 205
Leu Leu Ile Tyr Leu Gly Ser Asn Arg Ala Ser Gly Val Pro Asp Arg
    210                 215                 220
Phe Ser Gly Ser Gly Ser Gly Thr Asp Phe Thr Leu Lys Ile Ser Arg
225                 230                 235                 240
Val Glu Ala Glu Asp Val Gly Val Tyr Tyr Cys Met Gln Ala Leu Gln
                245                 250                 255
Thr Pro Leu Thr Phe Gly Gly Gly Thr Lys Val Glu Ile Lys Val Ala
            260                 265                 270
Ala Ala Ala Phe Val Pro Val Phe Leu Pro Ala Lys Pro Thr Thr Thr
        275                 280                 285
Pro Ala Pro Arg Pro Pro Thr Pro Ala Pro Thr Ile Ala Ser Gln Pro
    290                 295                 300
Leu Ser Leu Arg Pro Glu Ala Cys Arg Pro Ala Ala Gly Gly Ala Val
305                 310                 315                 320
His Thr Arg Gly Leu Asp Phe Ala Cys Asp Ile Tyr Ile Trp Ala Pro
                325                 330                 335
Leu Ala Gly Thr Cys Gly Val Leu Leu Leu Ser Leu Val Ile Thr Leu
            340                 345                 350
Tyr Cys Asn His Arg Asn Arg Phe Ser Val Val Lys Arg Gly Arg Lys
        355                 360                 365
Lys Leu Leu Tyr Ile Phe Lys Gln Pro Phe Met Arg Pro Val Gln Thr
    370                 375                 380
Thr Gln Glu Glu Asp Gly Cys Ser Cys Arg Phe Pro Glu Glu Glu Glu
385                 390                 395                 400
```

-continued

```
Gly Gly Cys Glu Leu Arg Val Lys Phe Ser Arg Ser Ala Asp Ala Pro
            405                 410                 415

Ala Tyr Gln Gln Gly Gln Asn Gln Leu Tyr Asn Glu Leu Asn Leu Gly
            420                 425                 430

Arg Arg Glu Glu Tyr Asp Val Leu Asp Lys Arg Arg Gly Arg Asp Pro
            435                 440                 445

Glu Met Gly Gly Lys Pro Arg Arg Lys Asn Pro Gln Glu Gly Leu Tyr
        450                 455                 460

Asn Glu Leu Gln Lys Asp Lys Met Ala Glu Ala Tyr Ser Glu Ile Gly
465                 470                 475                 480

Met Lys Gly Glu Arg Arg Arg Gly Lys Gly His Asp Gly Leu Tyr Gln
            485                 490                 495

Gly Leu Ser Thr Ala Thr Lys Asp Thr Tyr Asp Ala Leu His Met Gln
            500                 505                 510

Ala Leu Pro Pro Arg
            515
```

ANTI-IL1RAP ANTIBODIES

CROSS REFERENCE TO RELATED APPLICATIONS

This application is a national stage entry under 35 U.S.C. 371 of International Application No. PCT/US2018/044890, filed Aug. 1, 2018, which claims priority to U.S. Provisional Application No. 62/539,895, filed Aug. 1, 2017, which is hereby incorporated by reference in their entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-667N01US_ST25.TXT, created Oct. 28, 2021, 38,297 bytes, machine format IBM-PC, MS Windows operating system, is hereby incorporated by reference.

BACKGROUND OF THE INVENTION

Acute myeloid leukemia (AML) is a devastating hematopoietic malignancy that can lead to hematopoiesis failure and death. Despite increasing knowledge of the disease, current treatment options benefit only a minority of AML patients. The limited success of treatments is believed to be at least partially due to the inability of chemotherapy and/or other molecular targeting therapeutics to eliminate so-called leukemia stem cells (LSCs). Thus, there is a need in the art for treatments which specifically eliminate LSCs while sparing normal hematopoietic stem cells.

Immunotherapeutic approaches hold promise as an effective means of treating patients suffering from AML. In order to be successful, however, immunotherapy must allow for the selective targeting and destruction of LSCs. Provided herein are compositions and methods which cure this and other needs in the art.

BRIEF SUMMARY OF THE INVENTION

In an aspect is provided an anti-interleukin-1 receptor accessory protein (IL1RAP) antibody including 3 a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

In an aspect, an isolated nucleic acid encoding an antibody as provided herein, including embodiments thereof, is provided.

In an aspect is provided a pharmaceutical composition including a therapeutically effective amount of an antibody as provided herein, including embodiments thereof, and a pharmaceutically acceptable excipient.

In an aspect is provided a method of treating cancer in a subject in need thereof, the method including administering to a subject a therapeutically effective amount of an antibody as provided herein, including embodiments thereof, thereby treating cancer in the subject.

In an aspect is provided a recombinant protein including: (i) an antibody region including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6; and (ii) a transmembrane domain.

In another aspect is provided a recombinant protein including: (i) a first antibody region capable of binding an effector cell ligand; and (ii) a second antibody region, including: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6.

In an aspect, an isolated nucleic acid encoding a recombinant protein as provided herein, including embodiments thereof, is provided.

In an aspect is provided a pharmaceutical composition including a therapeutically effective amount of a recombinant protein as provided herein, including embodiments thereof, and a pharmaceutically acceptable excipient.

In an aspect is provided a method of treating cancer in a subject in need thereof, the method including administering to a subject a therapeutically effective amount of a recombinant protein as described herein, including embodiments thereof, thereby treating cancer in the subject.

In an aspect is provided a method of inhibiting proliferation of a cell, the method including: (i) contacting a cell with an anti-IL1RAP antibody as provided herein including embodiments thereof, or a recombinant protein as provided herein including embodiments thereof, thereby forming a contacted cell; and (ii) allowing the anti-IL1RAP antibody, the recombinant protein as provided herein including embodiments thereof to bind an IL1RAP on the contacted cell, thereby inhibiting proliferation of the cell.

BRIEF DESCRIPTION OF THE DRAWINGS

FIG. 1A: Human antibody phage display library was constructed using peripheral blood mononuclear cells (PBMC) from 10 healthy donors. cDNA synthesized from RNA of purified B cells was used as a template for antibody heavy chain (VH) and light chain (VL) variable region amplification and fused with a linker (Gly4Ser)$_3$. The mixture of all scFvs were digested with restriction enzyme and ligated with the linearize phagemid vector. After electrotransformation, the TG1 bacteria were collected and glycerol stocks were made to store the library at −80° C. Library's quality was determined by its diversity (FIGS. 1B-1C) and capacity. The library capacity was $9.72 \times 10^9$ colonies. FIG. 1B: CDR3 length of both heavy chain (left) and light chain (right) from 50 randomly selected clones were analyzed.

FIG. 1C: Coverage of different heavy chain (top) and light chain (bottom) subfamily of the phage display library were analyzed based on the sequencing results of 50 clones. The distribution of CDR3 length and VH family was consistent with previously reported results from antibody repertoire next generation sequencing. FIG. 1D: Biopanning for IL1RAP antibodies using recombinant human IL1RAP protein. Enrichment was observed at the fourth round. See also Table 2 which corresponds to FIG. 1D.

FIG. 2A: Binding of 12 positive clones to recombinant IL1RAP protein. 1 µg/ml recombinant IL1RAP protein is coated to the 96-well plate at 4 degree overnight. Purified antibodies in three-fold serial dilution starting from 1 µg/ml are added to each well. HRP-anti-human FC antibody is used as detection antibody. FIG. 2B: $EC_{50}$ of 12 positive clones is calculated based on the ELISA binding curve. FIG. 2C: Antibody Dependent Cellular Cytotoxicity (ADCC) detected by $Cr^{51}$ release assay. Antibodies at 100 ng/ml are added to $1 \times 10^4$ $Cr^{51}$ labeled MV4-11 cells. $2 \times 10^5$ NK cells are used as effector cells. The specific lysis percentage is detected at 10 hours after incubation. FIG. 2D: Affinity of 1D5 detected by BiacoreT100. Combining the ELISA and ADCC results, Applicants selected 1D5 as the elite clone for bispecific antibody and CAR-T development. Applicants then used Biacore T100 to check its accurate KD. The KD of 1D5 was 21.2 nM.

FIG. 3A: Schematic representation of anti-CD3XIL1RAP bispecific antibody design. The bispecific antibody was assembled as scFv-FC. To facilitate heterodimer formation, the Knobs-into-Holes construct is applied to Applicants' bispecific antibody. The FC "knobs-into-holes" constructs were designed based on the IgG-FC backbone as using a site-directed mutagenesis kit (Invitrogen, Carlsbad, Calif.). For the FC-knob construct, one mutation was introduced in the CH3 domain (T366W, designated as knob) of one IgG-FC backbone. For the FC-hole construct, three mutations were introduced into the CH3 domain (T366S, L368A, and Y407V, designated as hole) of another IgG-FC backbone. To circumvent light chain and heavy chain mispairing, Applicants constructed a single chain variable fragment (scFv), linking the heavy and light chains of the same antibody by a $(Gly3Ser)_4$ linker. The scFv fragments of anti-CD3 antibody and anti-IL1RAP protein antibody were then cloned into the IgG-FC-knob and IgG-FC-hole vector, respectively. To further abolish the non-specific binding to AML cells by the FCγR, Applicants introduced double mutation (L234A, L235A) in the CH2 region. FIG. 3B: Expression of mono-specific and bispecific antibodies. SDS-PAGE gel result for purified proteins showed that anti-CD3-Knob-FC, anti-IL1RAP-Hole-FC, and anti-CD3xIL1RAP antibodies were all expressed. Lanes 1 to 3 are non-reduced protein: anti-CD3 knob antibody, anti-IL1RAP hole antibody, anti-CD3XIL1RAP bispecific antibody. Lanes 4 to 6 are reduced protein. Lane 7 is non-reduced bispecific antibody and lane 8 is reduced bispecific antibody. As shown in FIG. 3B, the size of bispecific antibody (Lane 3) is between two mono-specific antibodies. FIG. 3C: Dual binding of anti-CD3XIL1RAP antibody to T cell and IL1RAP protein was detected by flow cytometry. Bispecific antibody was incubated with T cells, recombinant IL1RAP protein with his tag was then added after it. FITC-anti-his antibody was used to detect the binding of IL1RAP protein to the bispecific antibody.

FIG. 4A: Genomic Mean Fluorescence Intensity (MFI) of IL1RAP expression in different AML cell lines, Raji is used as negative control. Except for KG1a, whose genomic medium fluorescence intensity (MFI) was slightly higher than Raji, MFI of the other six cell lines show significantly higher IL1RAP expression than Raji. FIG. 4B: Antibody copies bound per cell were compared in different AML cell lines. Based on the results shown in FIG. 4A and FIG. 4B, Applicants decided to use HL60, MV4-11, THP1, and KG1a, as a spectrum of cell lines with high to low levels of IL1RAP, and Raji as negative control for functional assays. FIG. 4C: T cell dependent cellular cytotoxicity (TDCC) was tested with the incubation of effector T cells and target AML cells at an E:T (Effector: Target cell ratio) ratio of 3:1, the specific lysis percentage was checked at 48 hours after incubation. The specific lysis was determined by flow cytometry, calculated using the formula: % Specific lyses= (Target cells$^{+T\ cells}$−Target cells$^{+BsAb+T\ cells}$)/Target cells$^{+T\ cells}$)×100%. T cell activation is checked by quantification of cytokines TNF-α (FIG. 4D), IFN-r (FIG. 4E), Granzyme B (FIG. 4F), and cell membrane markers CD69 (FIG. 4G) and CD25 (FIG. 4H). FIG. 4I: Different E:T ratios tested in the long term killing assay.

FIG. 5A: Three representative IL1RAP expression level of AML patient sample. FIG. 5B: Genomic Mean Fluorescence Intensity (MFI) of IL1RAP expression in different AML patient samples, PBMC was used as normal control. Compared to PBMC from healthy donor, all AML patient samples showed enhanced IL1RAP expression, shown by significantly higher MFI. FIG. 5C: T cell cytotoxicity is checked by a 48 hour long term killing assay at an E:T ratio of 5:1. FIG. 5D. T cell dependent cellular cytotoxicity assay (TDCC) with triplicates. CD34+ cells showed comparable IL1RAP expression compared to the bulky leukemia cells. TDCC indicated 90% of specific killing in most samples, and 60% in sample 667, which has the lowest IL1RAP expression levels. No difference was observed between sorted CD34$^+$ and unsorted AML blasts.

FIG. 6A: Tumor growth was monitored by bioluminescence imaging. $1 \times 10^6$ MV4-11 cells were injected to each mouse via tail vein. Treatment started on day 7 with 200 ug bispecific antibody and $3 \times 10^6$ T cell per mouse. The subsequent treatment and imaging time are indicated by the arrows below. Massive infiltration of leukemia was seen in the NSG mice transplanted with MV4-11$^{Luci}$ cells treated with vehicle, T cells only, or control BsAb plus T cells. Instead, massive reduction of leukemia burden was seen in the mice treated with T cells and anti-IL1RAPxCD3 BsAb at day 20, after one dose of treatment, and elimination at day 37, except for one mouse. One of the mice in this group died of improper procedure on day 18 at the 4$^{th}$ treatment. FIG. 6B: Survival curve. Three out of 4 mice were still alive on day 40, versus none of the mice in the other three groups survived. Notably, mice treated with T cells or T cells and isotype control had also a shorter survival than the control mice, probably due to the toxicity of T cells. Applicants also observed that the mice treated with BsAb were losing weight, likely due to the cytokine release.

FIG. 7A: Schematic diagram of the CAR containing a modified immunoglobulin G4 hinge, a modified transmembrane and intracellular signaling domain of CD28, and the CD3z signaling domain. The T2A ribosomal skip sequence and the EGFRt transduction marker were also indicated. 293T cells were transfected with pRSV-Rev, pMDLg/pRRE, pMD2.G and pELNS CAR plasmids and supernatants were collected at 24 hours and 48 hours and combined and concentrated using high-speed ultracentrifugation. Lentivirus titer was measured with HT-78 cells and stored at −80° C. until use.

FIG. 7B: Jurkat cells were transduced with either IL1RAP CAR or mock CAR. CD69 was detected for Jurkat cells cocultured with HL60, THP1, or KG1a cells which represent different IL1RAP expression levels separately. Raji cells were used as negative control. CD69 was detected for the activation of IL1RAP-CAR cells. The activation of IL1RAP-CAR-Jurkat cells was observed when cocultured with IL1RAP expressing target cells, while the mock-CAR-Jurkat cells remained at rest. IL1RAP-CAR-Jurkat cells stayed inactive as mock-CAR-Jurkat cells when cocultured with Raji cells or alone.

FIG. 8D: specific antigen-binding capacity (SABC) per cell as determined by flow cytometry in different AML cell lines. FIG. 8E: fold change of IL1RAP mean fluorescence intensity was compared between AML bulk cells (n=25), CD34+ enriched AML cells (n=18), and CD34+ enriched normal bone marrow cells (n=4). FIG. 8F: the percentage of IL1RAP+, CD123+, CLL-1+ and CD33+ in CD34+ enriched AML cells (n=9) were depicted with a symbol. FIG. 8G: fold change of mean fluorescence intensity on CD34+ enriched normal bone marrow cells (n=5) was compared for IL1RAP, CD123, CLL-1 and CD33. FIG. 8H: the percentage of IL1RAP+, CD123+, CLL-1+ and CD33+ in CD34+ enriched normal bone marrow cells (n=5) were depicted with a symbol. FIG. 8I: the mean fluorescence intensity of IL1RAP on CD34+ enriched AML cells of G0 phase and G1 phase was compared (2768 vs. 3181, no significant difference).

FIG. 9A: ADCC efficacy of 12 candidate monoclonal antibodies determined by $Cr^{51}$ release assay. 1D5 showed the most potent ADCC efficacy. FIG. 9B: SDS-PAGE gel of purified antibodies. Reduced samples were loaded to lane 1-3, Non-reduced samples were loaded to lane 5-7. Anti-CD3 scFv-knob FC (1 and 5), Anti-IL1RAP scFv-hole FC(2 and 6), and anti-IL1RAP/CD3 bispecific antibody (3 and 7).

FIG. 10A: T cell dependant cellular cytotoxicity (TDCC) was tested with the incubation of T cell and different AML cell lines (HL60, MV4-11, THP-1 and KG-1a) at a E:T ratio of 1:1, the specific lysis percentage was checked at 48 hours after incubation. The specific lysis was determined by flow cytometry, calculated using the formula: % Specific lyses= [(Target cells$^{+T\ cells}$−Target cells$^{+BsAb+T\ cells}$)]/Target cells$^{+T\ cells}$)×100%. The average IC50 is 45.14 pM. FIG. 10B: T cells were activated in the killing assay as indicated by the upregulation of CD25 and CD69. FIG. 10C: cytokines released by T cells in the same killing assay were quantified by ELISA. FIG. 10D: the killing potency was compared when long-term killing assay with MV4-11 cells was performed at different E:T ratio and different antibody concentration. FIG. 10E: anti-IL1RAP/CD3 bispecific antibody induced specific lysis of CD34+ enriched AML cells in the long-term killing assay with T cells from healthy donor at E:T ratio of 1:1. Cytokines, TNF-a (FIG. 10F), IFN-r (FIG. 10G), and Granzyme B (FIG. 10H) were quantified by ELISA. FIG. 10I: long-term killing assay with AML primary samples using autologous T cells was conducted. In this sample, the T cell percentage is 8.97%. Two more samples were tested (FIG. 14) FIG. 10J: anti-CD19/CD3 isotype control showed baseline killing in the autologous T cell killing assay. FIG. 10K: addition of recombinant IL1RAP in the long-term killing assay showed no significant interference of the killing potency for anti-IL1RAP/CD3 bispecific antibody.

FIG. 11A: IL1RAP, CD123 and CD33 expression on CD34+ enriched cells from normal bone marrow. FIG. 11B: $1\times10^4$ CD34+ normal bone marrow cells from three different healthy donor were mixed with autologous T cells at E:T ratio of 1:1 in the addition of MM001 at different concentrations (3.15 nM, 1.05 nM, and 0 nM) for 24 hours. Then one fourth of the cells were preceded for colony forming assay. The colony numbers were compared. The specific killing of CD34+ enriched normal bone marrow cells by MM001 (FIG. 11C) and isotype control (FIG. 11D) were determined by 48 hours long-term killing assay.

FIG. 12A; experiment design. $1\times10^6$ MV4-11 cells were injected to each mouse via tail vein. Treatment started on day 7 with 200 ug bispecific antibody and $3\times10^6$ T cell per mouse. The subsequent treatment and imaging time were indicted by the arrow. FIG. 12B: tumor growth was monitored by bioluminescence imaging. Massive infiltration of leukemia was seen in the NSG mice transplanted with MV4-11$^{Luci}$ cells treated with vehicle, T cells only, or control BsAb plus T cells. FIG. 12C: Kaplan-Meier analysis of survival for each group (n=5). Notably, mice treated with T cells had also a shorter survival than the control mice, probably due to the toxicity of T cells. Mice treated with BsAb were losing weight, likely due to the cytokine release. FIG. 12D: bioluminescent signal for each treatment group over time.

Figure 1A:
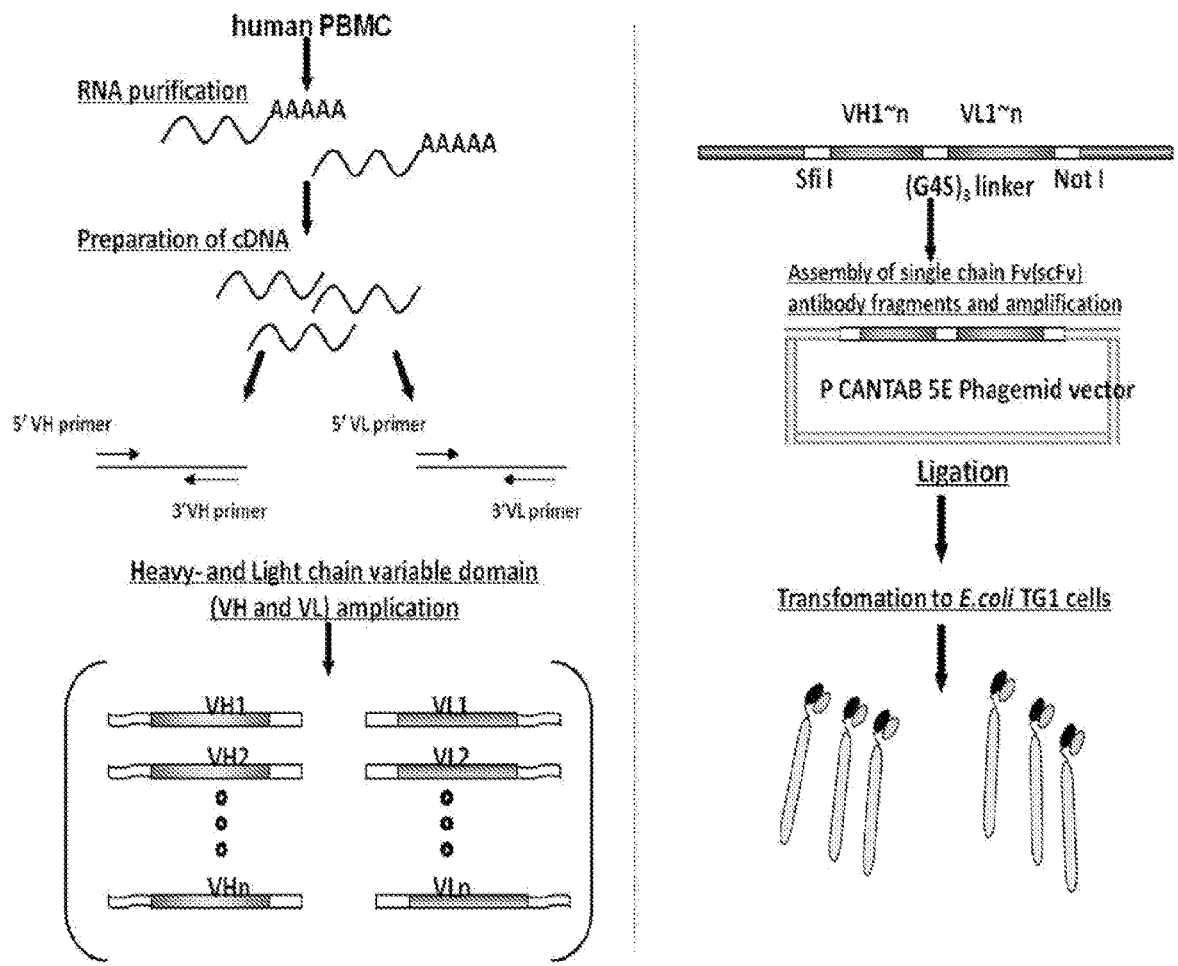
FIG. 1A-1D. Construction of human naive phage display library.

Cytokines were determined by ELISA for IFN-γ (Panel 1), TNF-α(Panel 2), and Granzyme B (Panel 3). 16D: killing of CD34+ 1003 AML cells by IL1RAP-specific CAR-T cells at indicated E: T ratio. Cytokines were determined by ELISA for IFN-γ (Panel 1), TNF-α(Panel 2), and Granzyme B (Panel 3).

DETAILED DESCRIPTION OF THE INVENTION

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of 150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains of an antibody or fragment thereof. Non-limiting examples of antibody variants include single-domain antibodies or nanobodies, affibodies (polypeptides smaller than monoclonal antibodies (e.g., about 6 kDA) and capable of binding antigens with high affinity and imitating monoclonal antibodies, monospecific Fab$_2$, bispecific Fab$_2$, trispecific Fab$_3$, monovalent IgGs, scFv, bispecific diabodies, trispecific triabodies, scFv-Fc, minibodies, IgNAR, V-NAR, hcIgG, VhH, or peptibodies. A "nanobody" or "single domain antibody" as described herein is commonly well known in the art and refers to an antibody fragment consisting of a single monomeric variable antibody domain. Like a whole antibody, it is able to bind selectively to a specific antigen. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805, which are incorporated, by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR H2", "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H1}$ by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., *Cancer Res.* 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa. In embodiments, the linker includes more than one serine. In embodiments, the linker includes more than one glycine. In embodiments, the linker has the strucutre of -(Gly-Gly-Gly-Gly-Ser)$_3$- (SEQ ID NO:19).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321:522; and Verhoyen et al. (1988) *Science*

239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or antibody, antibody variant, antibody region or fragment thereof.

The term "IL1RAP" as used herein refers to any recombinant or naturally-occurring forms of interleukin-1 receptor accessory protein (IL1RAP) or variants or homologs thereof that maintain IL1RAP activity (e.g. within at least 50%, 80%, 90%, 95%, 96%, 97%, 98%, 99% or 100% activity compared to IL1RAP). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring IL1RAP polypeptide. In embodiments, IL1RAP is substantially identical to the protein identified by the UniProt reference number Q9NPH3 or a variant or homolog having substantial identity thereto.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. antibodies and antigens) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include, but are not limited to, yeast cells and cells derived from plants and animals, for example mammalian, insect (e.g., spodoptera) and human cells.

A "stem cell" as provided herein refers to a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. In embodiments, the stem cell is a leukemia stem cell (LSC). A "leukemia stem cell or "LSC" as provided herein refers to a cell capable of initiating the disease (leukemia) when transplanted into immunodeficient animals and can self-renew by giving rise to leukemia in serial transplantations and also partially differentiate into non-LSC bulk blasts that resemble the original disease but are unable to self-renew. An LSC may carry a gene mutation and be able to self-renew through mitotic cell division and differentiate into the hematopoietic lineage carrying said gene mutant or an LSC may remain as immature progenitor cells, also known as blast cells. In embodiments, the LSC expresses CD34.

The term "CD34" as referred to herein includes any of the recombinant or naturally-occurring forms of the cluster of differentiation 34 protein, or variants or homologs thereof that maintain CD34 activity (e.g. within at least 50%, 80%, 90%, 95%, 96%, 97%, 98%, 99% or 100% activity compared to CD34). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD34 protein. In embodiments, the CD34 protein is substantially identical to the protein identified by the UniProt reference number P28906 or a variant or homolog having substantial identity thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "exogenous" refers to a molecule or substance (e.g., a compound, nucleic acid or protein) that originates from outside a given cell or organism. For example, an "exogenous promoter" as referred to herein is a promoter that does not originate from the cell or organism it is expressed by. Conversely, the term "endogenous" or "endogenous promoter" refers to a molecule or substance that is native to, or originates within, a given cell or organism.

As defined herein, the term "inhibition", "inhibit", "inhibiting" and the like in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophagelike synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer (e.g. leukemia, acute myeloid leukemia)) means that the disease (e.g., cancer (e.g. leukemia, acute myeloid leukemia)) is caused by (in whole or in part), or a symptom of the disease is caused by (in whole or in part) the substance or substance activity or function. Alternatively, the substance (e.g., IL1RAP) may be an indicator of the disease (e.g., cancer (e.g. leukemia, acute myeloid leukemia)). Thus, an associated substance may serve as a means of targeting disease tissue (e.g., cancer cells (e.g., leukemia stem cells, acute myeloid leukemia cells)).

As used herein, "treating" or "treatment of" a condition, disease or disorder or symptoms associated with a condition, disease (e.g., cancer, e.g., AML) or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

In embodiments, the method further includes administering to the subject an additional therapeutic agent. As described above, a therapeutic agent is a composition useful in treating or preventing a disease such as cancer. In embodiments, the additional therapeutic agent is an anti-cancer agent.

The terms "anti-cancer agent" and "anticancer agent" are used in accordance with their plain ordinary meaning and refer to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixinab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodeoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or r1L.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to 111In, 90Y, or 131I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/ BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention (e.g., antibody, bispecific antibody or chimeric antigen receptor) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Antibody Compositions

Provided herein are, inter alia, antibodies capable of binding Interleukin-1 receptor accessory protein (IL1RAP). The antibodies provided herein include novel light chain and heavy chain sequences and bind IL1RAP with high efficiency and specificity, thereby blocking IL-1 signaling. Blocking of IL-1 signaling results in the inhibition of proliferation of IL1RAP-expressing cells. Further, through the recruitment of effector cells, the anti-ILRAP1 antibodies provided herein are able to induce cell killing of IL1RAP-expressing cells. IL1RAP is expressed on a variety of cell types, for example, on candidate leukemic stem cells acute myeloid leukemia (AML) patients, but not on normal hematopoietic stem cells. Thus, the anti-IL1RAP antibodies provided herein are, inter alia, useful for the treatment of IL1RAP-expressing cancers such as AML.

In an aspect is provided an anti-interleukin-1 receptor accessory protein (IL1RAP) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

As described above, a "light chain variable (VL) domain" as provided herein refers to the variable region of the light chain of an antibody, an antibody variant or fragment thereof. Likewise, the "heavy chain variable (VH) domain" as provided herein refers to the variable region of the heavy chain of an antibody, an antibody variant or fragment thereof. The light chain variable domain and the heavy chain variable domain together form the paratope, which binds an antigen (epitope). The paratope or antigen-binding site is formed at the N-terminus of an antibody, an antibody variant or fragment thereof. In embodiments, the light chain variable (VL) domain includes CDR L1, CDR L2, CDR L3 and FR L1, FR L2, FR L3 and FR L4 (framework regions) of an antibody light chain. In embodiments, the heavy chain variable (VH) domain includes CDR H1, CDR H2, CDR H3 and FR H1, FR H2, FR H3 and FR H4 (framework regions) of an antibody heavy chain. In embodiments, the light chain variable (VL) domain and a light chain constant (CL) domain form part of an antibody light chain. In embodiments, the heavy chain variable (VH) domain and a heavy chain constant (CH1) domain form part of an antibody heavy chain. In embodiments, the heavy chain variable (VH) domain and one or more heavy chain constant (CH1, CH2, or CH3) domains form part of an antibody heavy chain. Thus, in embodiments, the light chain variable (VL) domain forms part of an antibody. In embodiments, the heavy chain variable (VH) domain forms part of an antibody. In embodiments, the light chain variable (VL) domain forms part of a therapeutic antibody. In embodiments, the heavy chain variable (VH) domain forms part of a therapeutic antibody. In embodiments, the light chain variable (VL) domain forms part of a human antibody. In embodiments, the heavy chain variable (VH) domain forms part of a human antibody. In embodiments, the light chain variable (VL) domain forms part of a humanized antibody. In embodiments, the heavy chain variable (VH) domain forms part of a humanized antibody. In embodiments, the light chain variable (VL) domain forms part of a chimeric antibody. In embodiments, the heavy chain variable (VH) domain forms part of a chimeric antibody. In embodiments, the light chain variable (VL) domain forms part of an antibody fragment. In embodiments, the heavy chain variable (VH) domain forms part of an antibody fragment. In embodiments, the light chain variable (VL) domain forms part of an antibody variant. In embodiments, the heavy chain variable (VH) domain forms part of an antibody variant. In embodiments, the light chain variable (VL) domain forms part of a Fab. In embodiments, the heavy chain variable (VH) domain forms part of a Fab. In embodiments, the light chain variable (VL) domain forms part of a scFv. In embodiments, the heavy chain variable (VH) domain forms part of a scFv.

In embodiments, the light chain variable domain includes the sequence of SEQ ID NO:7. In embodiments, the light chain variable domain is the sequence of SEQ ID NO:7. In embodiments, the heavy chain variable domain includes the sequence of SEQ ID NO:8. In embodiments, the heavy chain variable domain is the sequence of SEQ ID NO:8. In embodiments, light chain variable domain includes a FR L1 as set forth in SEQ ID NO:9, a FR L2 as set forth in SEQ ID NO:10, FR L3 as set forth in SEQ ID NO:11 and a FR L4 as set forth in SEQ ID NO:12. In embodiments, the heavy chain variable domain includes a FR H1 as set forth in SEQ ID NO:13, a FR H2 as set forth in SEQ ID NO:14, FR H3 as set forth in SEQ ID NO:15 and a FR H4 as set forth in SEQ ID NO:16.

In one embodiment, the antibody includes (i) a light chain variable domain including a CDR L1 as set forth in SEQ ID NO:1, a CDR L2 as set forth in SEQ ID NO:2; a CDR L3 as set forth in SEQ ID NO:3; a FR L1 as set forth in SEQ ID NO:9, a FR L2 as set forth in SEQ ID NO:10, FR L3 as set forth in SEQ ID NO:11 and a FR L4 as set forth in SEQ ID NO:12; and (ii) a heavy chain variable domain including a CDR H1 as set forth in SEQ ID NO:4, a CDR H2 as set forth in SEQ ID NO:5, a CDR H3 as set forth in SEQ ID NO:6; a FR H1 as set forth in SEQ ID NO:13, a FR H2 as set forth in SEQ ID NO:14, FR H3 as set forth in SEQ ID NO:15 and a FR H4 as set forth in SEQ ID NO:16.

In one embodiment, the antibody includes a light chain variable domain of SEQ ID NO:7 and a heavy chain variable domain of SEQ ID NO:8.

In embodiments, the antibody is an IgG. In embodiments, the antibody is a human IgG. In embodiments, the antibody is an IgG1. In embodiments, the antibody is a human IgG1.

In embodiments, the antibody is a Fab' fragment. In embodiments, the antibody forms part of a Fab' fragment. In embodiments, the antibody is a single chain antibody (scFv). In embodiments, the light chain variable domain and the heavy chain variable domain form part of an scFv. In embodiments, the scFv includes the sequence of SEQ ID NO:17. In embodiments, the scFv is the sequence of SEQ ID NO:17.

The ability of an antibody to bind a specific epitope (e.g., IL1RAP) can be described by the equilibrium dissociation constant ($K_D$). The equilibrium dissociation constant ($K_D$) as defined herein is the ratio of the dissociation rate (K-off) and the association rate (K-on) of an antibody to IL1RAP. It is described by the following formula: $K_D$=K-off/K-on. In embodiments, the antibody is capable of binding IL1RAP with an equilibrium dissociation constant ($K_D$) of about 21 nM. In embodiments, the antibody is capable of binding IL1RAP with an equilibrium dissociation constant ($K_D$) of 21 nM. In embodiments, the antibody is capable of binding IL1RAP with an equilibrium dissociation constant ($K_D$) of about 80.6 nM. In embodiments, the antibody is capable of binding IL1RAP with an equilibrium dissociation constant ($K_D$) of 80.6 nM.

In embodiments, the antibody is capable of binding IL1RAP with an equilibrium dissociation constant ($K_D$) from 20 to 25 nM. In embodiments, the antibody is capable of binding IL1RAP with an equilibrium dissociation constant ($K_D$) from 21 to 25 nM. In embodiments, the antibody is capable of binding IL1RAP with an equilibrium dissociation constant ($K_D$) from 22 to 25 nM. In embodiments, the antibody is capable of binding IL1RAP with an equilibrium dissociation constant ($K_D$) from 23 to 25 nM. In embodiments, the antibody is capable of binding IL1RAP with an equilibrium dissociation constant ($K_D$) from 24 to 25 nM.

In embodiments, the antibody is capable of binding IL1RAP with an equilibrium dissociation constant ($K_D$) from 75 to 85 nM. In embodiments, the antibody is capable of binding IL1RAP with an equilibrium dissociation constant ($K_D$) from 76 to 85 nM. In embodiments, the antibody is capable of binding IL1RAP with an equilibrium dissociation constant ($K_D$) from 77 to 85 nM. In embodiments, the antibody is capable of binding IL1RAP with an equilibrium dissociation constant ($K_D$) from 78 to 85 nM. In embodiments, the antibody is capable of binding IL1RAP with an equilibrium dissociation constant ($K_D$) from 79 to 85 nM. In embodiments, the antibody is capable of binding IL1RAP with an equilibrium dissociation constant ($K_D$) from 80 to 85 nM. In embodiments, the antibody is capable of binding IL1RAP with an equilibrium dissociation constant ($K_D$) from 81 to 85 nM. In embodiments, the antibody is capable of binding IL1RAP with an equilibrium dissociation constant ($K_D$) from 82 to 85 nM. In embodiments, the antibody is capable of binding IL1RAP with an equilibrium dissociation constant ($K_D$) from 83 to 85 nM. In embodiments, the antibody is capable of binding IL1RAP with an equilibrium dissociation constant ($K_D$) from 84 to 85 nM.

In embodiments, the antibody is capable of binding IL1RAP with an equilibrium dissociation constant ($K_D$) from about 20 to about 85 nM. In embodiments, the antibody is capable of binding IL1RAP with an equilibrium dissociation constant ($K_D$) from about 25 to about 85 nM. In embodiments, the antibody is capable of binding IL1RAP with an equilibrium dissociation constant ($K_D$) from about 30 to about 85 nM. In embodiments, the antibody is capable of binding IL1RAP with an equilibrium dissociation constant ($K_D$) from about 35 to about 85 nM. In embodiments, the antibody is capable of binding IL1RAP with an equilibrium dissociation constant ($K_D$) from about 40 to about 85 nM. In embodiments, the antibody is capable of binding IL1RAP with an equilibrium dissociation constant ($K_D$) from about 45 to about 85 nM. In embodiments, the antibody is capable of binding IL1RAP with an equilibrium dissociation constant ($K_D$) from about 50 to about 85 nM. In embodiments, the antibody is capable of binding IL1RAP with an equilibrium dissociation constant ($K_D$) from about 55 to about 85 nM. In embodiments, the antibody is capable of binding IL1RAP with an equilibrium dissociation constant ($K_D$) from about 60 to about 85 nM. In embodiments, the antibody is capable of binding IL1RAP with an equilibrium dissociation constant ($K_D$) from about 65 to about 85 nM. In embodiments, the antibody is capable of binding IL1RAP with an equilibrium dissociation constant ($K_D$) from about 70 to about 85 nM. In embodiments, the antibody is capable of binding IL1RAP with an equilibrium dissociation constant ($K_D$) from about 75 to about 85 nM. In embodiments, the antibody is capable of binding IL1RAP with an equilibrium dissociation constant ($K_D$) from about 80 to about 85 nM.

In embodiments, the antibody is capable of binding IL1RAP with an equilibrium dissociation constant ($K_D$)

from about 20 to about 80 nM. In embodiments, the antibody is capable of binding IL1RAP with an equilibrium dissociation constant ($K_D$) from about 25 to about 80 nM. In embodiments, the antibody is capable of binding IL1RAP with an equilibrium dissociation constant ($K_D$) from about 30 to about 80 nM. In embodiments, the antibody is capable of binding IL1RAP with an equilibrium dissociation constant ($K_D$) from about 35 to about 80 nM. In embodiments, the antibody is capable of binding IL1RAP with an equilibrium dissociation constant ($K_D$) from about 40 to about 80 nM. In embodiments, the antibody is capable of binding IL1RAP with an equilibrium dissociation constant ($K_D$) from about 45 to about 80 nM. In embodiments, the antibody is capable of binding IL1RAP with an equilibrium dissociation constant ($K_D$) from about 50 to about 80 nM. In embodiments, the antibody is capable of binding IL1RAP with an equilibrium dissociation constant ($K_D$) from about 55 to about 80 nM. In embodiments, the antibody is capable of binding IL1RAP with an equilibrium dissociation constant ($K_D$) from about 60 to about 80 nM. In embodiments, the antibody is capable of binding IL1RAP with an equilibrium dissociation constant ($K_D$) from about 65 to about 80 nM. In embodiments, the antibody is capable of binding IL1RAP with an equilibrium dissociation constant ($K_D$) from about 70 to about 80 nM. In embodiments, the antibody is capable of binding IL1RAP with an equilibrium dissociation constant ($K_D$) from about 75 to about 80 nM.

In embodiments, the antibody is capable of binding IL1RAP with an equilibrium dissociation constant ($K_D$) from about 20 to about 70 nM. In embodiments, the antibody is capable of binding IL1RAP with an equilibrium dissociation constant ($K_D$) from about 25 to about 70 nM. In embodiments, the antibody is capable of binding IL1RAP with an equilibrium dissociation constant ($K_D$) from about 30 to about 70 nM. In embodiments, the antibody is capable of binding IL1RAP with an equilibrium dissociation constant ($K_D$) from about 35 to about 70 nM. In embodiments, the antibody is capable of binding IL1RAP with an equilibrium dissociation constant ($K_D$) from about 40 to about 70 nM. In embodiments, the antibody is capable of binding IL1RAP with an equilibrium dissociation constant ($K_D$) from about 45 to about 70 nM. In embodiments, the antibody is capable of binding IL1RAP with an equilibrium dissociation constant ($K_D$) from about 50 to about 70 nM. In embodiments, the antibody is capable of binding IL1RAP with an equilibrium dissociation constant ($K_D$) from about 55 to about 70 nM. In embodiments, the antibody is capable of binding IL1RAP with an equilibrium dissociation constant ($K_D$) from about 60 to about 70 nM. In embodiments, the antibody is capable of binding IL1RAP with an equilibrium dissociation constant ($K_D$) from about 65 to about 70 nM.

In embodiments, the antibody is capable of binding IL1RAP with an equilibrium dissociation constant ($K_D$) from about 20 to about 60 nM. In embodiments, the antibody is capable of binding IL1RAP with an equilibrium dissociation constant ($K_D$) from about 25 to about 60 nM. In embodiments, the antibody is capable of binding IL1RAP with an equilibrium dissociation constant ($K_D$) from about 30 to about 60 nM. In embodiments, the antibody is capable of binding IL1RAP with an equilibrium dissociation constant ($K_D$) from about 35 to about 60 nM. In embodiments, the antibody is capable of binding IL1RAP with an equilibrium dissociation constant ($K_D$) from about 40 to about 60 nM. In embodiments, the antibody is capable of binding IL1RAP with an equilibrium dissociation constant ($K_D$) from about 45 to about 60 nM. In embodiments, the antibody is capable of binding IL1RAP with an equilibrium dissociation constant ($K_D$) from about 50 to about 60 nM. In embodiments, the antibody is capable of binding IL1RAP with an equilibrium dissociation constant ($K_D$) from about 55 to about 60 nM.

In embodiments, the antibody is capable of binding IL1RAP with an equilibrium dissociation constant ($K_D$) from about 20 to about 50 nM. In embodiments, the antibody is capable of binding IL1RAP with an equilibrium dissociation constant ($K_D$) from about 25 to about 50 nM. In embodiments, the antibody is capable of binding IL1RAP with an equilibrium dissociation constant ($K_D$) from about 30 to about 50 nM. In embodiments, the antibody is capable of binding IL1RAP with an equilibrium dissociation constant ($K_D$) from about 35 to about 50 nM. In embodiments, the antibody is capable of binding IL1RAP with an equilibrium dissociation constant ($K_D$) from about 40 to about 50 nM. In embodiments, the antibody is capable of binding IL1RAP with an equilibrium dissociation constant ($K_D$) from about 45 to about 50 nM.

In embodiments, the antibody is capable of binding IL1RAP with an equilibrium dissociation constant ($K_D$) from about 20 to about 40 nM. In embodiments, the antibody is capable of binding IL1RAP with an equilibrium dissociation constant ($K_D$) from about 25 to about 40 nM. In embodiments, the antibody is capable of binding IL1RAP with an equilibrium dissociation constant ($K_D$) from about 30 to about 40 nM. In embodiments, the antibody is capable of binding IL1RAP with an equilibrium dissociation constant ($K_D$) from about 35 to about 40 nM.

In embodiments, the antibody is capable of binding IL1RAP with an equilibrium dissociation constant ($K_D$) from about 20 to about 30 nM. In embodiments, the antibody is capable of binding IL1RAP with an equilibrium dissociation constant ($K_D$) from about 25 to about 30 nM.

In embodiments, the antibody has an $EC_{50}$ from about 1 ng/ml to about 20 ng/ml. In embodiments, the antibody has an $EC_{50}$ from about 2 ng/ml to about 20 ng/ml. In embodiments, the antibody has an $EC_{50}$ from about 3 ng/ml to about 20 ng/ml. In embodiments, the antibody has an $EC_{50}$ from about 4 ng/ml to about 20 ng/ml. In embodiments, the antibody has an $EC_{50}$ from about 5 ng/ml to about 20 ng/ml. In embodiments, the antibody has an $EC_{50}$ from about 6 ng/ml to about 20 ng/ml. In embodiments, the antibody has an $EC_{50}$ from about 7 ng/ml to about 20 ng/ml. In embodiments, the antibody has an $EC_{50}$ from about 8 ng/ml to about 20 ng/ml. In embodiments, the antibody has an $EC_{50}$ from about 9 ng/ml to about 20 ng/ml. In embodiments, the antibody has an $EC_{50}$ from about 10 ng/ml to about 20 ng/ml.

In embodiments, the antibody has an $EC_{50}$ from about 11 ng/ml to about 20 ng/ml. In embodiments, the antibody has an $EC_{50}$ from about 12 ng/ml to about 20 ng/ml. In embodiments, the antibody has an $EC_{50}$ from about 13 ng/ml to about 20 ng/ml. In embodiments, the antibody has an $EC_{50}$ from about 14 ng/ml to about 20 ng/ml. In embodiments, the antibody has an $EC_{50}$ from about 15 ng/ml to about 20 ng/ml. In embodiments, the antibody has an $EC_{50}$ from about 16 ng/ml to about 20 ng/ml. In embodiments, the antibody has an $EC_{50}$ from about 17 ng/ml to about 20 ng/ml. In embodiments, the antibody has an $EC_{50}$ from about 18 ng/ml to about 20 ng/ml. In embodiments, the antibody has an $EC_{50}$ from about 19 ng/ml to about 20 ng/ml.

In embodiments, the antibody has an $EC_{50}$ from about 1 to about 19 ng/ml. In embodiments, the antibody has an $EC_{50}$ from about 1 ng/ml to about 18 ng/ml. In embodiments, the antibody has an $EC_{50}$ from about 1 ng/ml to about 17 ng/ml. In embodiments, the antibody has an $EC_{50}$ from about 1 ng/ml to about 16 ng/ml. In embodiments, the antibody has an $EC_{50}$ from about 1 ng/ml to about 15 ng/ml. In embodiments, the antibody has an $EC_{50}$ from about 1 ng/ml to about 14 ng/ml. In embodiments, the antibody has an $EC_{50}$ from about 1 ng/ml to about 13 ng/ml. In embodiments, the antibody has an $EC_{50}$ from about 1 ng/ml to about 12 ng/ml. In embodiments, the antibody has an $EC_{50}$ from about 1 ng/ml to about 11 ng/ml.

In embodiments, the antibody has an $EC_{50}$ from about 1 ng/ml to about 10 ng/ml. In embodiments, the antibody has an $EC_{50}$ from about 1 ng/ml to about 9 ng/ml. In embodiments, the antibody has an $EC_{50}$ from about 1 ng/ml to about 8 ng/ml. In embodiments, the antibody has an $EC_{50}$ from about 1 ng/ml to about 7 ng/ml. In embodiments, the antibody has an $EC_{50}$ from about 1 ng/ml to about 6 ng/ml. In embodiments, the antibody has an $EC_{50}$ from about 1 ng/ml to about 5 ng/ml. In embodiments, the antibody has an $EC_{50}$ from about 1 ng/ml to about 4 ng/ml. In embodiments, the antibody has an $EC_{50}$ from about 1 ng/ml to about 3 ng/ml. In embodiments, the antibody has an $EC_{50}$ from about 1 ng/ml to about 2 ng/ml.

In embodiments, the antibody has an $EC_{50}$ of about 1 ng/ml, 2 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml or 20 ng/ml. In embodiments, the antibody has an $EC_{50}$ of 1 ng/ml, 2 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml or 20 ng/ml.

In embodiments, the antibody has an $EC_{50}$ from about 4 ng/ml to about 7 ng/ml. In embodiments, the antibody has an $EC_{50}$ from about 4.5 ng/ml to about 7 ng/ml. In embodiments, the antibody has an $EC_{50}$ from about 5 ng/ml to about 7 ng/ml. In embodiments, the antibody has an $EC_{50}$ from about 5.5 ng/ml to about 7 ng/ml. In embodiments, the antibody has an $EC_{50}$ from about 6 ng/ml to about 7 ng/ml. In embodiments, the antibody has an $EC_{50}$ from about 6.5 ng/ml to about 7 ng/ml.

In embodiments, the antibody has an $EC_{50}$ from 4 ng/ml to 7 ng/ml. In embodiments, the antibody has an $EC_{50}$ from 4.5 ng/ml to 7 ng/ml. In embodiments, the antibody has an $EC_{50}$ from 5 ng/ml to 7 ng/ml. In embodiments, the antibody has an $EC_{50}$ from 5.5 ng/ml to 7 ng/ml. In embodiments, the antibody has an $EC_{50}$ from 6 ng/ml to 7 ng/ml. In embodiments, the antibody has an $EC_{50}$ from 6.5 ng/ml to 7 ng/ml.

In embodiments, the antibody has an $EC_{50}$ of about 4.9 ng/ml. In embodiments, the antibody has an $EC_{50}$ of 4.9 ng/ml. In embodiments, the antibody has an $EC_{50}$ of about 6.8 ng/ml. In embodiments, the antibody has an $EC_{50}$ of 6.8 ng/ml. In embodiments, the antibody has an $EC_{50}$ of about 6.4 ng/ml. In embodiments, the antibody has an $EC_{50}$ of 6.4 ng/ml. In embodiments, the antibody has an $EC_{50}$ of about 5.4 ng/ml. In embodiments, the antibody has an $EC_{50}$ of 5.4 ng/ml.

In embodiments, the antibody is bound to an IL1RAP. In embodiments, the IL1RAP is a human IL1RAP. In embodiments, the IL1RAP forms part of a cell. In embodiments, the IL1RAP is expressed on the surface of the cell. In embodiments, the cell is a cancer cell. In embodiments, the cancer cell is a leukemia stem cell (LSC). In embodiments, the cancer cell is an acute myeloid leukemia (AML) cell. In embodiments, the cancer cell is a chronic myeloid leukemia (CML) cell. In embodiments, the cancer cell is a lung cancer cell. In embodiments, the cancer cell is a non-small cell lung cancer (NSCLC) cell. In embodiments, the cancer cell is a pancreatic cancer cell. In embodiments, the cancer cell is a melanoma cell. In embodiments, the cancer cell is a breast cancer cell. In embodiments, the cancer cell is a colon cancer cell.

In embodiments, the anti-interleukin-1 receptor accessory protein (IL1RAP) antibody has the sequence of SEQ ID NO: 17.

Recombinant Protein Compositions

As described above, the light chain variable (VL) domain and the heavy chain variable (VH) domain as provided herein including embodiments thereof may each independently form part of an antibody, an antibody variant, a fragment of an antibody, a fragment of an antibody variant, or a recombinant protein (e.g., a chimeric antigen receptor, bispecific antibody). Provided herein are recombinant proteins (e.g., a chimeric antigen receptor, a bispecific antibody) which include the light chain variable (VL) domain and the heavy chain variable (VH) domain as provided herein and are therefore capable of binding IL1RAP and recruiting effector cells to IL1RAP-expressing cells (e.g., LSCs) thereby eliminating the IL1RAP-expressing cells. In embodiments, the recombinant protein is a chimeric antigen receptor (CAR). In embodiments, the recombinant protein is a bispecific antibody.

The light chain variable (VL) domain and the heavy chain variable (VH) domain as provided herein may form part of a chimeric antigen receptor. Thus, in an aspect is provided a recombinant protein including: (i) an antibody region including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable region domain a CDR H1 as set forth in SEQ ID NO:4, a CDR H2 as set forth in SEQ ID NO:5, and a CDR H3 as set forth in SEQ ID NO:6; and (ii) a transmembrane domain.

An "antibody region" as provided herein refers to a monovalent or multivalent protein moiety that forms part of the recombinant protein (e.g., CAR) provided herein including embodiments thereof. A person of ordinary skill in the art would therefore immediately recognize that the antibody region is a protein moiety capable of binding an antigen (epitope). Thus, the antibody region provided herein may include a domain of an antibody (e.g., a light chain variable (VL) domain, a heavy chain variable (VH) domain) or a fragment of an antibody (e.g., Fab). In embodiments, the antibody region is a protein conjugate. A "protein conjugate" as provided herein refers to a construct consisting of more than one polypeptide, wherein the polypeptides are bound together covalently or non-covalently. In embodiments, the protein conjugate includes a Fab moiety (a monovalent Fab) covalently attached to an scFv moiety (a monovalent scFv). In embodiments, the protein conjugate includes a plurality (at least two) Fab moieties. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker. In embodiments, the antibody region is an scFv.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include, the transmembrane domains of CD28, CD8, CD4 or CD3-zeta. In embodiments, the transmembrane domain is a CD4 transmembrane domain.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

In embodiments, light chain variable domain includes the sequence of SEQ ID NO:7. In embodiments, light chain variable domain is the sequence of SEQ ID NO:7. In embodiments, the heavy chain variable domain incudes the sequence of SEQ ID NO:8. In embodiments, the heavy chain variable domain is the sequence of SEQ ID NO: 8. In embodiments, the light chain variable domain includes a FR L1 as set forth in SEQ ID NO:9, a FR L2 as set forth in SEQ ID NO:10, FR L3 as set forth in SEQ ID NO:11 and a FR L4 as set forth in SEQ ID NO:12. In embodiments, the heavy chain variable domain includes a FR H1 as set forth in SEQ ID NO:13, a FR H2 as set forth in SEQ ID NO:14, FR H3 as set forth in SEQ ID NO:15 and a FR H4 as set forth in SEQ ID NO:16.

In embodiments, the antibody region includes a single-chain variable fragment (scFv). In embodiments, the scFv includes the sequence of SEQ ID NO:17. In embodiments, the scFv is the sequence of SEQ ID NO:17.

In embodiments, the recombinant protein is capable of binding IL1RAP with an equilibrium dissociation constant ($K_D$) of about 21 nM. In embodiments, the recombinant protein is capable of binding IL1RAP with an equilibrium dissociation constant ($K_D$) of 21 nM. The $K_D$ values defined herein for the IL1RAP antibody do apply for the recombinant proteins described herein including embodiments thereof.

Thus, in embodiments, the recombinant protein (e.g., chimeric antigen receptor) has an $EC_{50}$ (half maximal effective concentration) from about 1 ng/ml to about 20 ng/ml. The term "EC50" or "half maximal effective concentration" as used herein refers to the concentration of a molecule (e.g., antibody, chimeric antigen receptor or bispecific antibody) capable of inducing a response which is halfway between the baseline response and the maximum response after a specified exposure time. In embodiments, the $EC_{50}$ is the concentration of a molecule (e.g., antibody, chimeric antigen receptor or bispecific antibody) that produces 50% of the maximal possible effect of that molecule. In embodiments, the recombinant protein has an $EC_{50}$ from about 2 ng/ml to about 20 ng/ml. In embodiments, the recombinant protein has an $EC_{50}$ from about 3 ng/ml to about 20 ng/ml. In embodiments, the recombinant protein has an $EC_{50}$ from about 4 ng/ml to about 20 ng/ml. In embodiments, the recombinant protein has an $EC_{50}$ from about 5 ng/ml to about 20 ng/ml. In embodiments, the recombinant protein has an $EC_{50}$ from about 6 ng/ml to about 20 ng/ml. In embodiments, the recombinant protein has an $EC_{50}$ from about 7 ng/ml to about 20 ng/ml. In embodiments, the recombinant protein has an $EC_{50}$ from about 8 ng/ml to about 20 ng/ml. In embodiments, the recombinant protein has an $EC_{50}$ from about 9 ng/ml to about 20 ng/ml. In embodiments, the recombinant protein has an $EC_{50}$ from about 10 ng/ml to about 20 ng/ml.

In embodiments, the recombinant protein has an $EC_{50}$ from about 11 ng/ml to about 20 ng/ml. In embodiments, the recombinant protein has an $EC_{50}$ from about 12 ng/ml to about 20 ng/ml. In embodiments, the recombinant protein has an $EC_{50}$ from about 13 ng/ml to about 20 ng/ml. In embodiments, the recombinant protein has an $EC_{50}$ from about 14 ng/ml to about 20 ng/ml. In embodiments, the recombinant protein has an $EC_{50}$ from about 15 ng/ml to about 20 ng/ml. In embodiments, the recombinant protein has an $EC_{50}$ from about 16 ng/ml to about 20 ng/ml. In embodiments, the recombinant protein has an $EC_{50}$ from about 17 ng/ml to about 20 ng/ml. In embodiments, the recombinant protein has an $EC_{50}$ from about 18 ng/ml to about 20 ng/ml. In embodiments, the recombinant protein has an $EC_{50}$ from about 19 ng/ml to about 20 ng/ml.

In embodiments, the recombinant protein has an $EC_{50}$ of about 1 ng/ml, 2 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml or 20 ng/ml. In embodiments, the antibody has an $EC_{50}$ of 1 ng/ml, 2 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml or 20 ng/ml.

In embodiments, the recombinant protein has an $EC_{50}$ from about 1 to about 19 ng/ml. In embodiments, the recombinant protein has an $EC_{50}$ from about 1 ng/ml to about 18 ng/ml. In embodiments, the recombinant protein has an $EC_{50}$ from about 1 ng/ml to about 17 ng/ml. In embodiments, the recombinant protein has an $EC_{50}$ from about 1 ng/ml to about 16 ng/ml. In embodiments, the recombinant protein has an $EC_{50}$ from about 1 ng/ml to about 15 ng/ml. In embodiments, the recombinant protein has an $EC_{50}$ from about 1 ng/ml to about 14 ng/ml. In embodiments, the recombinant protein has an $EC_{50}$ from about 1 ng/ml to about 13 ng/ml. In embodiments, the recombinant protein has an $EC_{50}$ from about 1 ng/ml to about 12 ng/ml. In embodiments, the recombinant protein has an $EC_{50}$ from about 1 ng/ml to about 11 ng/ml.

In embodiments, the recombinant protein has an $EC_{50}$ from about 1 ng/ml to about 10 ng/ml. In embodiments, the recombinant protein has an $EC_{50}$ from about 1 ng/ml to about 9 ng/ml. In embodiments, the recombinant protein has an $EC_{50}$ from about 1 ng/ml to about 8 ng/ml. In embodiments, the recombinant protein has an $EC_{50}$ from about 1 ng/ml to about 7 ng/ml. In embodiments, the recombinant protein has an $EC_{50}$ from about 1 ng/ml to about 6 ng/ml. In embodiments, the recombinant protein has an $EC_{50}$ from about 1 ng/ml to about 5 ng/ml. In embodiments, the recombinant protein has an $EC_{50}$ from about 1 ng/ml to about 4 ng/ml. In embodiments, the recombinant protein has an $EC_{50}$ from about 1 ng/ml to about 3 ng/ml. In embodiments, the recombinant protein has an $EC_{50}$ from about 1 ng/ml to about 2 ng/ml.

In embodiments, the recombinant protein has an $EC_{50}$ from about 4 ng/ml to about 7 ng/ml. In embodiments, the recombinant protein has an $EC_{50}$ from about 4.5 ng/ml to about 7 ng/ml. In embodiments, the recombinant protein has an $EC_{50}$ from about 5 ng/ml to about 7 ng/ml. In embodiments, the recombinant protein has an $EC_{50}$ from about 5.5 ng/ml to about 7 ng/ml. In embodiments, the recombinant protein has an $EC_{50}$ from about 6 ng/ml to about 7 ng/ml. In embodiments, the recombinant protein has an $EC_{50}$ from about 6.5 ng/ml to about 7 ng/ml.

In embodiments, the recombinant protein has an $EC_{50}$ from 4 ng/ml to 7 ng/ml. In embodiments, the recombinant protein has an $EC_{50}$ from 4.5 ng/ml to 7 ng/ml. In embodiments, the recombinant protein has an $EC_{50}$ from 5 ng/ml to 7 ng/ml. In embodiments, the recombinant protein has an $EC_{50}$ from 5.5 ng/ml to 7 ng/ml. In embodiments, the recombinant protein has an $EC_{50}$ from 6 ng/ml to 7 ng/ml. In embodiments, the recombinant protein has an $EC_{50}$ from 6.5 ng/ml to 7 ng/ml.

In embodiments, the recombinant protein has an $EC_{50}$ of about 4.9 ng/ml. In embodiments, the recombinant protein has an $EC_{50}$ of 4.9 ng/ml. In embodiments, the recombinant protein has an $EC_{50}$ of about 6.8 ng/ml. In embodiments, the recombinant protein has an $EC_{50}$ of 6.8 ng/ml. In embodiments, the recombinant protein has an $EC_{50}$ of about 6.4 ng/ml. In embodiments, the recombinant protein has an $EC_{50}$ of 6.4 ng/ml. In embodiments, the recombinant protein has an $EC_{50}$ of about 5.4 ng/ml. In embodiments, the recombinant protein has an $EC_{50}$ of 5.4 ng/ml.

In embodiments, the recombinant protein is bound to an IL1RAP. In embodiments, the IL1RAP is a human IL1RAP. In embodiments, the IL1RAP forms part of a cell. In embodiments, the IL1RAP is expressed on the surface of the cell. In embodiments, the cell is a cancer cell. In embodiments, the cancer cell is a leukemia stem cell (LSC). In embodiments, the cancer cell is an acute myeloid leukemia (AML) cell. In embodiments, the cancer cell is a chronic myeloid leukemia (CML) cell. In embodiments, the cancer cell is a lung cancer cell. In embodiments, the cancer cell is a non-small cell lung cancer (NSCLC) cell. In embodiments, the cancer cell is a pancreatic cancer cell. In embodiments, the cancer cell is a melanoma cell. In embodiments, the cancer cell is a breast cancer cell. In embodiments, the cancer cell is a colon cancer cell.

In embodiments, the antibody region includes an Fc domain. In embodiments, the Fc domain is an IgG4 Fc domain. In embodiments, the antibody region includes an Fc hinge domain. In embodiments, the antibody region includes an IgG4 Fc hinge domain. In embodiments, the antibody region includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the spacer region includes an Fc region. In embodiments, the spacer region is an Fc region. Examples of spacer regions contemplated for the recombinant protein compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region. In embodiments, the spacer region is an IgG4 hinge region. In embodiments, the spacer region is a modified IgG4 hinge region.

In embodiments, the recombinant protein as provided herein, including embodiments thereof, further includes an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is a ICOS intracellular co-stimulatory signaling domain. In embodiments, the intracellular co-stimulatory signaling domain is an OX-40 intracellular co-stimulatory signaling domain.

In embodiments, the recombinant protein as provided herein including embodiments thereof, further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3ζ intracellular T-cell signaling domain.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "PD-1" as referred to herein includes any of the recombinant or naturally-occurring forms of the Programmed cell death protein 1 protein, also known as CD279 (cluster of differentiation 279), or variants or homologs thereof that maintain PD-1 activity (e.g. within at least 50%, 80%, 90%, 95%, 96%, 97%, 98%, 99% or 100% activity compared to PD-1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

In embodiments, the recombinant protein as provided herein including embodiments thereof, further includes a self-cleaving peptidyl sequence. In embodiments, the self-cleaving peptidyl linker sequence is a T2A sequence or a 2A sequence. In embodiments, the self-cleaving peptidyl linker sequence is a T2A sequence. In embodiments, the self-cleaving peptidyl linker sequence is a 2A sequence.

In embodiments, the recombinant protein as provided herein including embodiments thereof, further includes a detectable domain. A "detectable domain" as provided herein is peptide moiety detectable by spectroscopic, photochemical, biochemical, immunochemical, chemical, or other physical means. For example, a detectable domain as provided herein may be a protein or other entity which can be made detectable, e.g., by incorporating a radiolabel or being reactive to an antibody specifically. Any appropriate method known in the art for conjugating an antibody to the label may be employed, e.g., using methods described in Hermanson, Bioconjugate Techniques 1996, Academic Press, Inc., San Diego. In embodiments, the detectable domain is a truncated EGFR (EGFRt) domain. The term "EGFRt" refers to a truncated epidermal growth factor receptor protein lacking intracellular signaling capabilities. As used herein, EGFRt is an inert cell surface molecule which functions as a detectable domain allowing identification of transduced T cells. In embodiments, the recombinant protein forms part of a cell. In embodiments, the recombinant protein forms part of a T cell.

The term "EGFR" as referred to herein includes any of the recombinant or naturally-occurring forms of the epidermal growth factor receptor protein, also known as ErbB-1 and HER1, or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the EGFR protein is substantially identical to the protein identified by the UniProt reference number P00533 or a variant or homolog having substantial identity thereto.

In one embodiment, the recombinant protein includes a light chain variable domain of SEQ ID NO:7, a heavy chain variable domain of SEQ ID NO:8, wherein the transmembrane domain is a CD4 transmembrane domain, the Fc domain is an IgG4 hinge domain, the intracellular co-stimulatory domain is a 4-1BB intracellular co-stimulatory domain, the intracellular T-cell signaling domain is a CD3ζ intracellular T-cell signaling domain, the self-cleaving peptidyl sequence is a T2A sequence, and the detectable domain is a truncated EGFR domain.

In embodiments, the recombinant protein is a chimeric antigen receptor, including an antibody region of SEQ ID NO:17, a CD4 transmembrane domain, a IgG4 hinge domain, a 4-1BB intracellular co-stimulatory domain, a CD3ζ intracellular T-cell signaling domain, a T2A self-cleaving peptidyl sequence and a truncated EGFR domain.

In embodiments, the recombinant protein is a chimeric antigen receptor, including an antibody region of SEQ ID NO:17, a CD8 hinge and a CD8 transmembrane domains, a 4-1BB intracellular co-stimulatory domain, and a CD3ζ intracellular T-cell signaling domain.

In embodiments, the recombinant protein is a chimeric antigen receptor of SEQ ID NO:90.

The light chain variable (VL) domain and the heavy chain variable (VH) domain as provided herein may form part of a bispecific antibody. Thus, in another aspect is provided a recombinant protein including: (i) a first antibody region capable of binding an effector cell ligand; and (ii) a second antibody region, including: (a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable region domain a CDR H1 as set forth in SEQ ID NO:4, a CDR H2 as set forth in SEQ ID NO:5, and a CDR H3 as set forth in SEQ ID NO:6.

The term "effector cell ligand" as provided herein refers to a cell surface molecule expressed on an effector cell of the immune system (e.g., a cytotoxic T cell, a helper T cell, a B cell, a natural killer cell). Upon binding of the first antibody region to the effector cell ligand expressed on the effector cell, the effector cell is activated and able to exert its function (e.g., selective killing or eradication of malignant, infected or otherwise unhealthy cells). In embodiments, the effector cell ligand is a CD3 protein. In embodiments, the effector cell ligand is a CD16 protein. In embodiments, the effector cell ligand is a CD32 protein. In embodiments, the effector cell ligand is a NKp46 protein. The first antibody region as provided herein may be an antibody, an antibody variant, a fragment of an antibody or a fragment of an antibody variant.

A "CD3 protein" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex.

A "CD16 protein" as referred to herein includes any of the recombinant or naturally-occurring forms of the Cluster of Differentiation 16 (CD16) protein, also known as low affinity immunoglobulin gamma Fc region receptor or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

A "CD32 protein" as referred to herein includes any of the recombinant or naturally-occurring forms of the Cluster of Differentiation 32 (CD32) protein, also known as low affinity immunoglobulin gamma Fc region receptor II-A, or variants or homologs thereof that maintain CD32 activity (e.g. within at least 50%, 80%, 90%, 95%, 96%, 97%, 98%, 99% or 100% activity compared to CD32). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD32 protein. In embodiments, the CD32 protein is substantially identical to the protein identified by the UniProt reference number P12318 or a variant or homolog having substantial identity thereto.

A "NKp46 protein" as referred to herein includes any of the recombinant or naturally-occurring forms of the NKp46 protein, also known as natural cytotoxicity triggering receptor 1, or variants or homologs thereof that maintain NKp46 activity (e.g. within at least 50%, 80%, 90%, 95%, 96%, 97%, 98%, 99% or 100% activity compared to NKp46). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NKp46 protein. In embodiments, the NKp46 protein is substantially identical to the protein identified by the UniProt reference number O76036 or a variant or homolog having substantial identity thereto.

In embodiments, the recombinant protein (e.g., bispecific antibody) has an IC50 (half maximal inhibitory concentration) from about 10 pM to about 100 pM. In embodiments, the recombinant protein has an IC50 from about 15 pM to about 100 pM. In embodiments, the recombinant protein has an IC50 from about 20 pM to about 100 pM. In embodiments, the recombinant protein has an IC50 from about 25 pM to about 100 pM. In embodiments, the recombinant protein has an IC50 from about 30 pM to about 100 pM. In embodiments, the recombinant protein has an IC50 from about 35 pM to about 100 pM. In embodiments, the recombinant protein has an IC50 from about 40 pM to about 100 pM. In embodiments, the recombinant protein has an IC50 from about 45 pM to about 100 pM. In embodiments, the recombinant protein has an IC50 from about 50 pM to about 100 pM. In embodiments, the recombinant protein has an IC50 from about 55 pM to about 100 pM. In embodiments, the recombinant protein has an IC50 from about 60 pM to about 100 pM. In embodiments, the recombinant protein has an IC50 from about 65 pM to about 100 pM. In embodiments, the recombinant protein has an IC50 from about 70 pM to about 100 pM. In embodiments, the recombinant protein has an IC50 from about 75 pM to about 100 pM. In embodiments, the recombinant protein has an IC50 from about 80 pM to about 100 pM. In embodiments, the recombinant protein has an IC50 from about 85 pM to about 100 pM. In embodiments, the recombinant protein has an IC50 from about 90 pM to about 100 pM. In embodiments, the recombinant protein has an IC50 from about 95 pM to about 100 pM.

In embodiments, the recombinant protein has an IC50 (the half maximal inhibitory concentration) from 10 pM to 100 pM. In embodiments, the recombinant protein has an IC50 from 15 pM to 100 pM. In embodiments, the recombinant protein has an IC50 from 20 pM to 100 pM. In embodiments, the recombinant protein has an IC50 from 25 pM to 100 pM. In embodiments, the recombinant protein has an IC50 from 30 pM to 100 pM. In embodiments, the recombinant protein has an IC50 from 35 pM to 100 pM. In embodiments, the recombinant protein has an IC50 from 40 pM to 100 pM. In embodiments, the recombinant protein has an IC50 from 45 pM to 100 pM. In embodiments, the recombinant protein has an IC50 from 50 pM to 100 pM. In embodiments, the recombinant protein has an IC50 from 55 pM to 100 pM. In embodiments, the recombinant protein has an IC50 from 60 pM to 100 pM. In embodiments, the recombinant protein has an IC50 from 65 pM to 100 pM. In embodiments, the recombinant protein has an IC50 from 70 pM to 100 pM. In embodiments, the recombinant protein has an IC50 from 75 pM to 100 pM. In embodiments, the recombinant protein has an IC50 from 80 pM to 100 pM. In embodiments, the recombinant protein has an IC50 from 85 pM to 100 pM. In embodiments, the recombinant protein has an IC50 from 90 pM to 100 pM. In embodiments, the recombinant protein has an IC50 from 95 pM to 100 pM.

In embodiments, the recombinant protein has an IC50 from about 40 to about 50 pM. In embodiments, the recombinant protein has an IC50 from about 41 to about 50 pM. In embodiments, the recombinant protein has an IC50 from about 42 to about 50 pM. In embodiments, the recombinant protein has an IC50 from about 43 to about 50 pM. In embodiments, the recombinant protein has an IC50 from about 44 to about 50 pM. In embodiments, the recombinant protein has an IC50 from about 45 to about 50 pM. In embodiments, the recombinant protein has an IC50 from about 46 to about 50 pM. In embodiments, the recombinant protein has an IC50 from about 47 to about 50 pM. In embodiments, the recombinant protein has an IC50 from about 48 to about 50 pM. In embodiments, the recombinant protein has an IC50 from about 49 to about 50 pM.

In embodiments, the recombinant protein has an IC50 from about 40 to about 49 pM. In embodiments, the recombinant protein has an IC50 from about 40 to about 48 pM. In embodiments, the recombinant protein has an IC50 from about 40 to about 47 pM. In embodiments, the recombinant protein has an IC50 from about 40 to about 46 pM. In embodiments, the recombinant protein has an IC50 from about 40 to about 45 pM. In embodiments, the recombinant protein has an IC50 from about 40 to about 44 pM. In embodiments, the recombinant protein has an IC50 from about 40 to about 43 pM. In embodiments, the recombinant protein has an IC50 from about 40 to about 42 pM. In embodiments, the recombinant protein has an IC50 from about 40 to about 41 pM.

In embodiments, the recombinant protein has an IC50 from 40 to 50 pM. In embodiments, the recombinant protein has an IC50 from 41 to 50 pM. In embodiments, the recombinant protein has an IC50 from 42 to 50 pM. In embodiments, the recombinant protein has an IC50 from 43 to 50 pM. In embodiments, the recombinant protein has an IC50 from 44 to 50 pM. In embodiments, the recombinant protein has an IC50 from 45 to 50 pM. In embodiments, the recombinant protein has an IC50 from 46 to 50 pM. In embodiments, the recombinant protein has an IC50 from 47 to 50 pM. In embodiments, the recombinant protein has an IC50 from 48 to 50 pM. In embodiments, the recombinant protein has an IC50 from 49 to 50 pM.

In embodiments, the recombinant protein has an IC50 from 40 to 49 pM. In embodiments, the recombinant protein has an IC50 from 40 to 48 pM. In embodiments, the recombinant protein has an IC50 from 40 to 47 pM. In embodiments, the recombinant protein has an IC50 from 40 to 46 pM. In embodiments, the recombinant protein has an IC50 from 40 to 45 pM. In embodiments, the recombinant protein has an IC50 from 40 to 44 pM. In embodiments, the recombinant protein has an IC50 from 40 to 43 pM. In embodiments, the recombinant protein has an IC50 from 40 to 42 pM. In embodiments, the recombinant protein has an IC50 from 40 to 41 pM.

In embodiments, the recombinant protein has an IC50 from 40 to 48.5 pM. In embodiments, the recombinant protein has an IC50 from 40 to 47.5 pM. In embodiments, the recombinant protein has an IC50 from 40 to 46.5 pM. In embodiments, the recombinant protein has an IC50 from 40 to 45.5 pM. In embodiments, the recombinant protein has an IC50 from 40 to 44.5 pM. In embodiments, the recombinant protein has an IC50 from 40 to 43.5 pM. In embodiments, the recombinant protein has an IC50 from 40 to 42.5 pM. In embodiments, the recombinant protein has an IC50 from 40 to 41.5 pM. In embodiments, the recombinant protein has an IC50 from 40 to 40.5 pM.

In embodiments, the recombinant protein has an IC50 from 40.5 to 49 pM. In embodiments, the recombinant protein has an IC50 from 40.5 to 48 pM. In embodiments, the recombinant protein has an IC50 from 40.5 to 47 pM. In embodiments, the recombinant protein has an IC50 from 40.5 to 46 pM. In embodiments, the recombinant protein has an IC50 from 40.5 to 45 pM. In embodiments, the recombinant protein has an IC50 from 40.5 to 44 pM. In embodiments, the recombinant protein has an IC50 from 40.5 to 43 pM. In embodiments, the recombinant protein has an IC50 from 40.5 to 42 pM. In embodiments, the recombinant protein has an IC50 from 40.5 to 41 pM.

In embodiments, the recombinant protein has an IC50 from 41.5 to 49 pM. In embodiments, the recombinant protein has an IC50 from 41.5 to 48 pM. In embodiments, the recombinant protein has an IC50 from 41.5 to 47 pM. In embodiments, the recombinant protein has an IC50 from 41.5 to 46 pM. In embodiments, the recombinant protein has an IC50 from 41.5 to 45 pM. In embodiments, the recombinant protein has an IC50 from 41.5 to 44 pM. In embodiments, the recombinant protein has an IC50 from 41.5 to 43 pM. In embodiments, the recombinant protein has an IC50 from 41.5 to 42 pM.

In embodiments, the recombinant protein has an IC50 from 42.5 to 49 pM. In embodiments, the recombinant protein has an IC50 from 42.5 to 48 pM. In embodiments, the recombinant protein has an IC50 from 42.5 to 47 pM. In embodiments, the recombinant protein has an IC50 from 42.5 to 46 pM. In embodiments, the recombinant protein has an IC50 from 42.5 to 45 pM. In embodiments, the recombinant protein has an IC50 from 42.5 to 44 pM. In embodiments, the recombinant protein has an IC50 from 42.5 to 43 pM.

In embodiments, the recombinant protein has an IC50 from 43.5 to 49 pM. In embodiments, the recombinant protein has an IC50 from 43.5 to 48 pM. In embodiments, the recombinant protein has an IC50 from 43.5 to 47 pM. In embodiments, the recombinant protein has an IC50 from 43.5 to 46 pM. In embodiments, the recombinant protein has an IC50 from 43.5 to 45 pM. In embodiments, the recombinant protein has an IC50 from 43.5 to 44 pM.

In embodiments, the recombinant protein has an IC50 from 44.5 to 49 pM. In embodiments, the recombinant protein has an IC50 from 44.5 to 48 pM. In embodiments, the recombinant protein has an IC50 from 44.5 to 47 pM. In embodiments, the recombinant protein has an IC50 from 44.5 to 46 pM. In embodiments, the recombinant protein has an IC50 from 44.5 to 45 pM.

In embodiments, the recombinant protein has an IC50 of about 10 pM, 20 pM, 30 pM, 40 pM, 41 pM, 42 pM, 43 pM, 44 pM, 45 pM, 46 pM, 47 pM, 48 pM, 49 pM, 50 pM, 60 pM, 70 pM, 80 pM, 90 pM, or 100 pM. In embodiments, the recombinant protein has an IC50 of 10 pM, 20 pM, 30 pM, 40 pM, 41 pM, 42 pM, 43 pM, 44 pM, 45 pM, 46 pM, 47 pM, 48 pM, 49 pM, 50 pM, 60 pM, 70 pM, 80 pM, 90 pM, or 100 pM.

In embodiments, the recombinant protein has an IC50 of about 45.14 pM. In embodiments, the recombinant protein has an IC50 of 45.14 pM. In embodiments, the recombinant protein has an IC50 of about 45.14 pM. In embodiments, the recombinant protein has an IC50 of 45.14 pM.

In embodiments, the light chain variable domain includes the sequence of SEQ ID NO:7. In embodiments, the light chain variable domain is the sequence of SEQ ID NO:7. In embodiments, the heavy chain variable domain includes the sequence of SEQ ID NO:8. In embodiments, the heavy chain variable domain is the sequence of SEQ ID NO:8. In embodiments, the light chain variable domain includes a FR L1 as set forth in SEQ ID NO:9, a FR L2 as set forth in SEQ ID NO:10, FR L3 as set forth in SEQ ID NO:11 and a FR L4 as set forth in SEQ ID NO:12. In embodiments, the heavy chain variable domain includes a FR H1 as set forth in SEQ ID NO:13, a FR H2 as set forth in SEQ ID NO:14, FR H3 as set forth in SEQ ID NO:15 and a FR H4 as set forth in SEQ ID NO:16.

In embodiments, the recombinant protein (bispecific antibody) includes a tryptophan at a position corresponding to Kabat position 366. In embodiments, the recombinant protein (bispecific antibody) includes a serine at a position corresponding to Kabat position 366. In embodiments, the recombinant protein (bispecific antibody) includes a alanine at a position corresponding to Kabat position 368. In embodiments, the recombinant protein (bispecific antibody) includes a valine at a position corresponding to Kabat position 407. In embodiments, the recombinant protein (bispecific antibody) includes an alanine at a position corresponding to Kabat position 234. In embodiments, the recombinant protein (bispecific antibody) includes an alanine at a position corresponding to Kabat position 235.

In embodiments, the first antibody region is a first Fab' fragment or the second antibody region is a second Fab' fragment. In embodiments, the first antibody region is a single chain variable fragment (scFv) or the second antibody region is a second single chain variable fragment (scFv). In embodiments, the first scFv includes the sequence of SEQ ID NO:17. In embodiments, the second scFv is the sequence of SEQ ID NO:17.

In embodiments, the second antibody region is capable of binding IL1RAP with an equilibrium dissociation constant ($K_D$) of about 21 nM. In embodiments, the second antibody region is capable of binding IL1RAP with an equilibrium dissociation constant ($K_D$) of 21 nM.

In embodiments, the second antibody region has an $EC_{50}$ of about 4.9 ng/ml. In embodiments, the second antibody region has an $EC_{50}$ of 4.9 ng/ml.

In embodiments, the second antibody region is bound to an IL1RAP. In embodiments, the IL1RAP is a human IL1RAP. In embodiments, the IL1RAP forms part of a cell. In embodiments, the IL1RAP is expressed on the surface of the cell.

In embodiments, the cell is a cancer cell. In embodiments, the cancer cell is a leukemia stem cell (LSC). In embodiments, the cancer cell is an acute myeloid leukemia (AML) cell.

In one embodiment, the recombinant protein is a bispecific antibody including a first antibody region of SEQ ID NO:21 and a second antibody region of SEQ ID NO:20.

Nucleic Acid Compositions

In an aspect, an isolated nucleic acid encoding an antibody as provided herein including embodiments thereof is provided. In embodiments, the nucleic acid includes the sequence of SEQ ID NO:18. In embodiments, the nucleic acid is the sequence of SEQ ID NO:18.

In another aspect, an isolated nucleic acid encoding a recombinant protein as provided herein, including embodiments thereof, is provided. In embodiments, the nucleic acid includes the sequence of SEQ ID NO:18.

Pharmaceutical Compositions

In an aspect is provided a pharmaceutical composition including a therapeutically effective amount of an antibody as provided herein including embodiments thereof and a pharmaceutically acceptable excipient.

In another aspect is provided a pharmaceutical composition including a therapeutically effective amount of a recombinant protein as provided herein, including embodiments thereof, and a pharmaceutically acceptable excipient.

Methods of Treatment

The compositions provided herein, including embodiments thereof, are contemplated as providing effective treatments for diseases such as cancer (e.g., leukemia [e.g., AML]). Thus, in an aspect is provided a method of treating cancer in a subject in need thereof, the method including administering to a subject a therapeutically effective amount of an antibody as provided herein including embodiments thereof, thereby treating cancer in the subject.

In another aspect is provided a method of treating cancer in a subject in need thereof, the method including administering to a subject a therapeutically effective amount of a recombinant protein as described herein, including embodiments thereof, thereby treating cancer in the subject. In embodiments, the cancer is leukemia. In embodiments, the cancer is acute myeloid leukemia. In embodiments, the cancer is chronic myeloid leukemia (CML). In embodiments, the cancer is lung cancer. In embodiments, the cancer is non-small cell lung cancer (NSCLC). In embodiments, the cancer is pancreatic cancer. In embodiments, the cancer is melanoma. In embodiments, the cancer is breast cancer. In embodiments, the cancer is colon cancer. In embodiments, the method further includes administering to the subject a second therapeutic agent.

In embodiments, the antibody is administered at an amount from about 0.01 nM to about 10 nM. In embodiments, the antibody is administered at an amount from about 0.05 nM to about 10 nM. In embodiments, the antibody is administered at an amount from about 0.1 nM to about 10 nM. In embodiments, the antibody is administered at an amount from about 0.5 nM to about 10 nM. In embodiments, the antibody is administered at an amount from about 1 nM to about 10 nM. In embodiments, the antibody is administered at an amount from about 2 nM to about 10 nM. In embodiments, the antibody is administered at an amount from about 4 nM to about 10 nM. In embodiments, the antibody is administered at an amount from about 6 nM to about 10 nM. In embodiments, the antibody is administered at an amount from about 4 nM to about 10 nM. In embodiments, the antibody is administered at an amount from about 8 nM to about 10 nM. In embodiments, the antibody is administered at an amount of about 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from 0.01 nM to 10 nM. In embodiments, the antibody is administered at an amount from 0.05 nM to 10 nM. In embodiments, the antibody is administered at an amount from 0.1 nM to 10 nM. In embodiments, the antibody is administered at an amount from 0.5 nM to 10 nM. In embodiments, the antibody is administered at an amount from 1 nM to 10 nM. In embodiments, the antibody is administered at an amount from 2 nM to 10 nM. In embodiments, the antibody is administered at an amount from 4 nM to 10 nM. In embodiments, the antibody is administered at an amount from 6 nM to 10 nM. In embodiments, the antibody is administered at an amount from 4 nM to 10 nM. In embodiments, the antibody is administered at an amount from 8 nM to 10 nM. In embodiments, the antibody is administered at an amount of 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from about 0.01 nM to about 8 nM. In embodiments, the antibody is administered at an amount from about 0.05 nM to about 8 nM. In embodiments, the antibody is administered at an amount from about 0.1 nM to about 8 nM. In embodiments, the antibody is administered at an amount from about 0.5 nM to about 8 nM. In embodiments, the antibody is administered at an amount from about 1 nM to about 8 nM. In embodiments, the antibody is administered at an amount from about 2 nM to about 8 nM. In embodiments, the antibody is administered at an amount from about 4 nM to about 8 nM. In embodiments, the antibody is administered at an amount from about 6 nM to about 8 nM. In embodiments, the antibody is administered at an amount from about 4 nM to about 8 nM.

In embodiments, the antibody is administered at an amount from 0.01 nM to 8 nM. In embodiments, the antibody is administered at an amount from 0.05 nM to 8 nM. In embodiments, the antibody is administered at an amount from 0.1 nM to 8 nM. In embodiments, the antibody is administered at an amount from 0.5 nM to 8 nM. In embodiments, the antibody is administered at an amount from 1 nM to 8 nM. In embodiments, the antibody is administered at an amount from 2 nM to 8 nM. In embodiments, the antibody is administered at an amount from 4 nM to 8 nM. In embodiments, the antibody is administered at an amount from 6 nM to 8 nM. In embodiments, the antibody is administered at an amount from 4 nM to 8 nM.

In embodiments, the antibody is administered at an amount from about 0.01 nM to about 6 nM. In embodiments, the antibody is administered at an amount from about 0.05 nM to about 6 nM. In embodiments, the antibody is administered at an amount from about 0.1 nM to about 6 nM. In embodiments, the antibody is administered at an amount from about 0.5 nM to about 8 nM. In embodiments, the antibody is administered at an amount from about 1 nM to about 6 nM. In embodiments, the antibody is administered at an amount from about 2 nM to about 6 nM. In embodiments, the antibody is administered at an amount from about 4 nM to about 6 nM.

In embodiments, the antibody is administered at an amount from 0.01 nM to 6 nM. In embodiments, the antibody is administered at an amount from 0.05 nM to 6 nM. In embodiments, the antibody is administered at an amount from 0.1 nM to 6 nM. In embodiments, the antibody is administered at an amount from 0.5 nM to 6 nM. In embodiments, the antibody is administered at an amount from 1 nM to 6 nM. In embodiments, the antibody is administered at an amount from 2 nM to 6 nM. In embodiments, the antibody is administered at an amount from 4 nM to 6 nM.

In embodiments, the antibody is administered at an amount from about 0.01 nM to about 4 nM. In embodiments, the antibody is administered at an amount from about 0.05 nM to about 4 nM. In embodiments, the antibody is administered at an amount from about 0.1 nM to about 4 nM. In embodiments, the antibody is administered at an amount from about 0.5 nM to about 4 nM. In embodiments, the antibody is administered at an amount from about 1 nM to about 4 nM. In embodiments, the antibody is administered at an amount from about 2 nM to about 4 nM.

In embodiments, the antibody is administered at an amount from 0.01 nM to 4 nM. In embodiments, the antibody is administered at an amount from 0.05 nM to 4 nM. In embodiments, the antibody is administered at an amount from 0.1 nM to 4 nM. In embodiments, the antibody is administered at an amount from 0.5 nM to 4 nM. In embodiments, the antibody is administered at an amount from 1 nM to 4 nM. In embodiments, the antibody is administered at an amount from 2 nM to 4 nM.

In embodiments, the antibody is administered at an amount from about 0.01 nM to about 2 nM. In embodiments, the antibody is administered at an amount from about 0.05 nM to about 2 nM. In embodiments, the antibody is administered at an amount from about 0.1 nM to about 2 nM. In embodiments, the antibody is administered at an amount from about 0.5 nM to about 2 nM. In embodiments, the antibody is administered at an amount from about 1 nM to about 2 nM.

In embodiments, the antibody is administered at an amount from 0.01 nM to 2 nM. In embodiments, the antibody is administered at an amount from 0.05 nM to 2 nM. In embodiments, the antibody is administered at an amount from 0.1 nM to 2 nM. In embodiments, the antibody is administered at an amount from 0.5 nM to 2 nM. In embodiments, the antibody is administered at an amount from 1 nM to 2 nM.

In embodiments, the antibody is administered at an amount from about 0.01 nM to about 1 nM. In embodiments, the antibody is administered at an amount from about 0.05 nM to about 1 nM. In embodiments, the antibody is administered at an amount from about 0.1 nM to about 1 nM. In embodiments, the antibody is administered at an amount from about 0.5 nM to about 1 nM.

In embodiments, the antibody is administered at an amount from 0.01 nM to 1 nM. In embodiments, the antibody is administered at an amount from 0.05 nM to 1 nM. In embodiments, the antibody is administered at an amount from 0.1 nM to 1 nM. In embodiments, the antibody is administered at an amount from 0.5 nM to 1 nM.

In embodiments, the antibody is administered at an amount of about 3.15 nM. In embodiments, the antibody is administered at an amount of 3.15 nM. In embodiments, the antibody is administered at an amount of about 1.05 nM. In embodiments, the antibody is administered at an amount of 1.05 nM.

It is understood that the recombinant protein (i.e., the bispecific antibody or the chimeric antigen receptor) provided herein including embodiments thereof may be administered at any of the concentrations described herein for the administration of the antibody (e.g., 0.01 nM-10 nM).

In embodiments, the antibody is administered at an amount from about 10 µg to about 500 µg. In embodiments, the antibody is administered at an amount from about 20 µg to about 500 µg. In embodiments, the antibody is administered at an amount from about 30 µg to about 500 µg. In embodiments, the antibody is administered at an amount from about 40 µg to about 500 µg. In embodiments, the antibody is administered at an amount from about 50 µg to about 500 µg. In embodiments, the antibody is administered at an amount from about 60 µg to about 500 µg. In embodiments, the antibody is administered at an amount from about 70 µg to about 500 µg. In embodiments, the antibody is administered at an amount from about 80 µg to about 500 µg. In embodiments, the antibody is administered at an amount from about 90 µg to about 500 µg. In embodiments, the antibody is administered at an amount from about 100 µg to about 500 µg.

In embodiments, the antibody is administered at an amount from about 110 µg to about 500 µg. In embodiments, the antibody is administered at an amount from about 120 µg to about 500 µg. In embodiments, the antibody is administered at an amount from about 130 µg to about 500 µg. In embodiments, the antibody is administered at an amount from about 140 µg to about 500 µg. In embodiments, the antibody is administered at an amount from about 150 µg to about 500 µg. In embodiments, the antibody is administered at an amount from about 160 µg to about 500 µg. In embodiments, the antibody is administered at an amount from about 170 µg to about 500 µg. In embodiments, the antibody is administered at an amount from about 180 µg to about 500 µg. In embodiments, the antibody is administered at an amount from about 190 µg to about 500 µg. In embodiments, the antibody is administered at an amount from about 200 µg to about 500 µg.

In embodiments, the antibody is administered at an amount from about 210 µg to about 500 µg. In embodiments, the antibody is administered at an amount from about 220 µg to about 500 µg. In embodiments, the antibody is administered at an amount from about 230 µg to about 500 µg. In embodiments, the antibody is administered at an amount from about 240 µg to about 500 µg. In embodiments, the antibody is administered at an amount from about 250 µg to about 500 µg. In embodiments, the antibody is administered at an amount from about 260 µg to about 500 µg. In embodiments, the antibody is administered at an amount from about 270 µg to about 500 µg. In embodiments, the antibody is administered at an amount from about 280 µg to about 500 µg. In embodiments, the antibody is administered at an amount from about 290 µg to about 500 µg. In embodiments, the antibody is administered at an amount from about 300 µg to about 500 µg.

In embodiments, the antibody is administered at an amount from about 310 µg to about 500 µg. In embodiments, the antibody is administered at an amount from about 320 µg to about 500 µg. In embodiments, the antibody is administered at an amount from about 330 µg to about 500 µg. In embodiments, the antibody is administered at an amount from about 340 µg to about 500 µg. In embodiments, the antibody is administered at an amount from about 350 µg to about 500 µg. In embodiments, the antibody is administered at an amount from about 360 µg to about 500 µg. In embodiments, the antibody is administered at an amount from about 370 µg to about 500 µg. In embodiments, the antibody is administered at an amount from about 380 µg to about 500 µg. In embodiments, the antibody is administered at an amount from about 390 µg to about 500 µg. In embodiments, the antibody is administered at an amount from about 400 µg to about 500 µg.

In embodiments, the antibody is administered at an amount from about 410 µg to about 500 µg. In embodiments, the antibody is administered at an amount from about 420 µg to about 500 µg. In embodiments, the antibody is administered at an amount from about 430 µg to about 500 µg. In embodiments, the antibody is administered at an amount from about 440 µg to about 500 µg. In embodiments, the antibody is administered at an amount from about 450 µg to about 500 µg. In embodiments, the antibody is administered at an amount from about 460 µg to about 500 µg. In embodiments, the antibody is administered at an amount from about 470 µg to about 500 µg. In embodiments, the antibody is administered at an amount from about 480 µg to about 500 µg. In embodiments, the antibody is administered at an amount from about 490 µg to about 500 µg.

In embodiments, the antibody is administered at an amount from about 10 µg to about 400 µg. In embodiments, the antibody is administered at an amount from about 20 µg to about 400 µg. In embodiments, the antibody is administered at an amount from about 30 µg to about 400 µg. In embodiments, the antibody is administered at an amount from about 40 µg to about 400 µg. In embodiments, the antibody is administered at an amount from about 50 µg to about 400 µg. In embodiments, the antibody is administered at an amount from about 60 µg to about 400 µg. In embodiments, the antibody is administered at an amount from about 70 µg to about 400 µg. In embodiments, the antibody is administered at an amount from about 80 µg to about 400 µg. In embodiments, the antibody is administered at an amount from about 90 µg to about 400 µg. In embodiments, the antibody is administered at an amount from about 100 µg to about 400 µg.

In embodiments, the antibody is administered at an amount from about 10 µg to about 300 µg. In embodiments, the antibody is administered at an amount from about 20 µg to about 300 µg. In embodiments, the antibody is administered at an amount from about 30 µg to about 300 µg. In embodiments, the antibody is administered at an amount from about 40 µg to about 300 µg. In embodiments, the antibody is administered at an amount from about 50 µg to about 300 µg. In embodiments, the antibody is administered at an amount from about 60 µg to about 300 µg. In embodiments, the antibody is administered at an amount from about 70 µg to about 300 µg. In embodiments, the antibody is administered at an amount from about 80 µg to about 300 µg. In embodiments, the antibody is administered at an amount from about 90 µg to about 300 µg. In embodiments, the antibody is administered at an amount from about 100 µg to about 300 µg.

In embodiments, the antibody is administered at an amount from about 10 µg to about 200 µg. In embodiments, the antibody is administered at an amount from about 20 µg to about 200 µg. In embodiments, the antibody is administered at an amount from about 30 µg to about 200 µg. In embodiments, the antibody is administered at an amount from about 40 µg to about 200 µg. In embodiments, the antibody is administered at an amount from about 50 µg to about 200 µg. In embodiments, the antibody is administered at an amount from about 60 µg to about 200 µg. In embodiments, the antibody is administered at an amount from about 70 µg to about 200 µg. In embodiments, the antibody is administered at an amount from about 80 µg to about 200 µg. In embodiments, the antibody is administered at an amount from about 90 µg to about 200 µg. In embodiments, the antibody is administered at an amount from about 100 µg to about 200 µg.

In embodiments, the antibody is administered at an amount from about 10 µg to about 100 µg. In embodiments, the antibody is administered at an amount from about 20 µg to about 100 µg. In embodiments, the antibody is administered at an amount from about 30 µg to about 100 µg. In embodiments, the antibody is administered at an amount from about 40 µg to about 100 µg. In embodiments, the antibody is administered at an amount from about 50 µg to about 100 µg. In embodiments, the antibody is administered at an amount from about 60 µg to about 100 µg. In embodiments, the antibody is administered at an amount from about 70 µg to about 100 µg. In embodiments, the antibody is administered at an amount from about 80 µg to about 100 µg. In embodiments, the antibody is administered at an amount from about 90 µg to about 100 µg.

In embodiments, the antibody is administered at an amount of about 10 µg, 20 µg, 30 µg, 40 µg, 50 µg, 60 µg, 70 µg, 80 µg, 90 µg, 100 µg, 110 µg, 120 µg, 130 µg, 140 µg, 150 µg, 160 µg, 170 µg, 180 µg, 190 µg 200 µg, 210 µg, 220 µg, 230 µg, 240 µg, 250 µg, 260 µg, 270 µg, 280 µg, 290 µg, 300 µg 310 µg, 320 µg, 330 µg, 340 µg, 350 µg, 360 µg, 370 µg, 380 µg, 390 µg, 400 µg, 410 µg, 420 µg, 430 µg, 440 µg, 450 µg, 460 µg, 470 µg, 480 µg, 490 µg or 500 µg.

In embodiments, the antibody is administered at an amount of 10 µg, 20 µg, 30 µg, 40 µg, 50 µg, 60 µg, 70 µg, 80 µg 90 µg, 100 µg, 110 µg, 120 µg, 130 µg, 140 µg, 150 µg, 160 µg, 170 µg, 180 µg, 190 µg, 200 µg 210 µg, 220 µg, 230 µg, 240 µg, 250 µg, 260 µg, 270 µg, 280 µg, 290 µg, 300 µg, 310 µg, 320 µg, 330 µg, 340 µg, 350 µg, 360 µg, 370 µg, 380 µg, 390 µg 400 µg, 410 µg, 420 µg, 430 µg, 440 µg, 450 µg, 460 µg, 470 µg, 480 µg, 490 µg, or 500 µg.

It is understood that the recombinant protein (i.e., the bispecific antibody or the chimeric antigen receptor) provided herein including embodiments thereof may be administered at any of the concentrations described herein for the administration of the antibody (e.g., 10 µg-500 µg).

In embodiments, the recombinant protein or antibody is administered at an amount of about 200 µg. In embodiments, the recombinant protein or antibody is administered at an amount of 200 µg.

Methods of Inhibiting Cell Proliferation

The compositions provided herein, including embodiments thereof, are further contemplated for inhibiting cell proliferation. Thus, in an aspect is provided a method of inhibiting proliferation of a cell, the method including: (i) contacting a cell with an anti-IL1RAP antibody as provided herein including embodiments thereof, or a recombinant protein as provided herein including embodiments thereof, thereby forming a contacted cell; and (ii) allowing the anti-IL1RAP antibody, the recombinant protein as provided herein including embodiments thereof to bind an IL1RAP on the contacted cell, thereby inhibiting proliferation of the cell. In embodiments, the cell is a cancer cell. In embodiments, the cell is a leukemia stem cell (LSC). In embodiments, the cancer cell is an acute myeloid leukemia (AML) cell. In embodiments, the cancer cell is a chronic myeloid leukemia (CML) cell. In embodiments, the cancer cell is a lung cancer cell. In embodiments, the cancer cell is a non-small cell lung cancer (NSCLC) cell. In embodiments, the cancer cell is a pancreatic cancer cell. In embodiments, the cancer cell is a melanoma cell. In embodiments, the cancer cell is a breast cancer cell. In embodiments, the cancer cell is a colon cancer cell.

EXAMPLES

The following examples are offered to illustrate, but not to limit the claimed invention.

Example 1

Acute myeloid leukemia (AML) is associated with a poor survival rate, and there is an urgent need for novel and more efficient therapies ideally targeting AML stem cells that are essential for maintaining the disease. Applicants' lab and other publications reported that IL1RAP protein is upregulated on candidate leukemic stem cells in the majority of AML patients, but not on normal hematopoietic stem cells.

Applicants developed a new human monoclonal antibody (1D5) that can bind IL1RAP on AML cells and applied this antibody for bispecific antibody (anti-CD3x IL1RAP) and CAR-T techniques. Applicants' study showed that the bispecific antibody can efficiently kill all AML cell lines tested and ten-patient AML sample as well. The in vivo study also demonstrates its therapeutic potency.

Both the in vitro and in vivo experimental results show that the antibody possesses great potential for treating AML disease in the clinic.

Applicants screened a monoclonal antibody (1D5) from their human naïve phage display antibody library against IL1RAP protein which is reported to be upregulated in Acute Myeloid Leukemia (AML) cells. This antibody showed affinity of around 20 nM to recombinant IL1RAP protein.

Using this monoclonal antibody (1D5), Applicants then synthesized a bispecific antibody. The bispecific antibody consists of two arms: one is CD3 antibody, and the other one is the monoclonal antibody 1D5. This bispecific antibody binds to cells that express IL1RAP protein, and then helps to recruit T cell to the IL1RAP-expressing cells and kills the cells. Applicants next tested the binding of this antibody to seven different AML cell lines. After confirmation of the binding of this antibody to all AML cells lines tested, Applicants tried a specific killing assay with all 7 AML cell lines and 10 AML patient samples. The killing assay showed over 90% of specific killing for both AML cell lines and AML patient sample.

Applicants' in vivo study also demonstrated that by infusing this bispecific antibody in mice that are engrafted with MV4-11 cell line together with human T cells, the MV4-11 cells are eliminated compared to the control group.

This bispecific antibody can be further developed for the treatment of AML. The monoclonal antibody 1D5 is now used for CAR-T which is another powerful approach to treat AML.

Example 2

Immunotherapeutic targeting of IL1RAP to eliminate leukemia stem cells (LSC) in Acute Myeloid Leukemia (AML).

Abstract. AML is a devastating hematopoietic malignancy, resulting in progressive accumulation of primitive and partially differentiated clonal blasts and rapidly leads to hematopoiesis failure and death if left untreated. Despite increasing knowledge of the molecular mechanisms of leukemogenesis, implementation of risk-stratification strategies for treatment guidance and use of molecular targeting therapeutics, only a minority of AML patients are cured with current chemotherapy regimens while the majority of them are either immediately refractory to induction therapy or subsequently relapse following transient complete remission. The current view is that treatment resistance and relapse in AML is due to the inability of chemotherapy and/or other molecular targeting therapeutics to eliminate the so-called leukemia stem cells (LSC). These clonal primitive cells are at the hierarchical apex of leukemogenesis and have stem cell properties to maintain clonal expansion indefinitely. Applicants' goal is to develop novel therapies that can effectively eradicate LSC and improve cure rates in AML patients, while sparing normal hematopoietic stem cells (HSC).

Allogeneic hematopoietic cell transplantation (alloHCT) has been successfully applied in AML patients and has provided the proof of concept that a normally functioning (donor) immune system can target and eliminate LSC. However, because intrinsic toxicity and transplant-related mortality, alloHCT can be performed only in subsets of AML patients. More recently, other immunotherapeutic approaches, such as naked, conjugated or T cell engaged bispecific monoclonal antibodies (BsAb) recruiting T or NK cells or chimeric antigen receptor (CAR) engineered T cells, have been shown to be a feasible and effective treatment approach in cancer and leukemia with relatively minor toxicity. BsAb or CAR T cells redirect the immune system to specific antigen targets expressed on the surface of cancer or leukemia cells, thereby enhancing immune-mediated specific killing of malignant cells. Here Applicants propose to select novel membrane antigens that are specifically enriched on AML LSC (compared to normal HSC) and target them using T cell engaged BsAb and/or CAR T-cells. Recently Applicants have focused on Interleukin-1 receptor accessory protein (IL1RAP). Overactivation of innate immune components such as TLRs, IRAK/TRAF6, IL8/CXCR2 and IL1 signaling pathways has been demonstrated in LSC. IL1RAP is a coreceptor of IL1 receptor. Applicants have shown that IL1RAP is selectively unregulated on chronic myeloid leukemia (CML) LSC compared to normal HSC, and blocking IL-1 signaling with IL-1 receptor antagonist (IL-1RA) inhibited leukemia growth, while preserving normal hematopoiesis. Applicants found that IL1RAP is also over-expressed on the surface of human AML CD34$^+$ blasts compared with normal CD34$^+$ cells, and others have shown that high IL1RAP expression is associated with poor overall survival in AML. Altogether, these data suggest that IL1RAP is an ideal target for targeting LSC.

Applicants have utilized a human naïve phage display library made from 10 healthy donors to develop functional IL1RAP monoclonal and T cell engaged BsAb and CAR-T cells. Preliminary data indicated that the construct based on IL1RAP epitopes derived from the aforementioned human naïve phage display library can be utilized to produce high affinity BsAb and CAR-T cells. As proof of principle, Applicants showed specific killing of both AML cell lines and primary AML patient leukemia blasts in the T cell Dependent Cellular Cytotoxicity (TDCC) assay in the presence of anti-IL1RAPxCD3 BsAb in vitro, and disease elimination in immunodeficient mice engrafted with MV4-11 AML cells and treated with both BsAb and human T-cells in vivo.

Thus, Applicants have a novel construct to produce immunotherapeutics targeting IL1RAP on AML LSC. Applicants will optimize the therapeutic efficacy, dose and schedule of anti-IL1RAPxCD3 BsAb to target LSC in AML, develop IL1RAP CAR-T cells to eradicate human AML LSC and determine clinical applicability, and enhance anti-leukemic activity of IL1RAP-based immunotherapeutics using immunocheckpoint inhibitors. For these experiments, Applicants will utilize multiple AML mouse models and sequential transplants of primary AML blasts in immunodeficient mice to functionally demonstrate elimination of LSC.

Background Acute myeloid leukemia (AML) is a devastating hematopoietic malignancy, resulting in progressive accumulation of primitive and partially-differentiated clonal blasts, a condition rapidly leading to hematopoiesis failure and death if untreated [1]. AML blasts are characterized by specific molecular profiles in individual patients, including cytogenetic aberrations, gene mutations, aberrant coding and non-coding gene RNA levels and epigenetic changes. This heterogeneity is clinically relevant and has been used to select the most appropriate risk-adapted treatments. However, despite increasing knowledge of molecular mechanisms of leukemogenesis and implementation of risk-stratification treatment strategies, only a minority of the AML patients are cured, while the vast majority of them are either immediately refractory to chemotherapy or relapse following transient achievement of complete remission[2, 3]. The inability of chemotherapy and/or other molecular targeting therapeutics to cure AML is likely due to persistence of the so-called leukemia stem cells (LSC). These clonal primitive cells are at the hierarchical apex of the leukemogenic process and have stem cell properties that maintain clonal expansion indefinitely. Thus, Applicants' goal is to develop novel therapies that effectively eradicate LSC and improve cure rates in AML patients, while sparing normal hematopoietic stem cells (HSC). Allogeneic hematopoietic cell transplantation (alloHCT) has been successfully applied to AML patients and has provided the proof of concept that a normally functioning (donor) immune system can target and eliminate LSC [4, 5]. However, because of transplant-related toxicity and mortality, alloHCT is feasible only in subsets of AML patients. More recently, therapies that harness the immune system like naked, conjugated or T cell-engaged bispecific monoclonal antibodies (BsAb), immunocheckpoint inhibitors or chimeric antigen receptor (CAR) engineered T cells have been shown to be feasible and effective in advanced human malignancies, including solid tumors, lymphomas and acute leukemias. Of these approaches, BsAb or CAR-T cells are both based on the principle of redirecting the immune system to specific antigen targets on cancer cells with little toxicity [6, 7]. Applicants propose to select novel membrane antigens specifically enriched on AML LSC (compared to normal HSC) and target them using BsAb and/or CAR-T cells. Recently, Applicants have focused on Interleukin-1 receptor accessory protein (IL1RAP), an IL1R co-receptor, given that overactivation of innate immune components such as TLRs, IRAK/TRAF6, IL8/CXCR2 and IL1 signaling pathways is reportedly essential for LSC homeostasis. Applicants also found that IL1RAP is over-expressed on the surface of human AML CD34$^+$ blasts compared with normal CD34$^+$ cells. Similar results were reported by Barreyo et al which show that high levels of IL1RAP protein are expressed on the surface of HSC from patients with AML and high-risk myelodysplastic syndrome, and are associated with poor overall survival [9].

Methods.

Figure 1B:
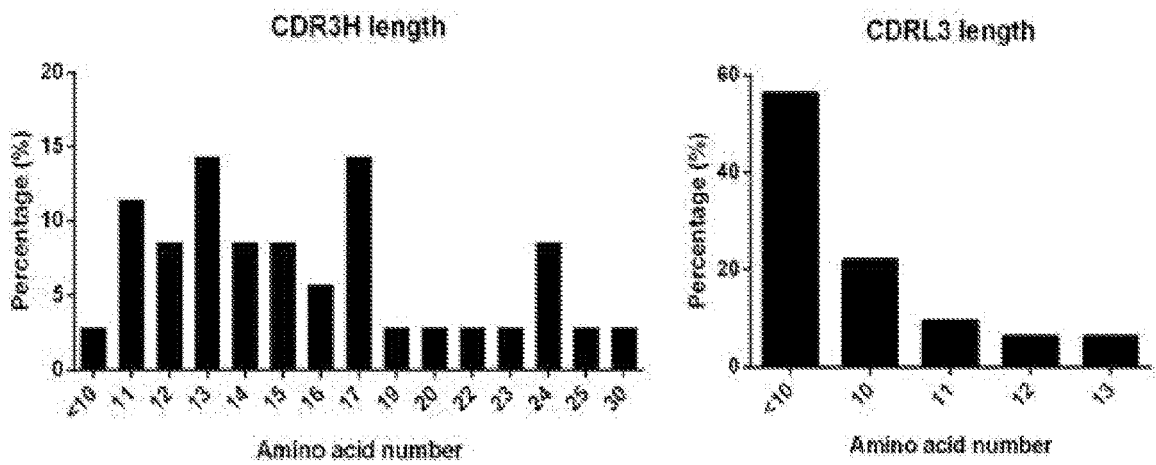
Figure 1C:
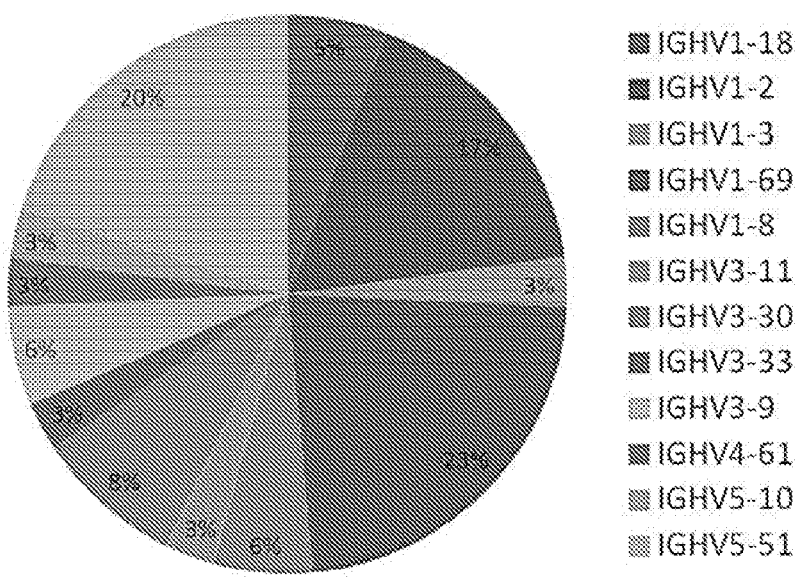
Figure 1C:
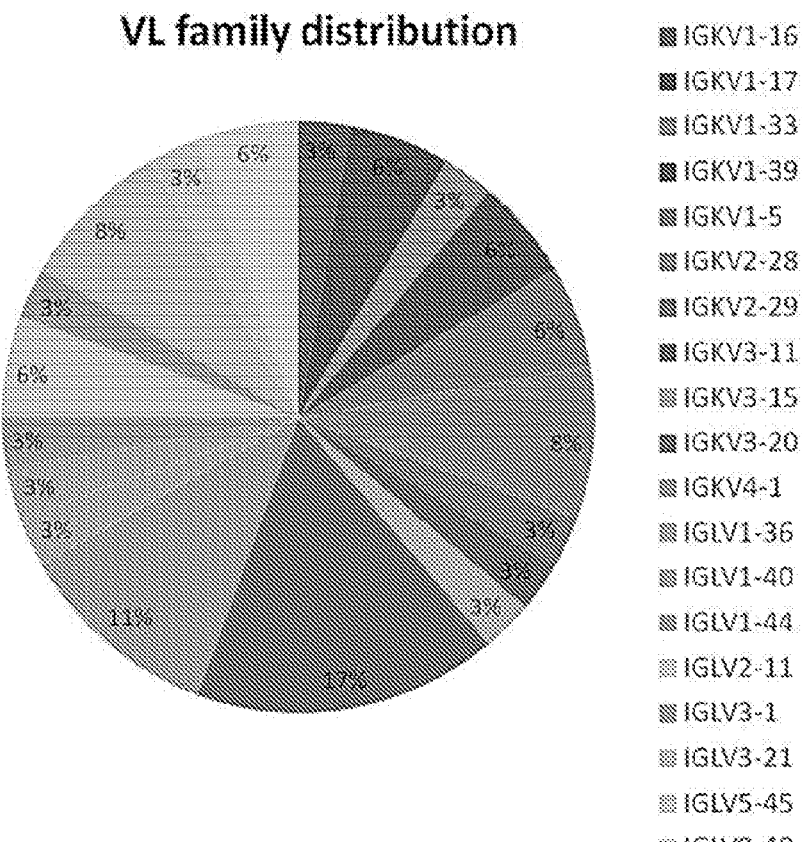
Figure 2A:
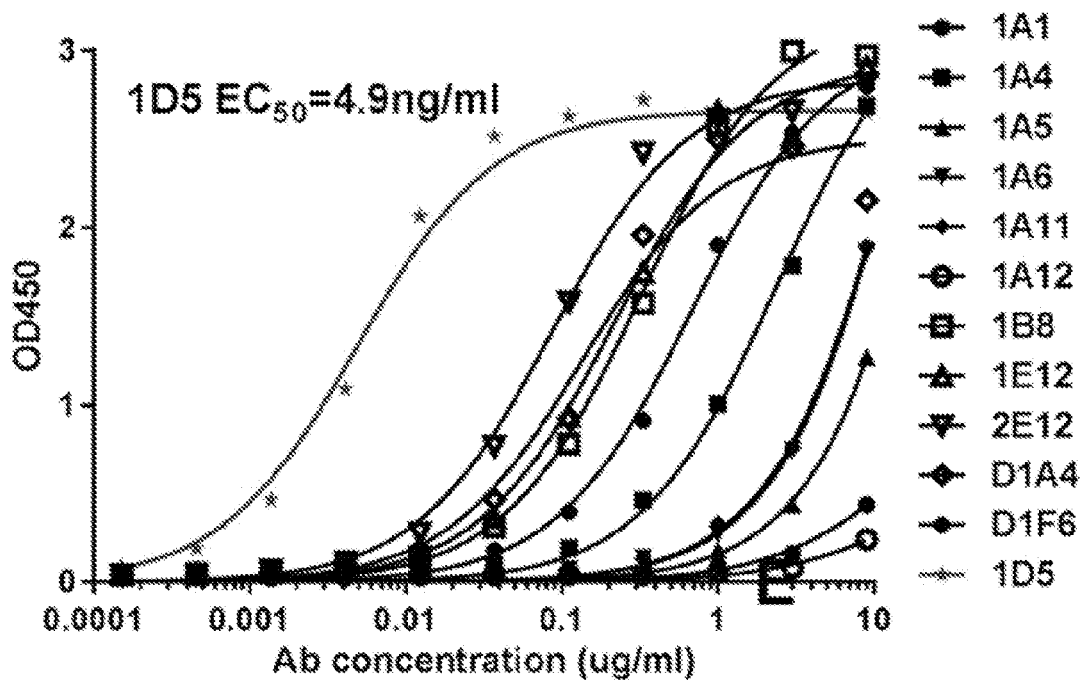
FIGS. 2A-2D. Anti-IL1RAP monoclonal antibodies selected from human naïve phage display library. The screening/sequencing process yielded 12 unique antibody sequences. Thus Applicants selected the 12 positive clones from their phage display library and the genes encoding heavy and light chains of these antibodies from these clones were cloned to IgG expression vectors for transient expression in expi293 cells. Antibodies were purified by protein A resin for functional study.
Figure 2B:
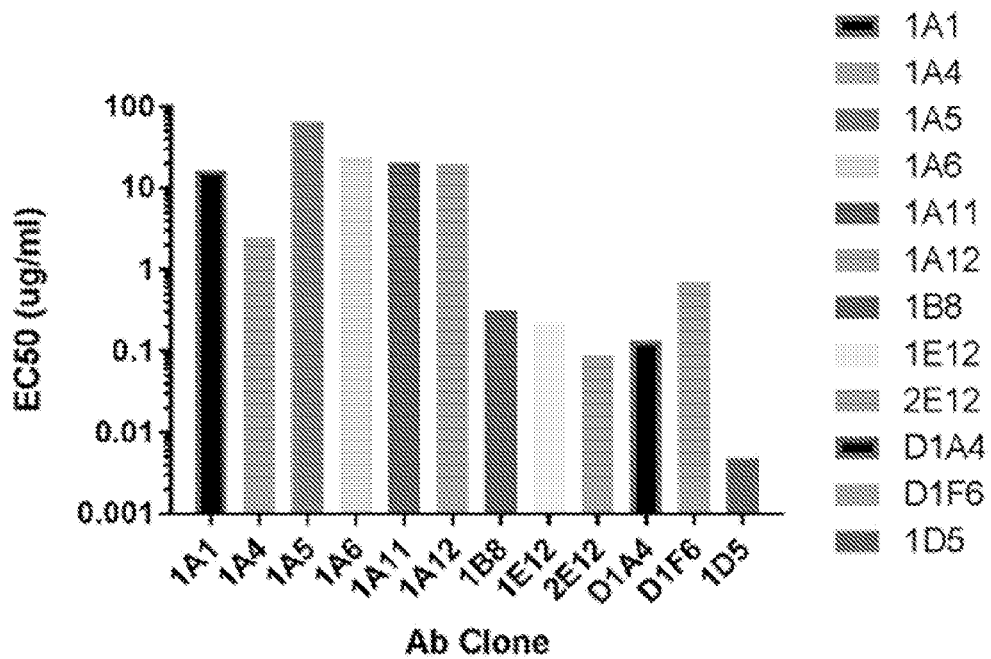
Figure 2C:
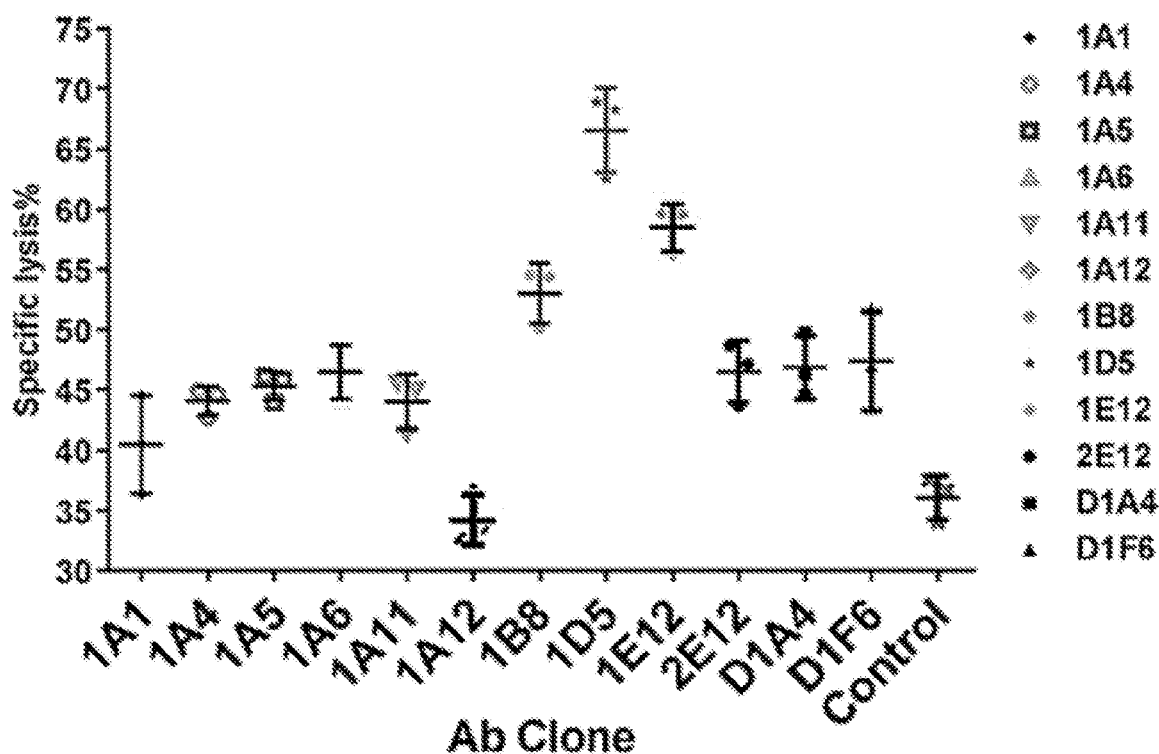
Figure 2D:
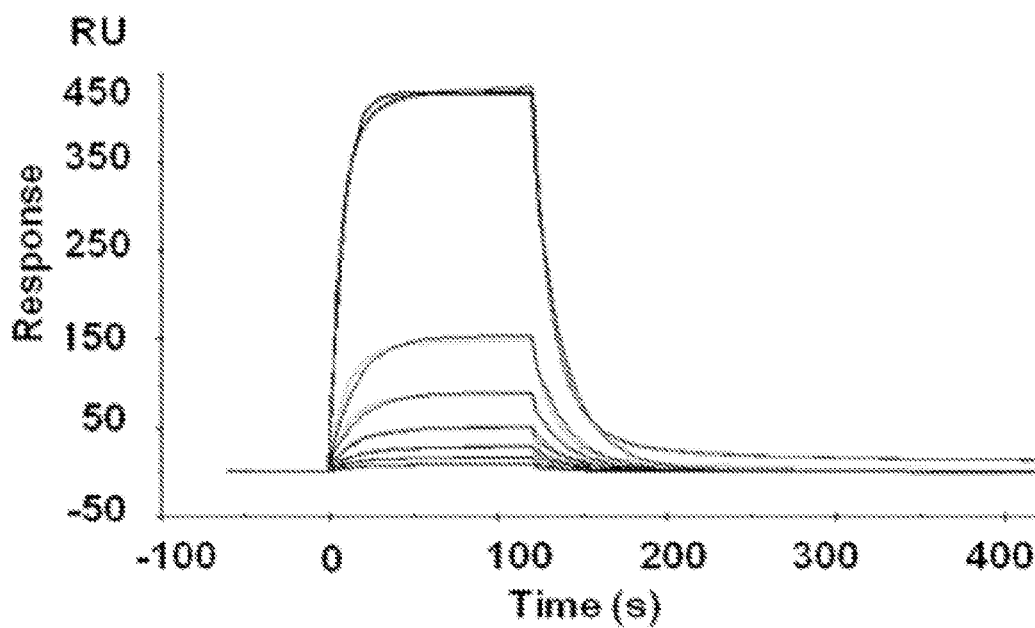
Figure 3A:
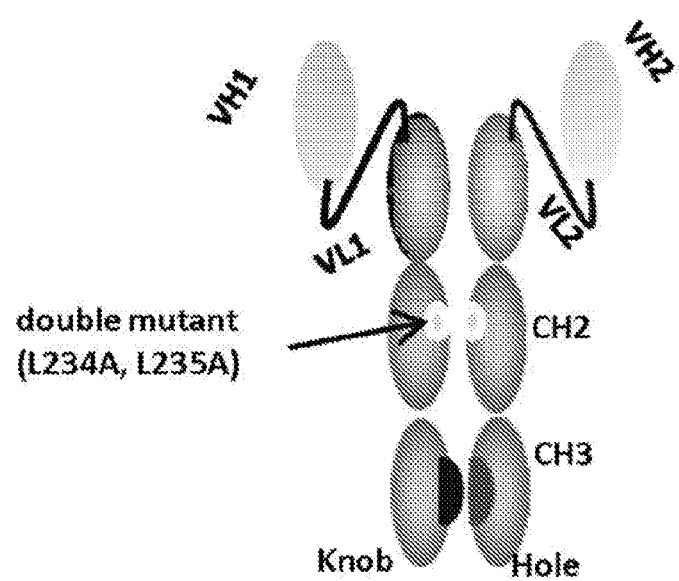
FIGS. 3A-3C. Anti-CD3XIL1RAP bispecific antibody.
Figure 3B:
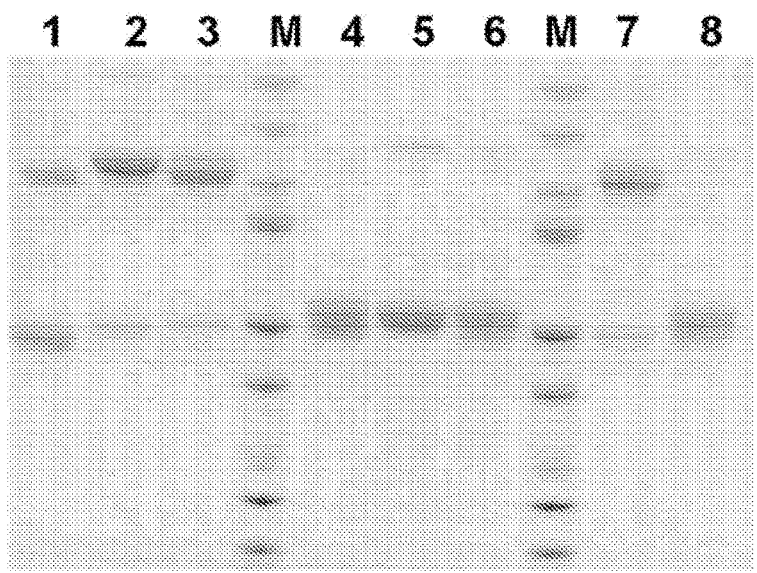
Figure 3C:
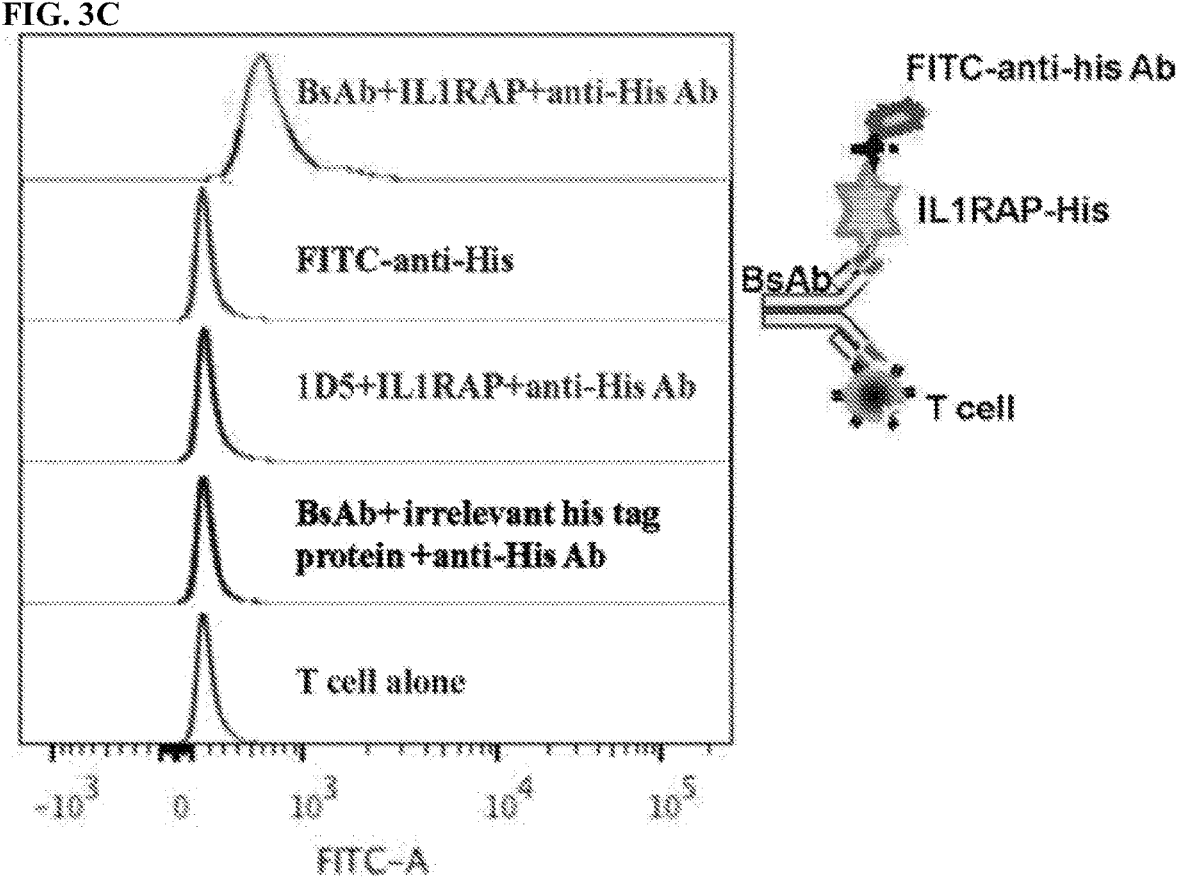
Figure 7A:
FIGS. 7A-7B. Jurkat cells transduced with IL1RAP CAR can be activated when cocultured with AML cell lines.
Figure 7B:
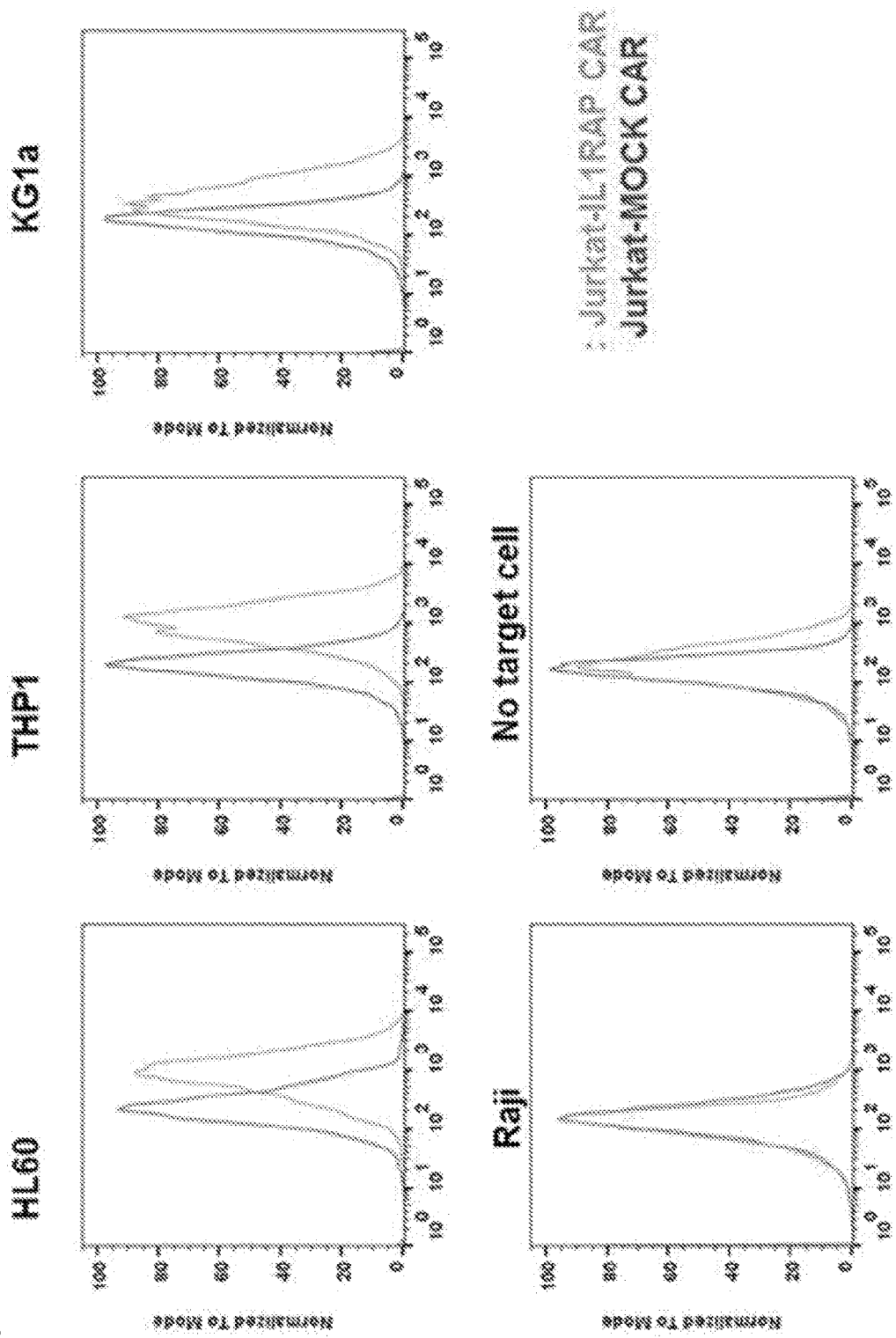
Figure 8A:
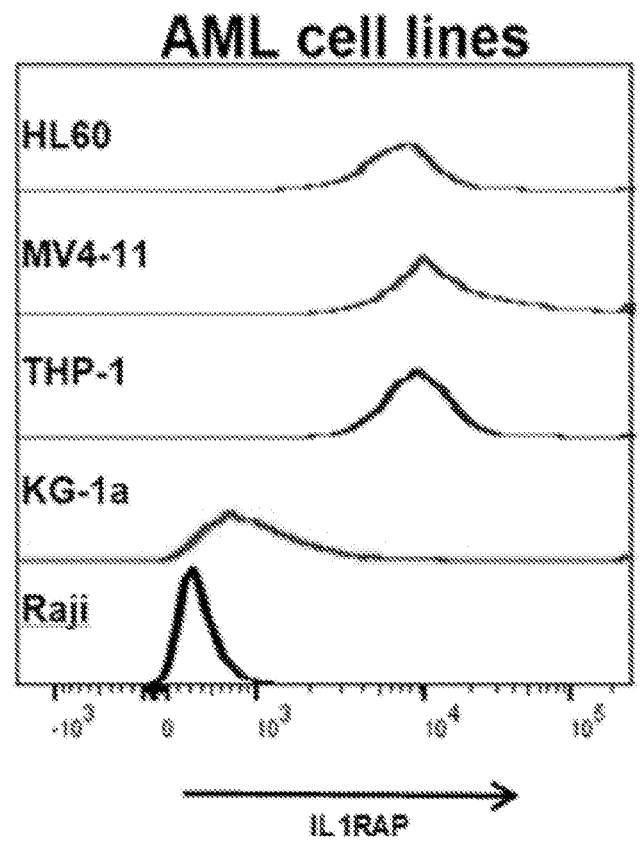
FIGS. 8A-8I. IL1RAP as an immunotherapy target for AML. ILRAP expression was detected by flow cytometry on AML cell lines (FIG. 8A) and CD34 enriched AML primary cells (FIG. 8B) but not on CD34+ enriched normal bone marrow cells (FIG. 8C).
Figure 8B:
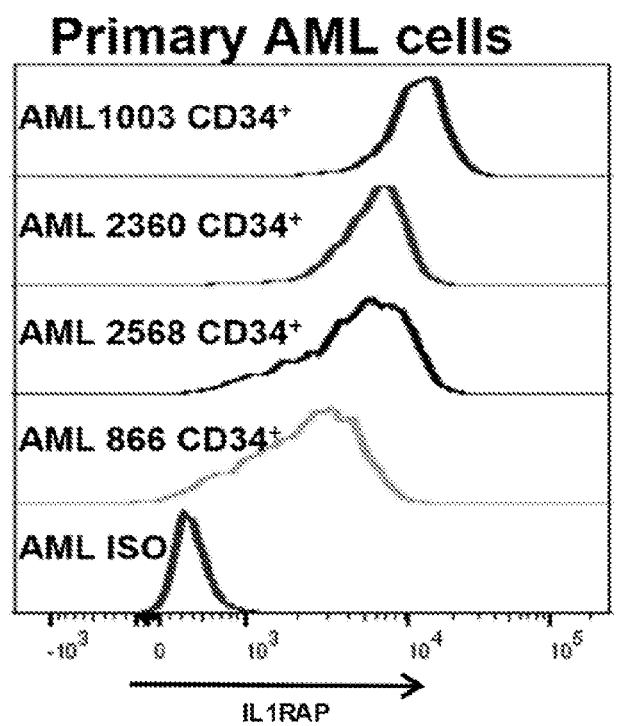
Figure 8C:
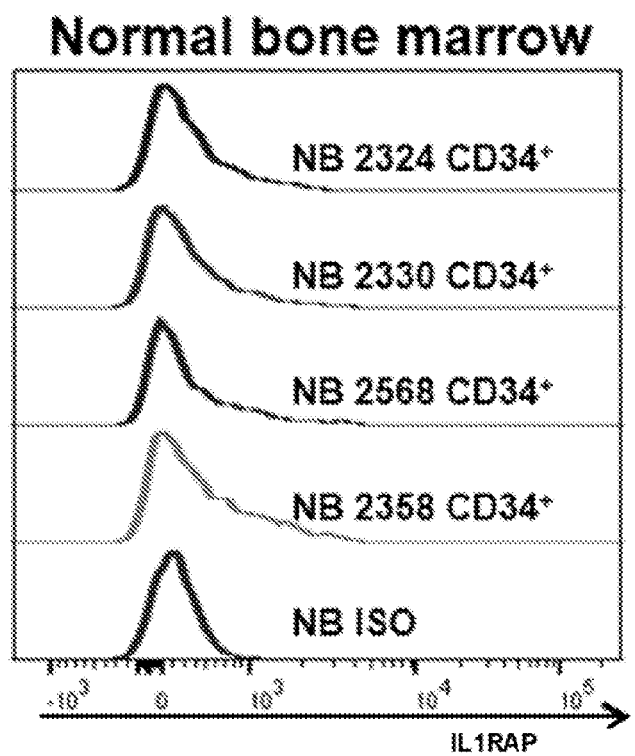
Figure 8D:
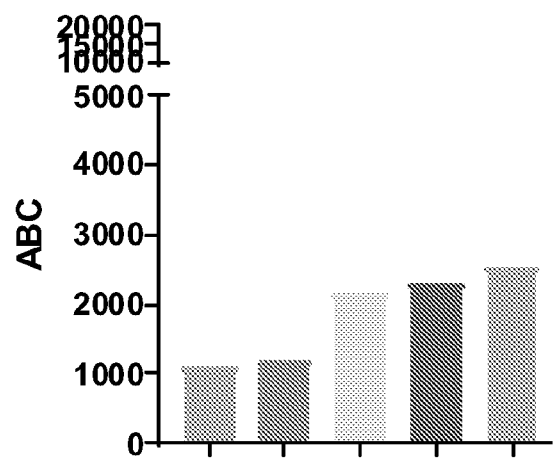
Figure 8E:
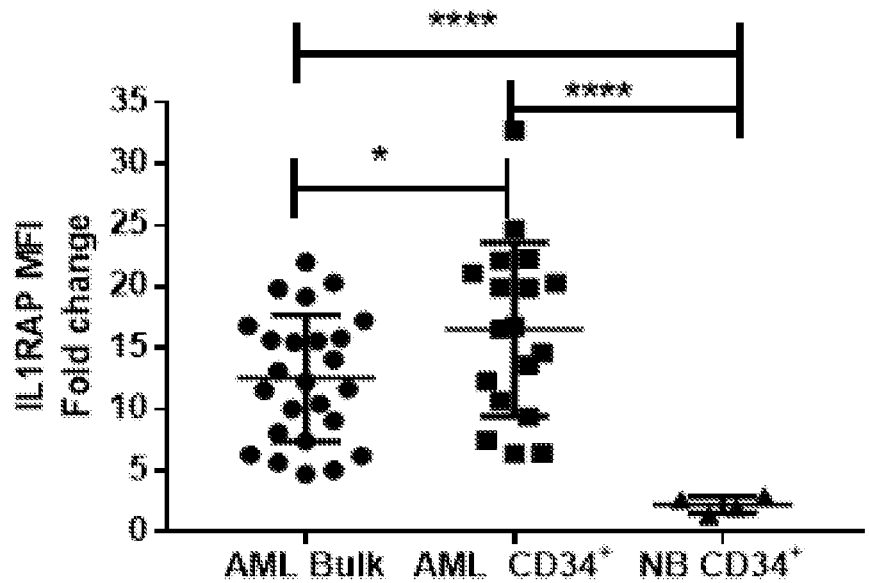
Figure 8F:
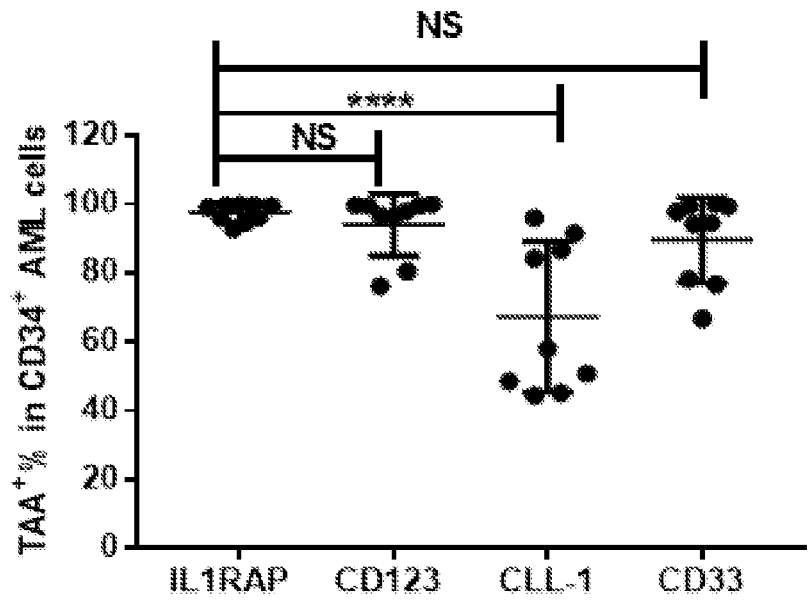
Figure 8G:
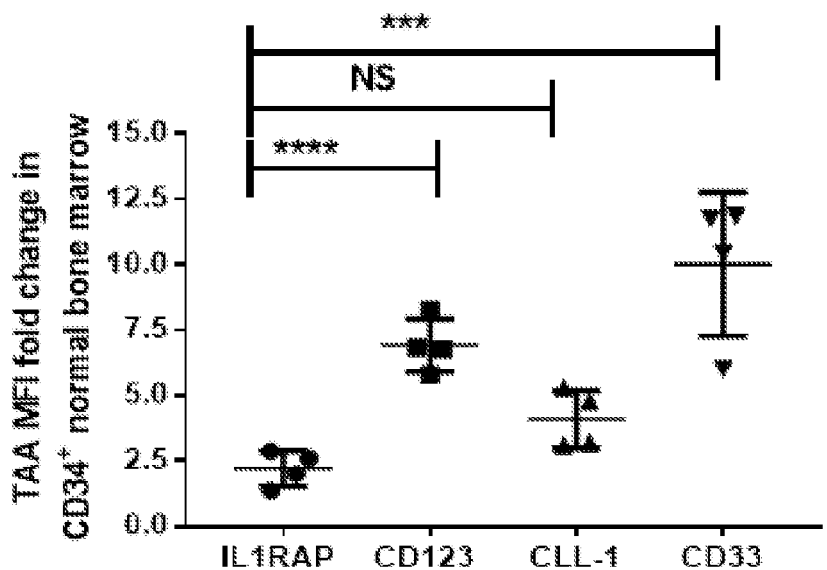
Figure 8H:
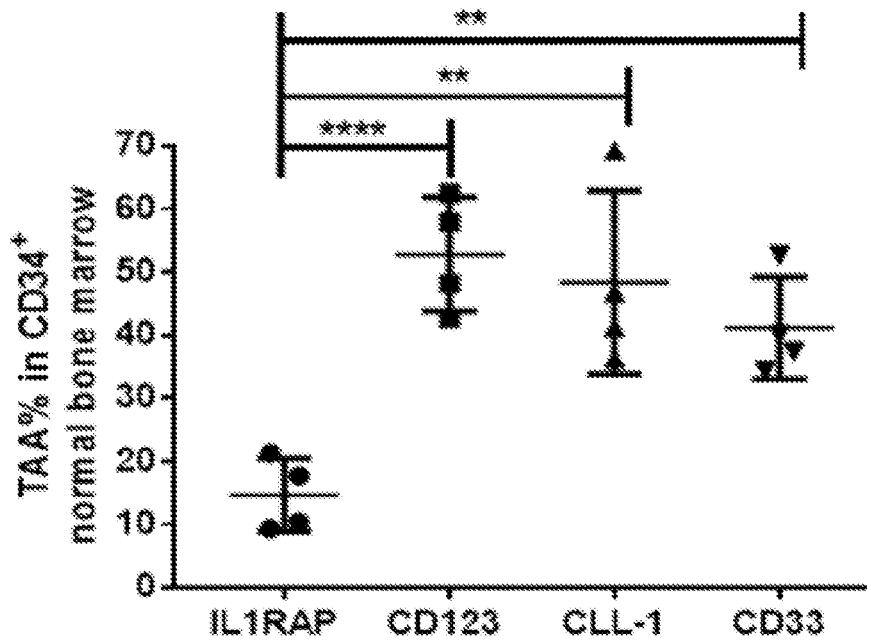
Figure 8I:
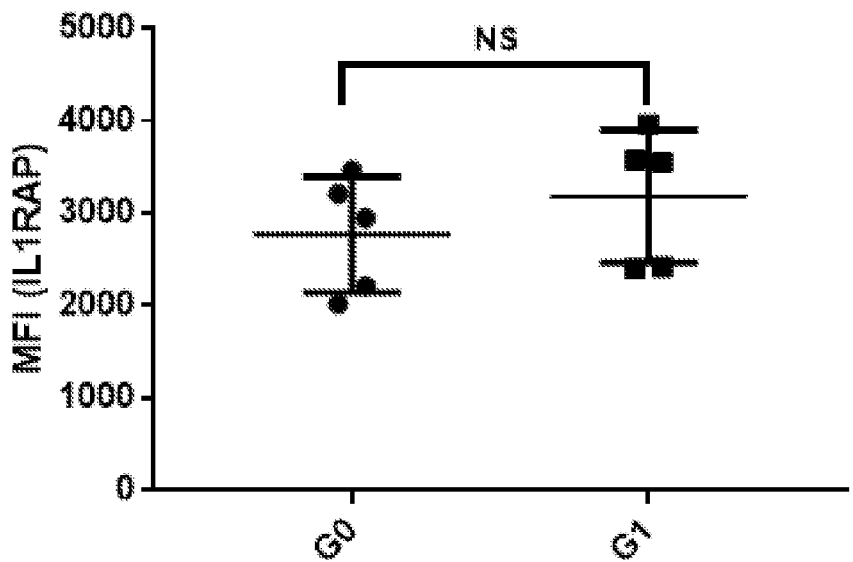
Figure 9A:
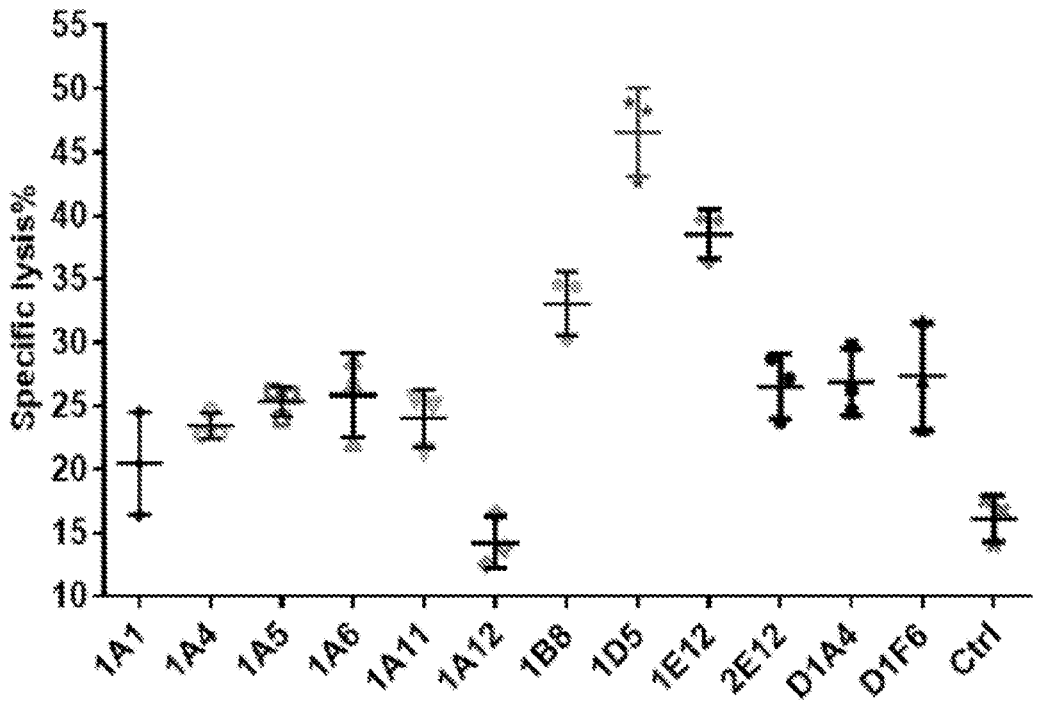
FIGS. 9A-9B. Anti-IL1RAP/CD3 bispecific antibody.
Figure 9B:
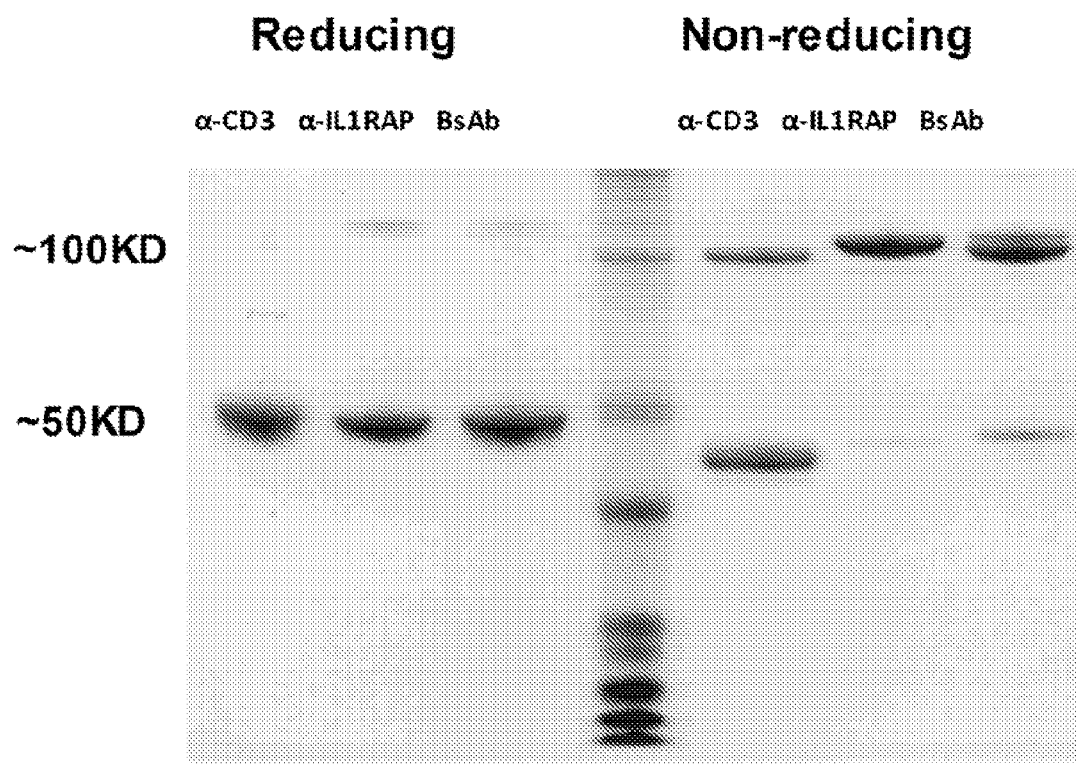
Figure 10A:
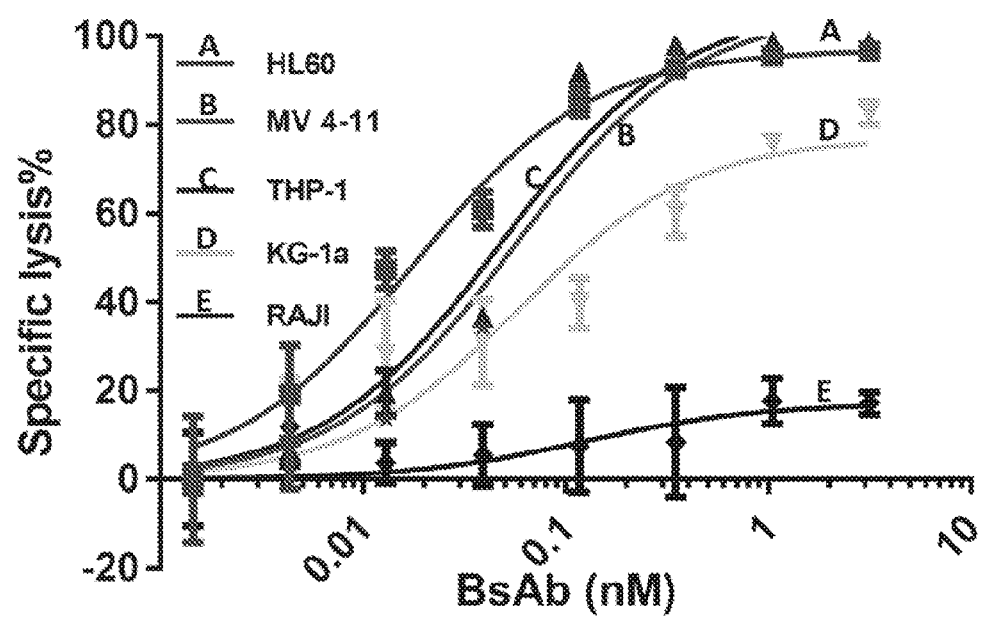
FIGS. 10A-10K. MM001 (CD3/IL1RAP bispecific antibody) induced T cell activation and AML cell killing at different concentration and E: T ratio.
Figure 10B:
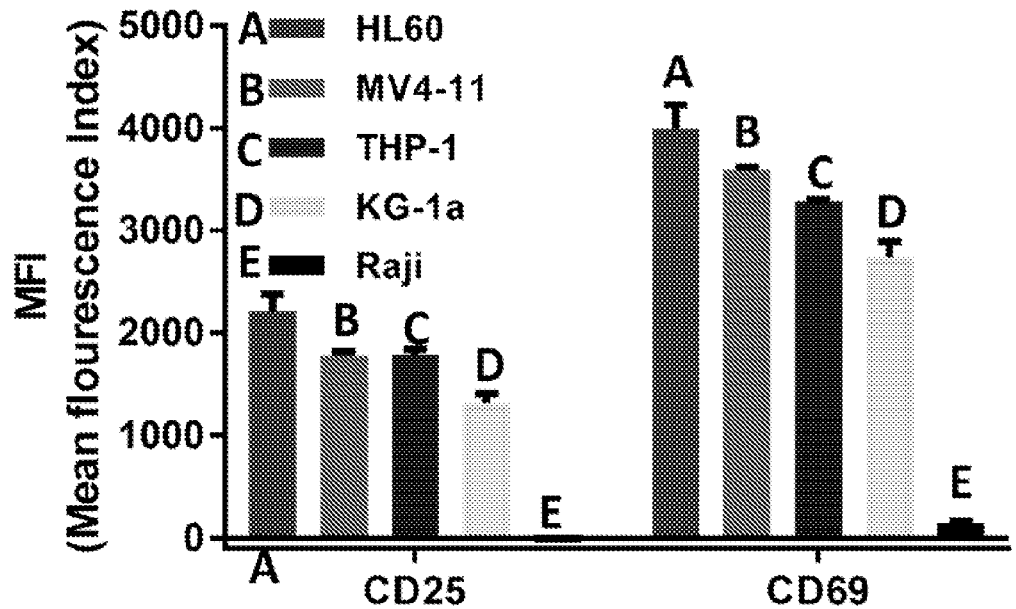
Figure 10C:
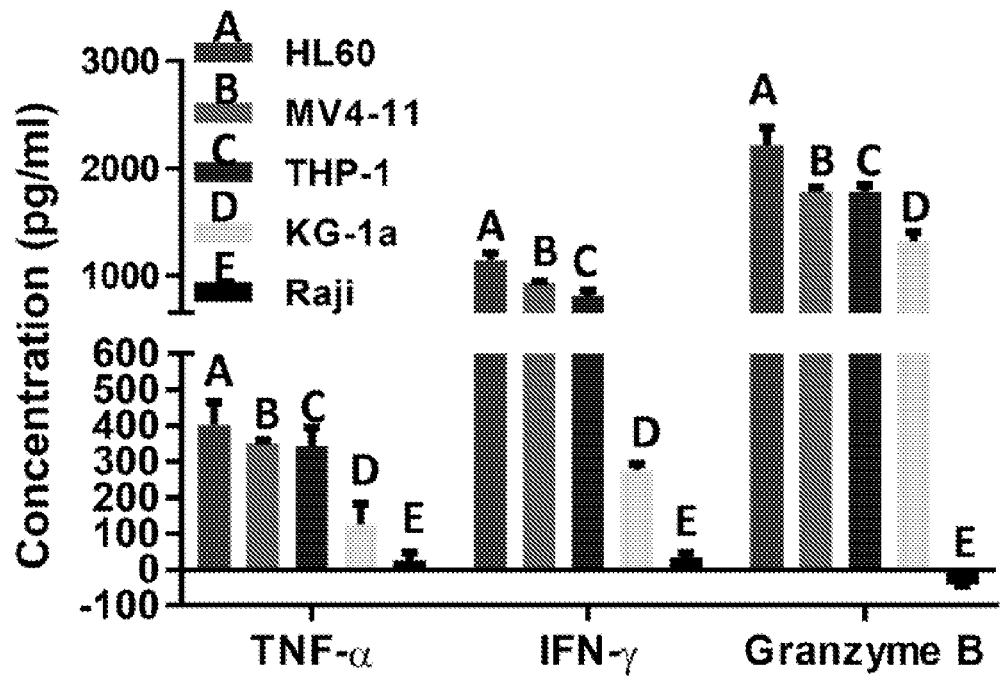
Figure 10D:
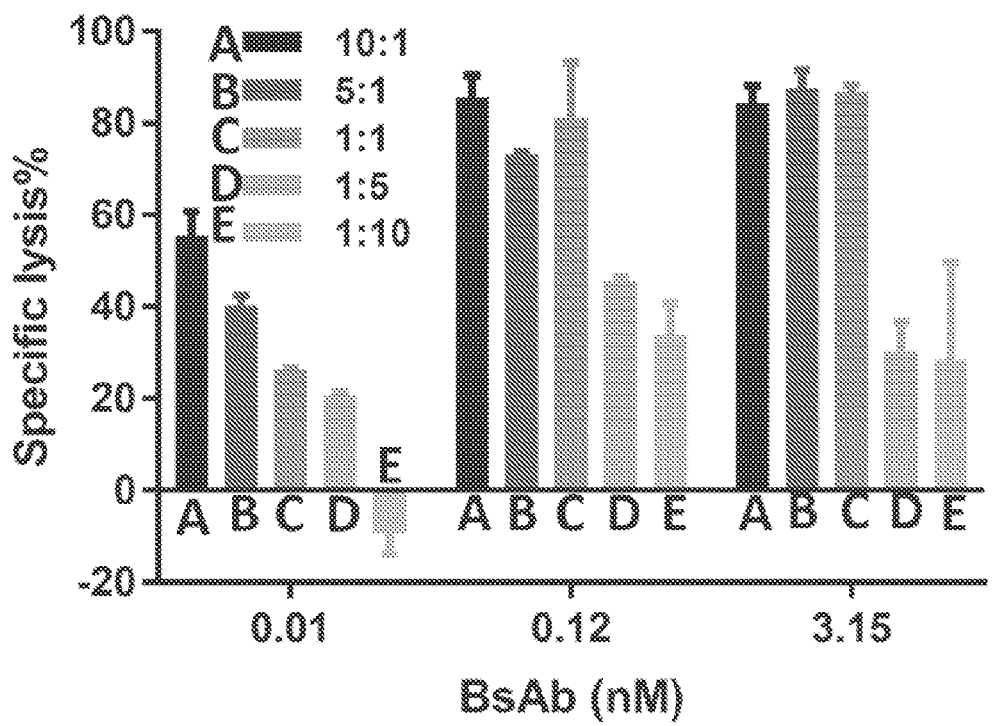
Figure 10E:
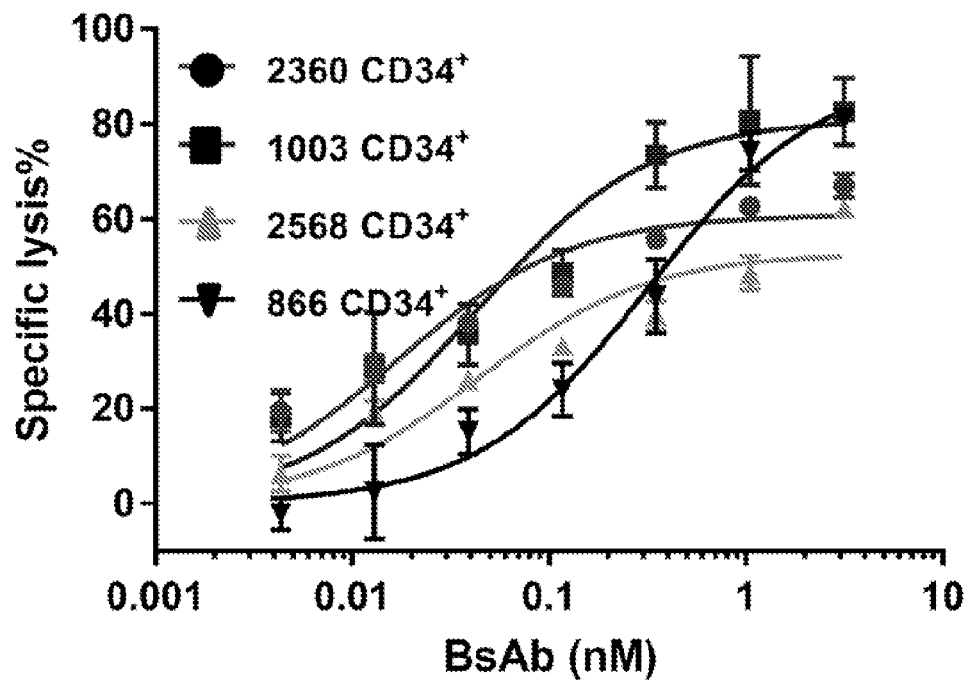
Figure 10F:
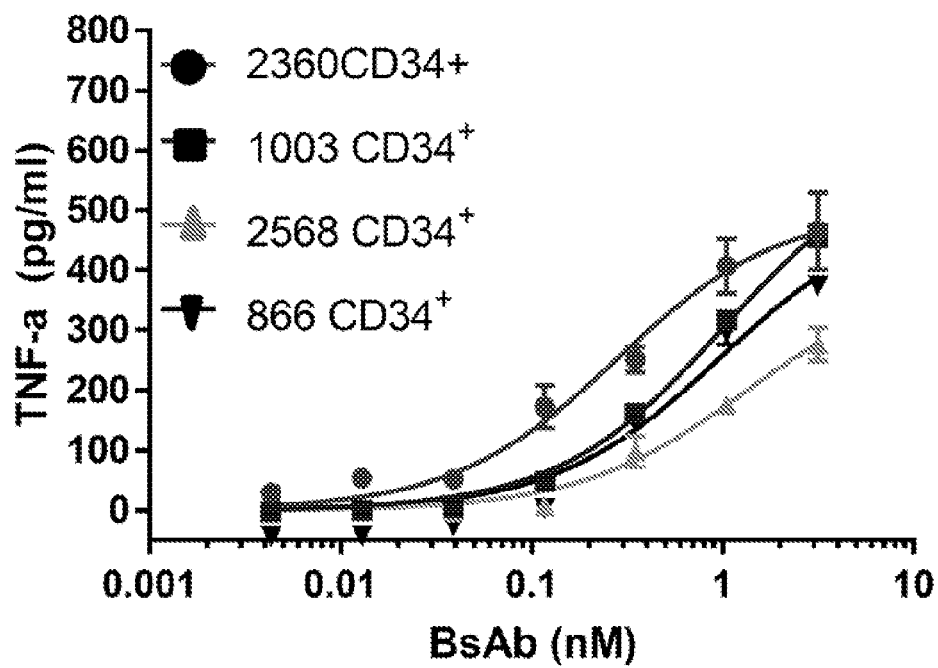
Figure 10G:
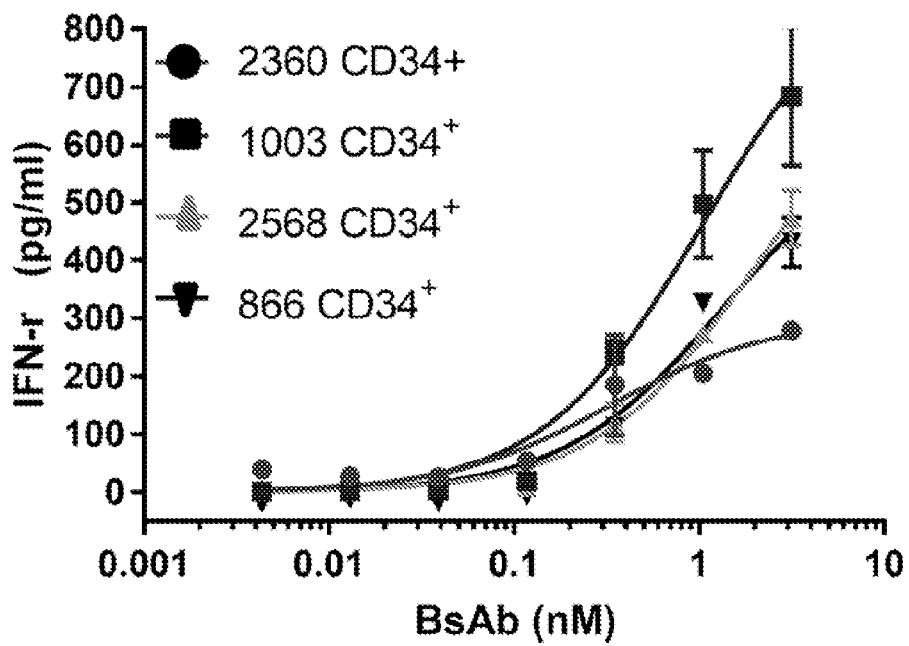
Figure 10H:
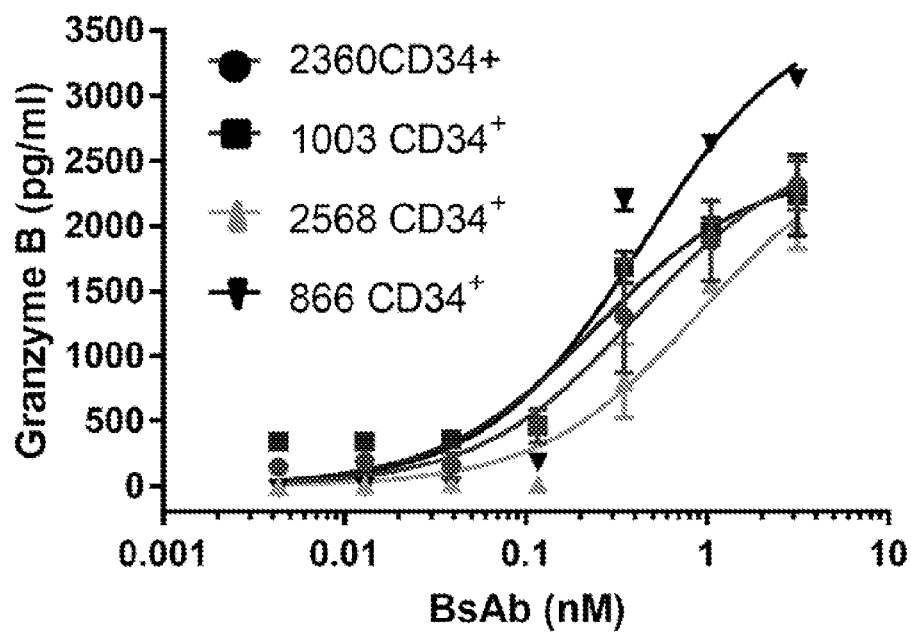
Figure 10I:
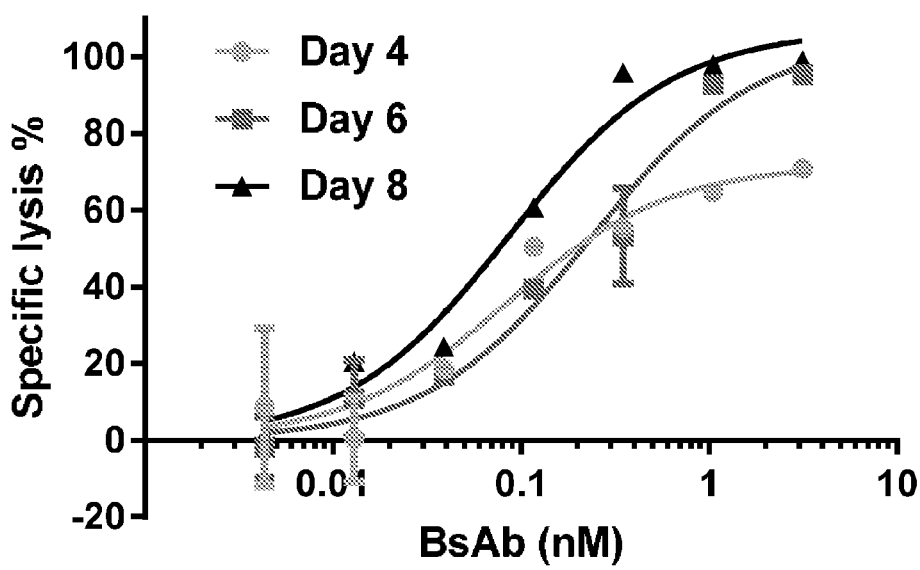
Figure 10J:
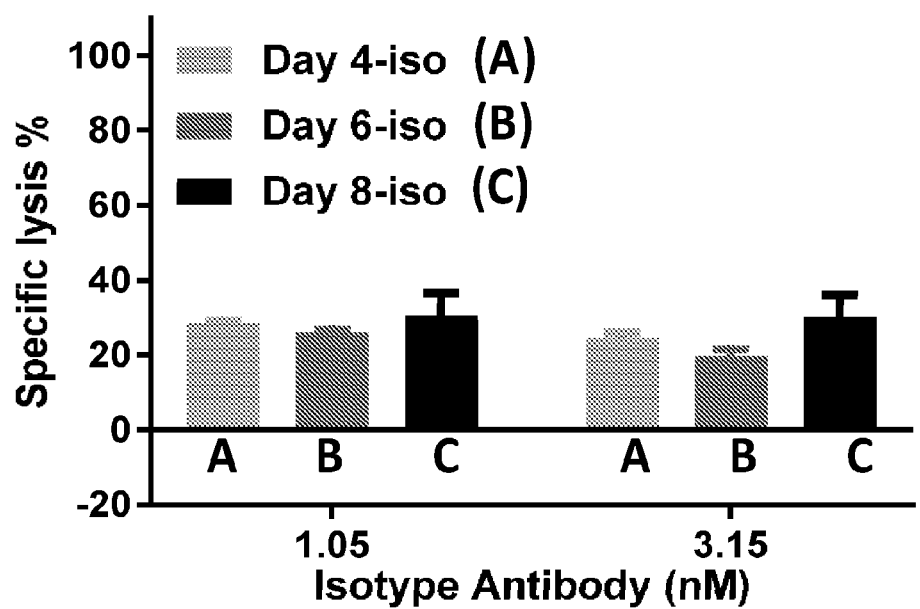
Figure 10K:
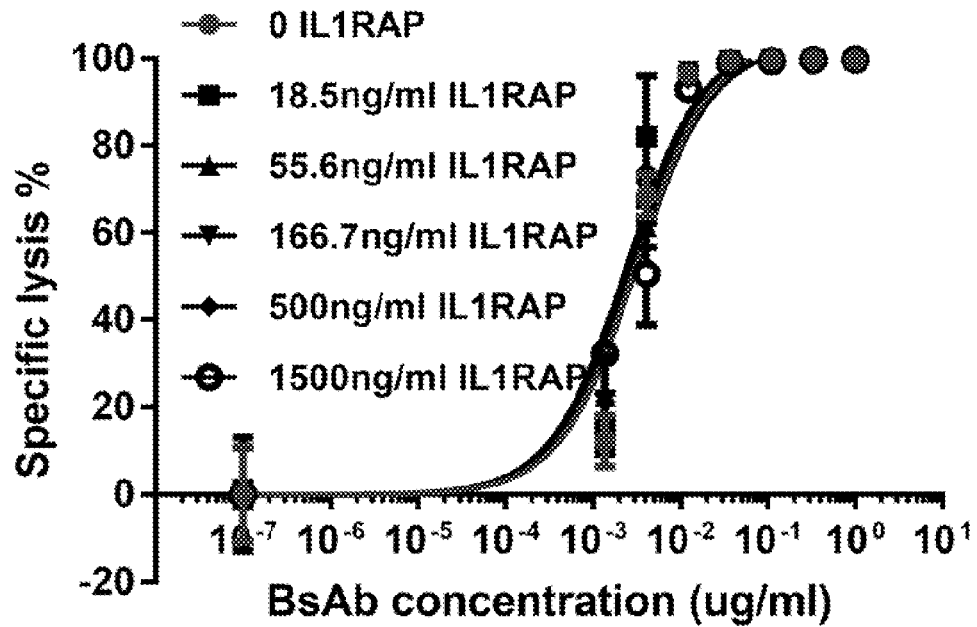
Figure 11A:
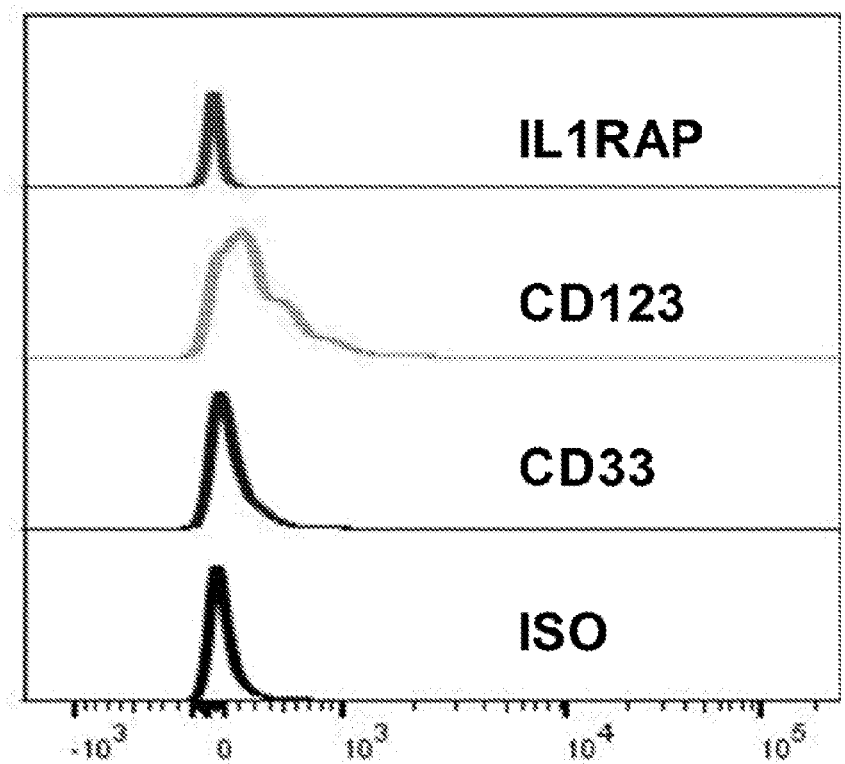
FIGS. 11A-11D. MM001 induced minimal toxicity to CD34+ enriched normal bone marrow cells.
Figure 11B:
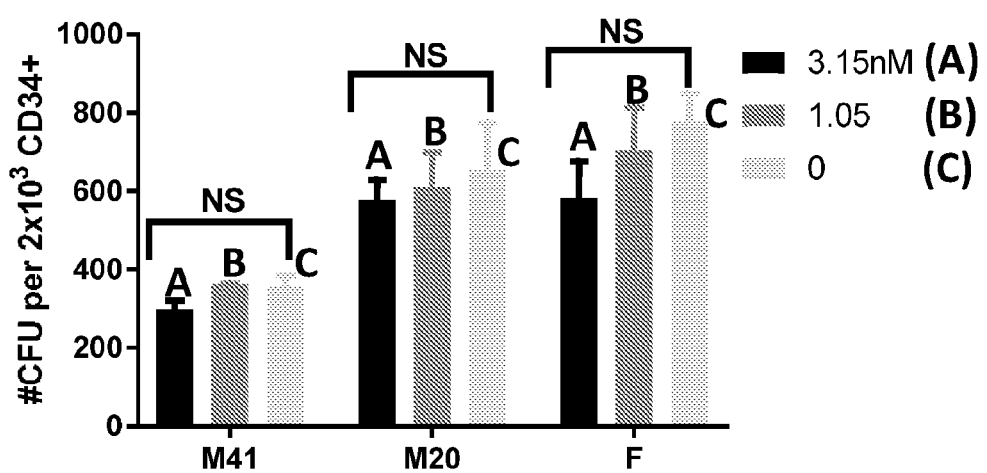
Figure 11C:
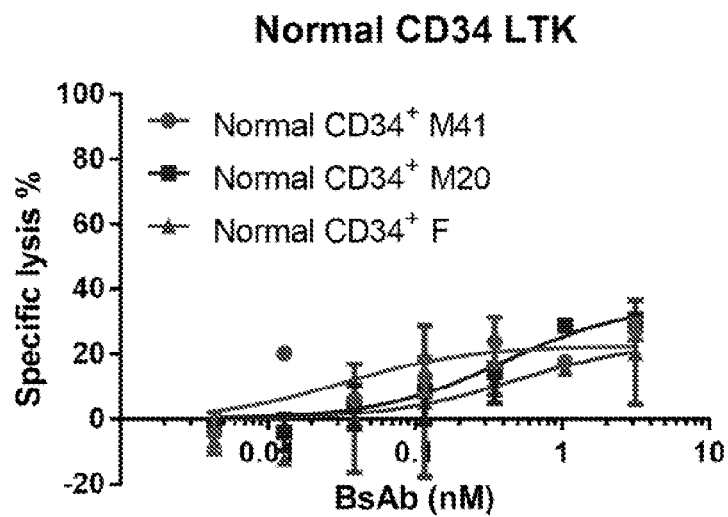
Figure 11D:
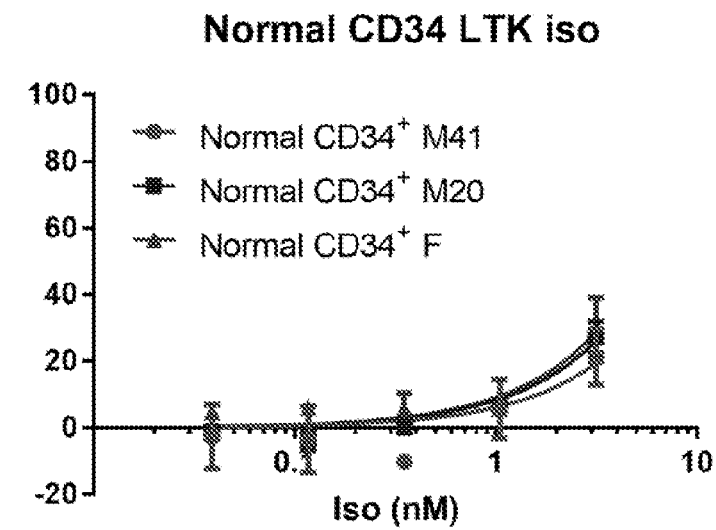
Figure 12A:
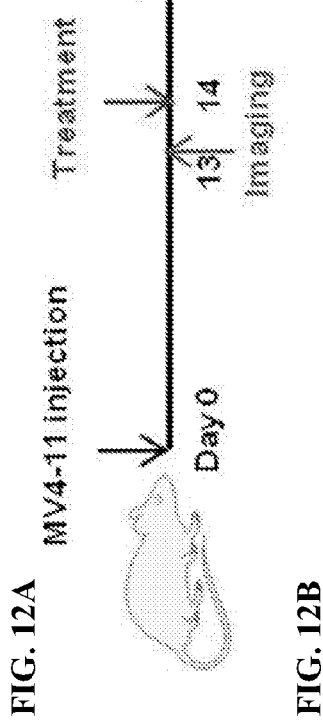
FIGS. 12A-12D. In vivo efficacy study of MM001.
Figure 12B:
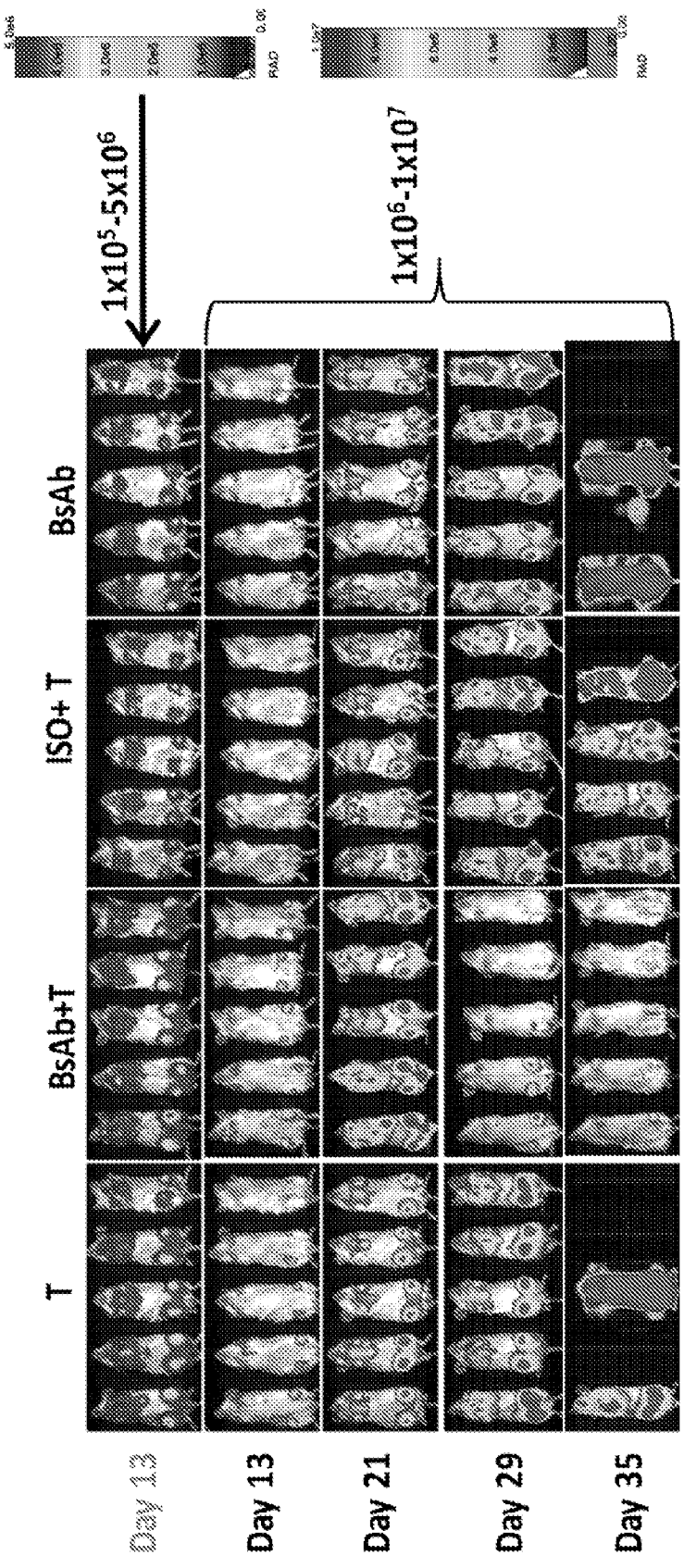
Figure 12C:
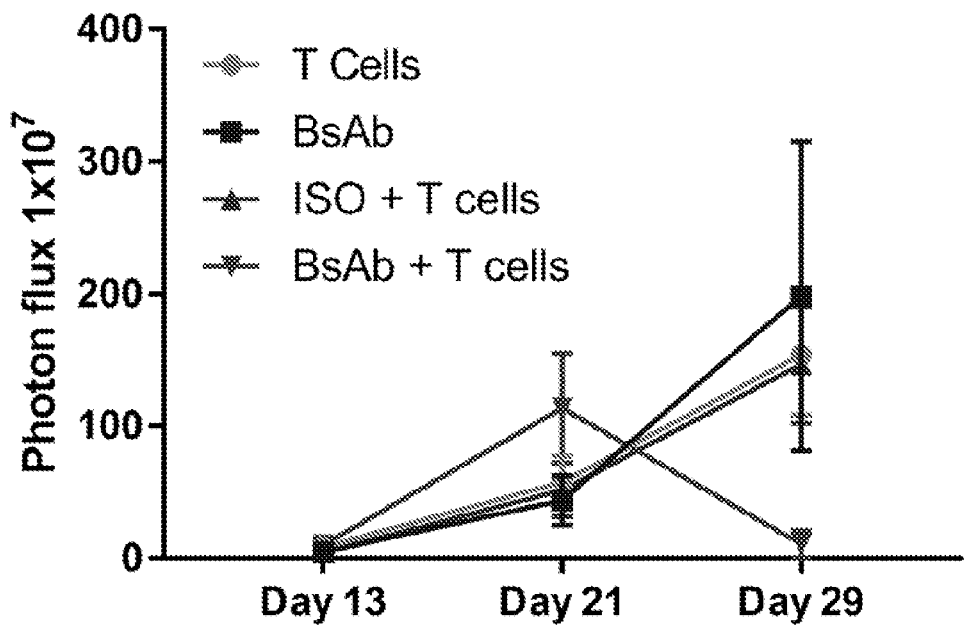
Figure 12D:
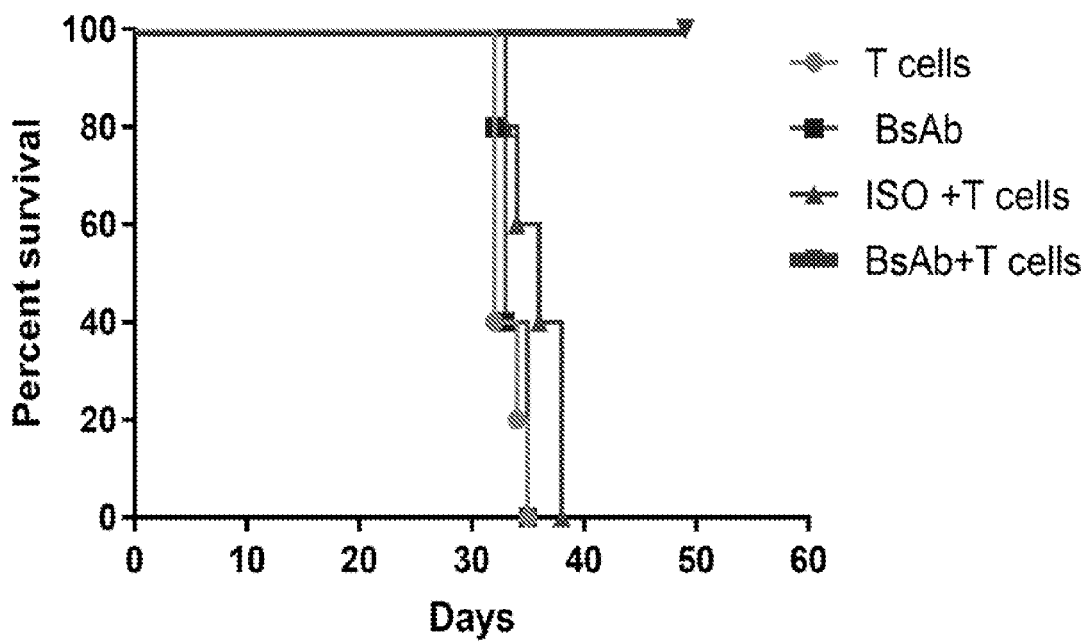
Figure 13A:
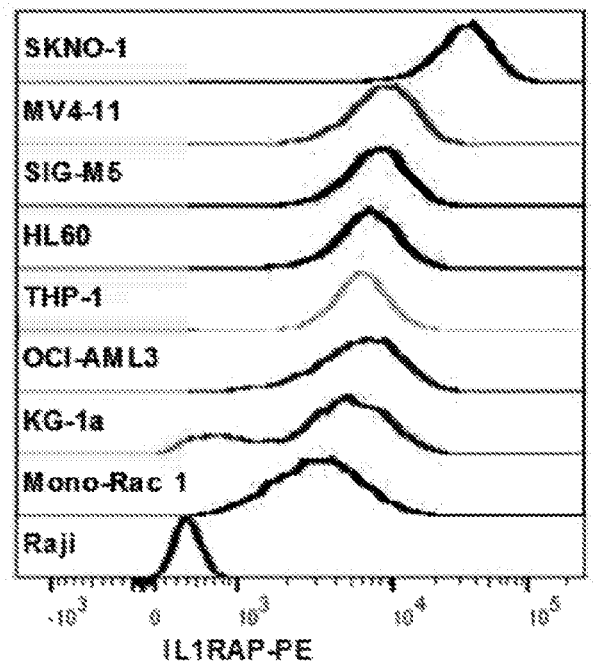
FIGS. 13A-13F. Expression of candidate AML immunotherapy targets on AML cells. IL1RAP (FIG. 13A), CD123 (FIG. 13B), and CD33 (FIG. 13C) expression on different AML cells lines were detected by flow cytometry. The specific binding copies per cell (ABC or antibody binding copies) on AML cell lines were determined for IL1RAP (FIG. 13D), CD123 (FIG. 13E), and CD33 (FIG. 13F).
Figure 13B:
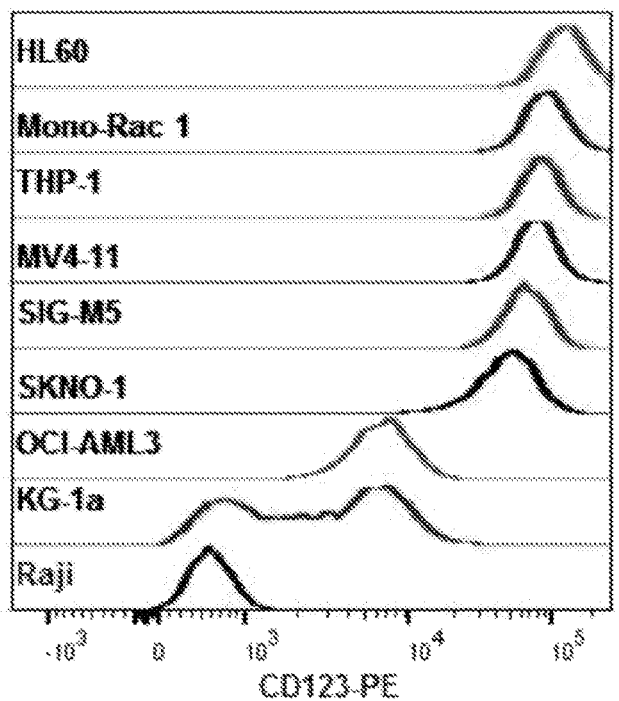
Figure 13C:
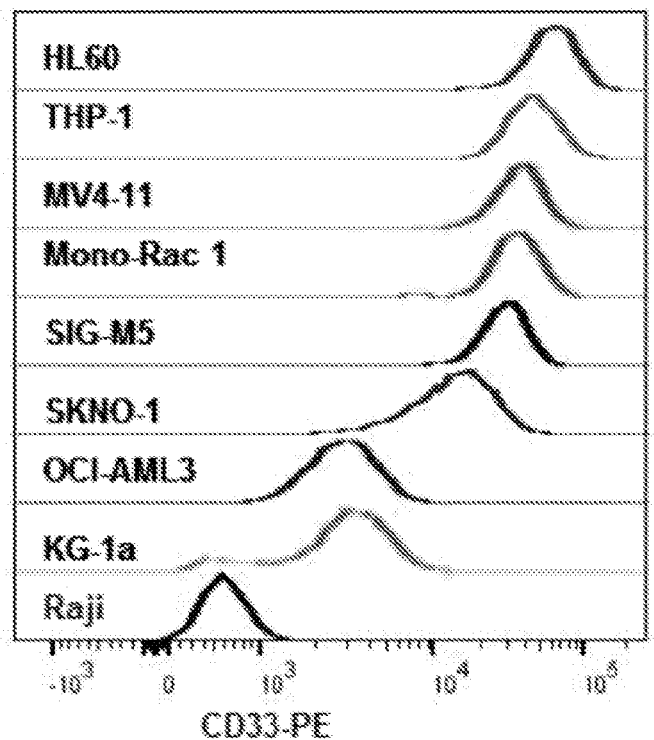
Figure 13D:
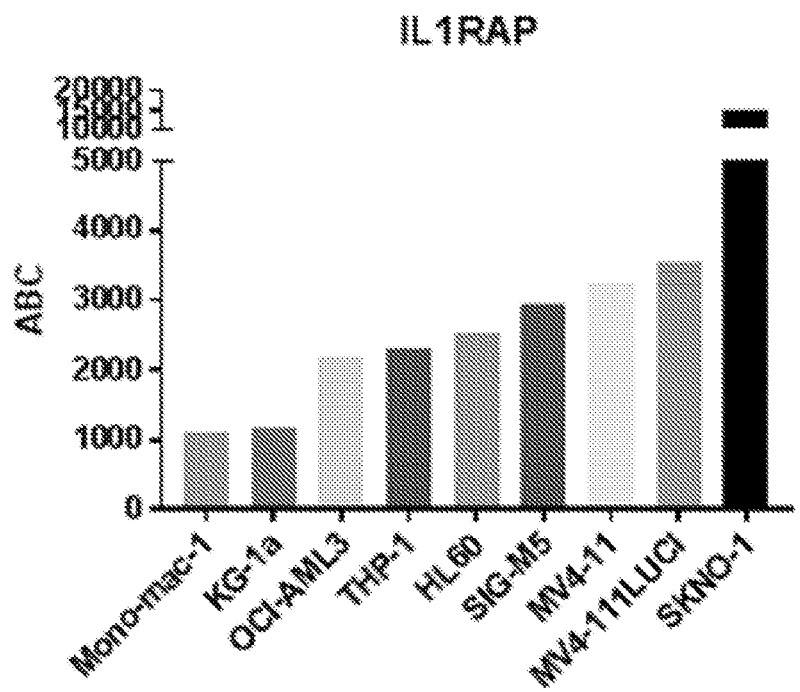
Figure 13E:
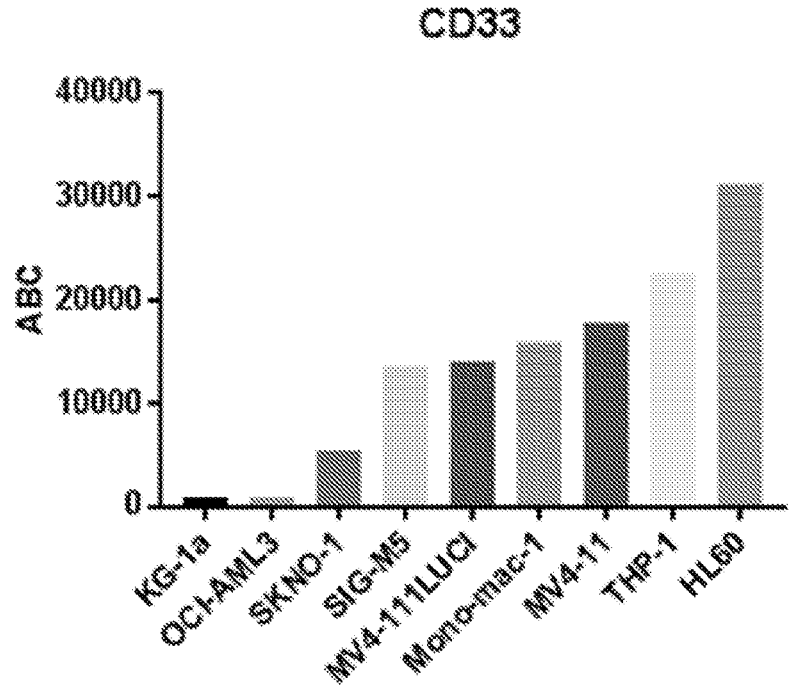
Figure 13F:
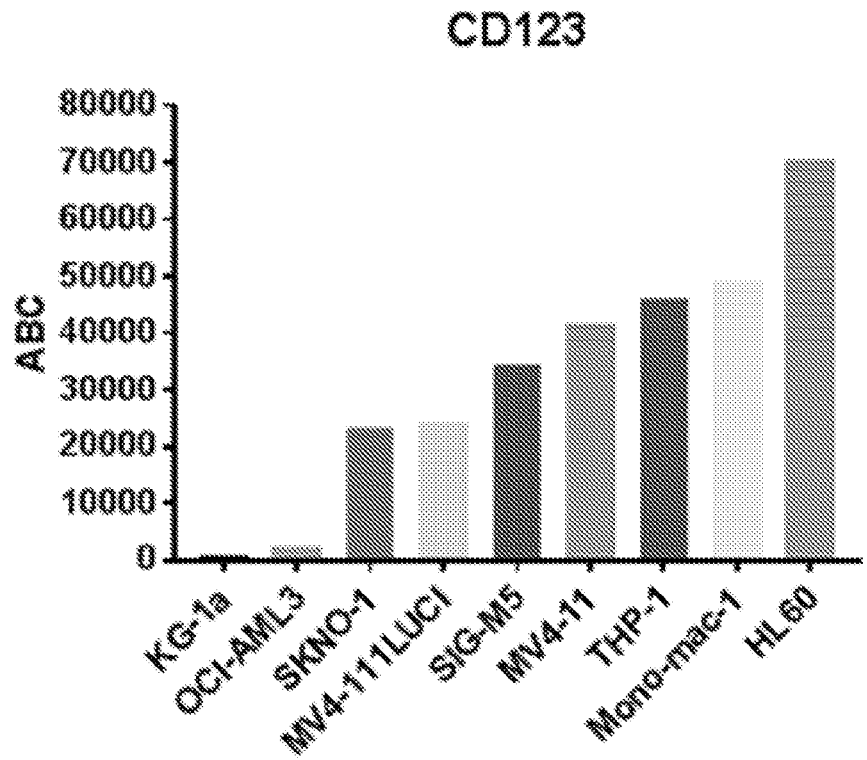
Figure 14A:
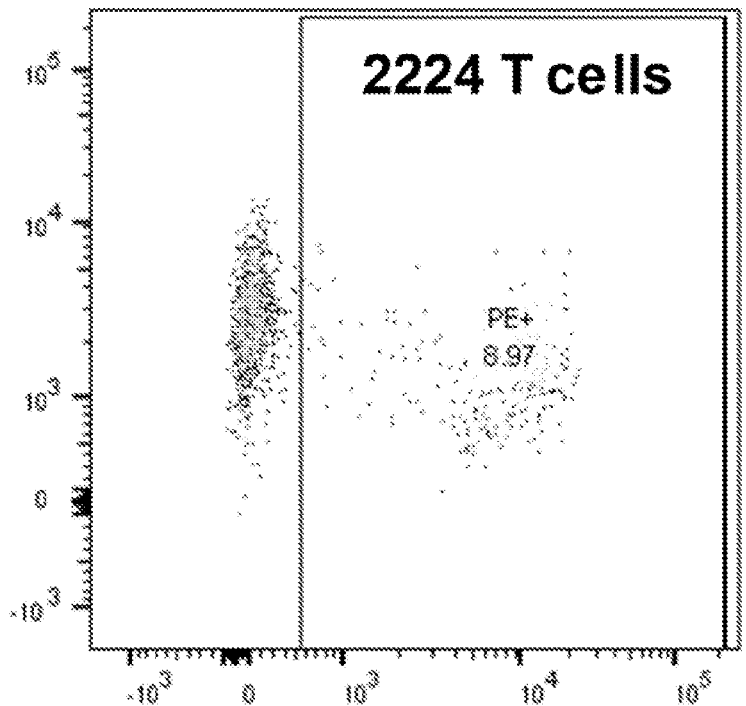
FIGS. 14A-14I. Killing of AML primary samples by autologous T cells induced by MM001. T cell percentage was 8.97% in AML 2224 (FIG. 14A), 4.35% in AML 2515 (FIG. 14D), 3.05% in AML 3448 (FIG. 14G). IL1RAP+ cell percentage was 87.1% in AML 2224 (FIG. 14B), 94.2% in AML 2515 (FIG. 14E), 95.9% in AML 3448 (FIG. 14H). The killing assays were conducted by adding MM001 of indicated concentration in AML samples. Specific lysis was detected on day 4, 6, and 8. The actual E:T ratios were 1:10 for AML 2224 (FIG. 14C), 1:21.9 for AML 2515 (FIG. 14F), 1:31.8 for AML 3448 (FIG. 14I).
Figure 14B:
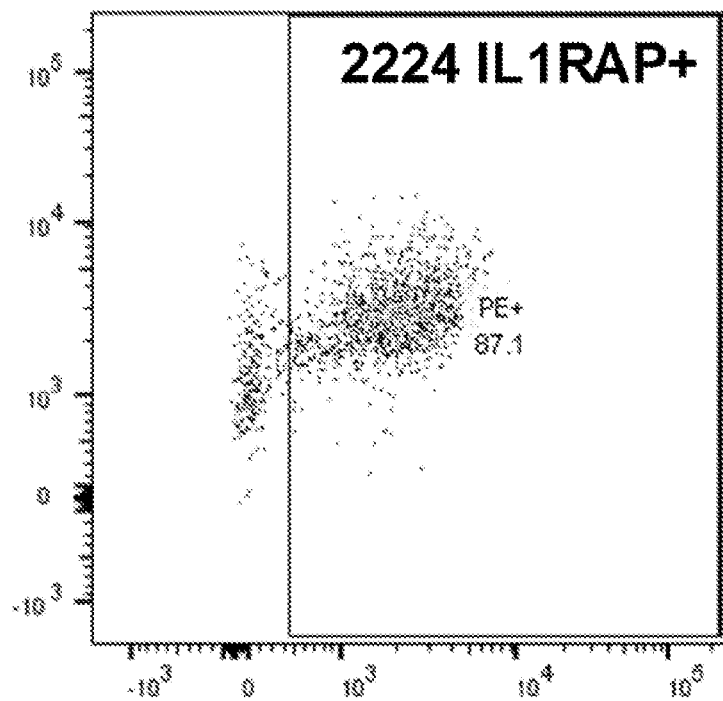
Figure 14C:
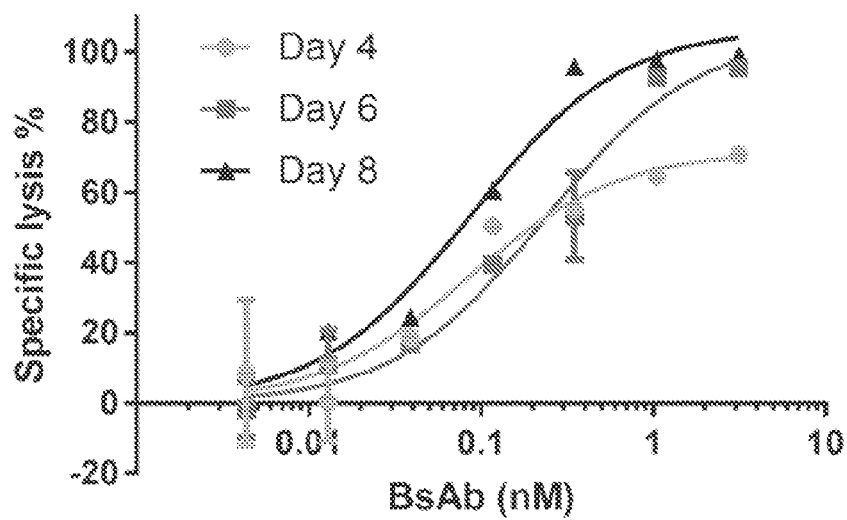
Figure 14D:
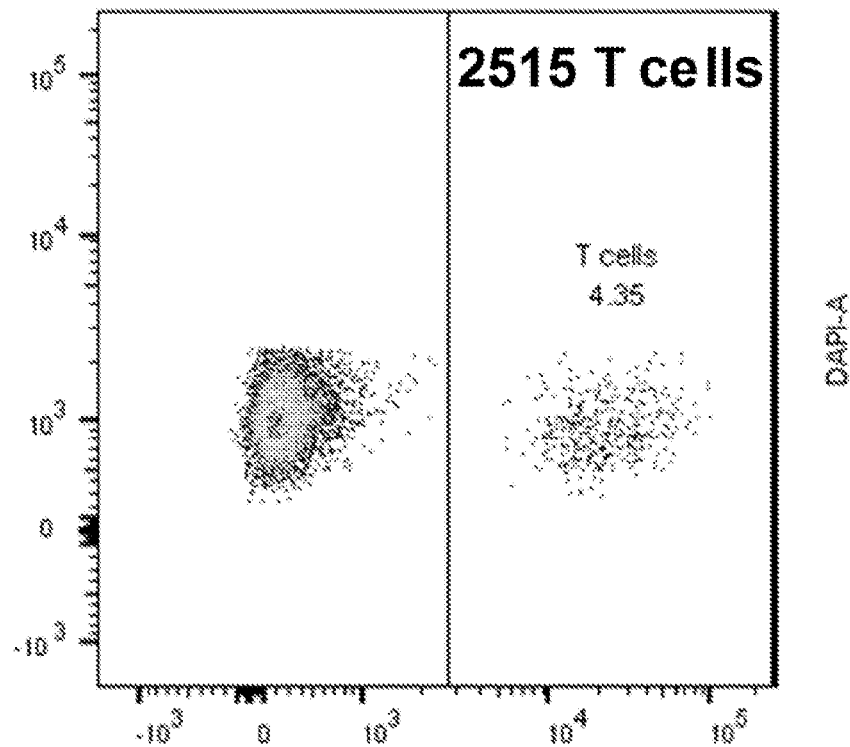
Figure 14E:
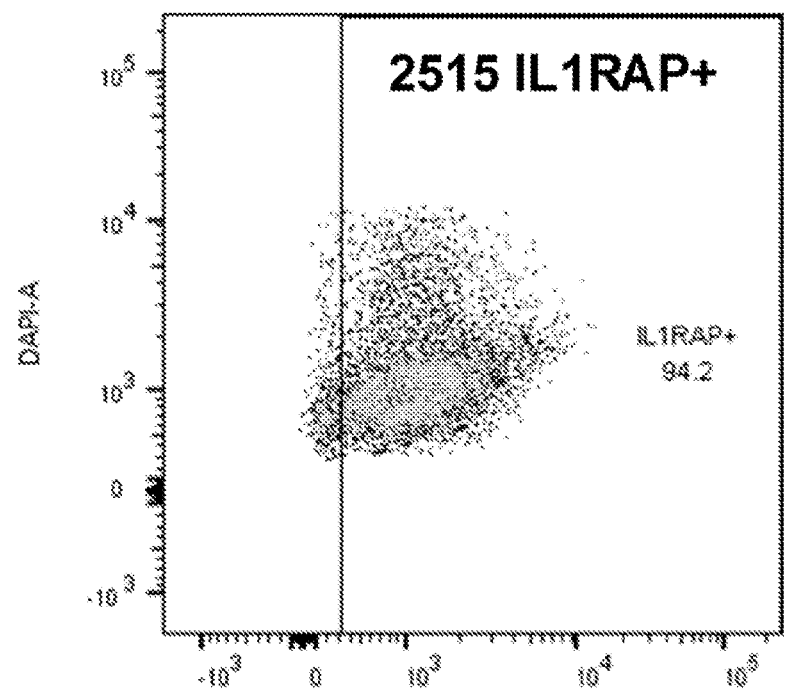
Figure 14F:
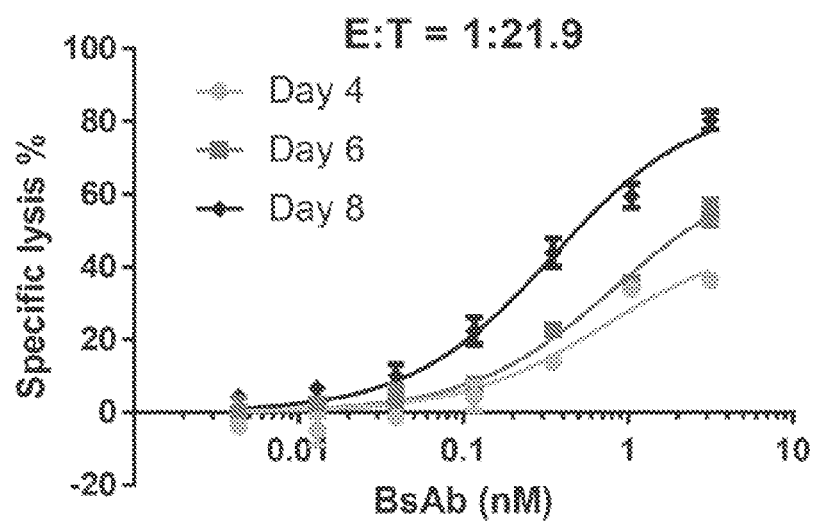
Figure 14G:
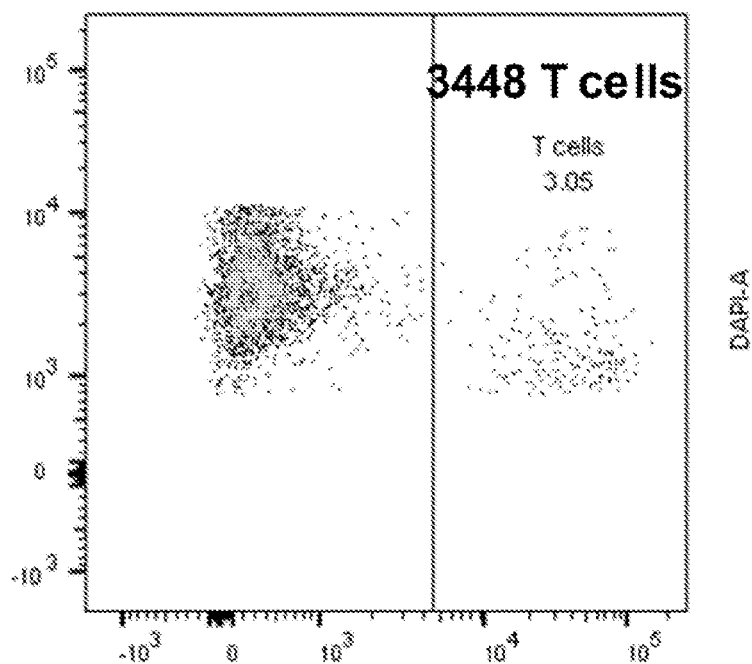
Figure 14H:
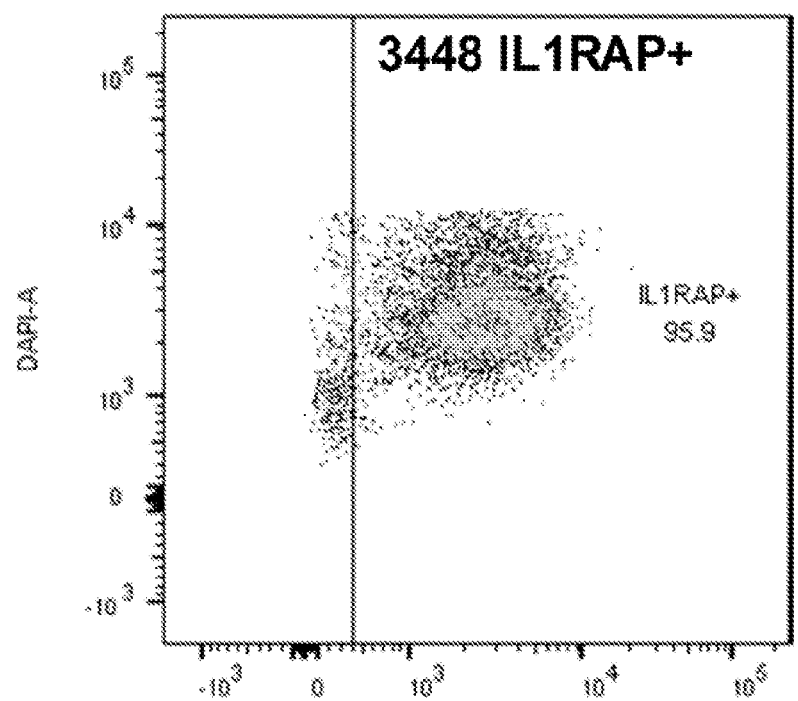
Figure 14I:
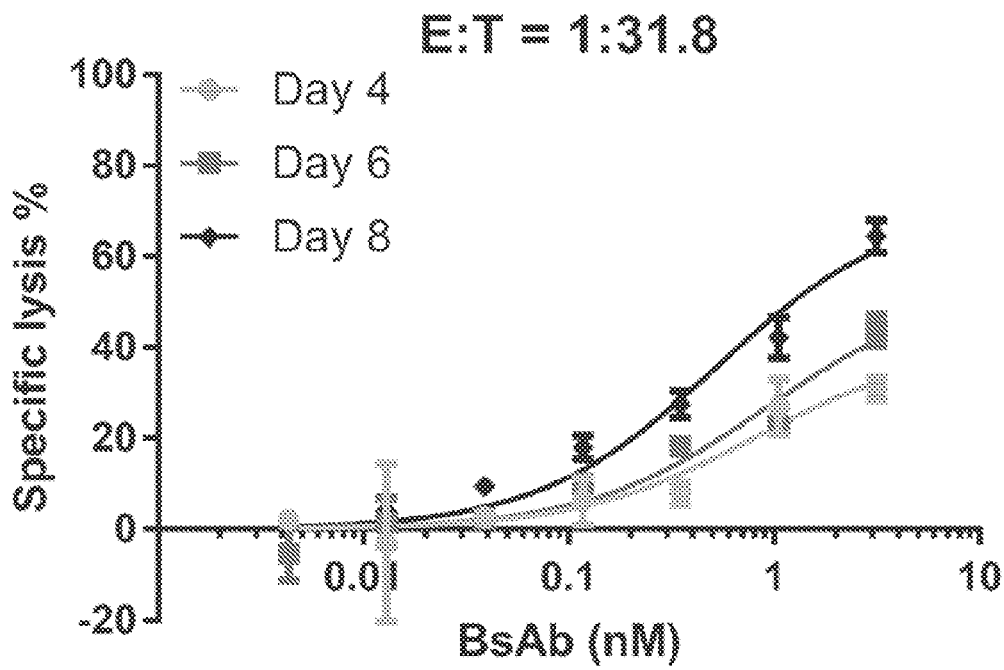
Figure 15A:
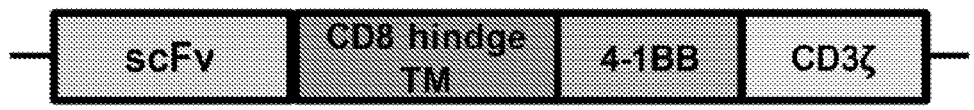
FIGS. 15A-15D. Design and efficacy study of IL1RAP targeting CAR-T cells (CM001). 15A: schematic diagram of the CAR containing a CD8 hindge transmembrane domain, and intracellular signaling domain of 4-1BB, and the CD3z signaling domain. The killing potency of CM001 was conducted by long-term killing assay with MV4-11 cells (15B), HL60 (15C), and KG-1a (15D) at different E:T ratio.
Figure 15B:
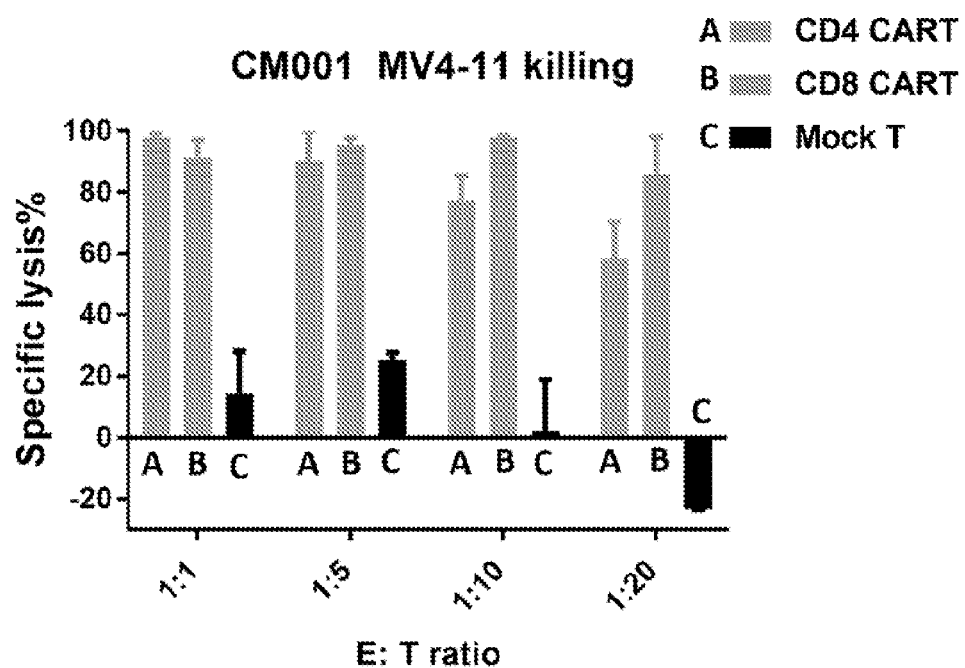
Figure 15C:
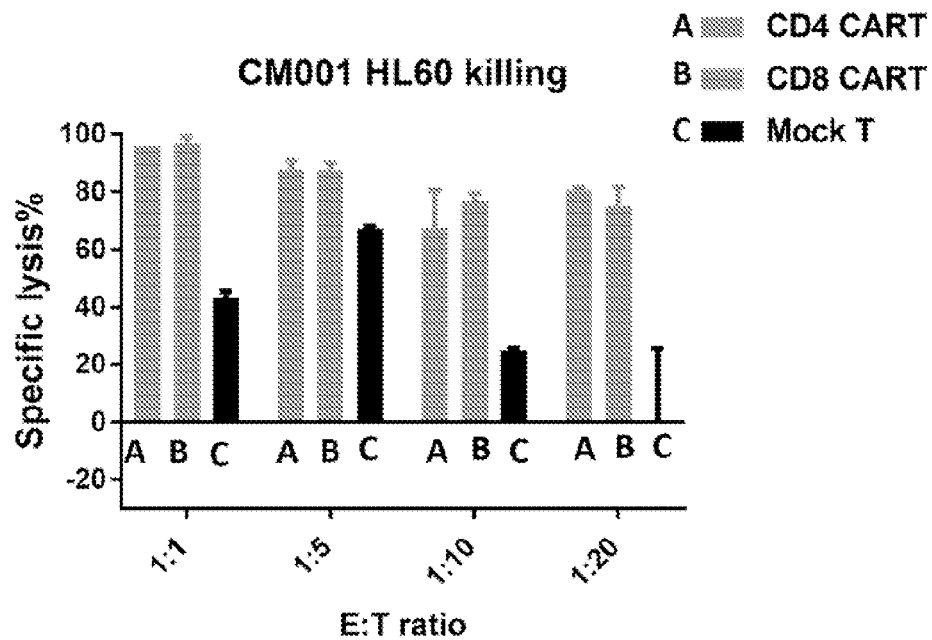
Figure 15D:
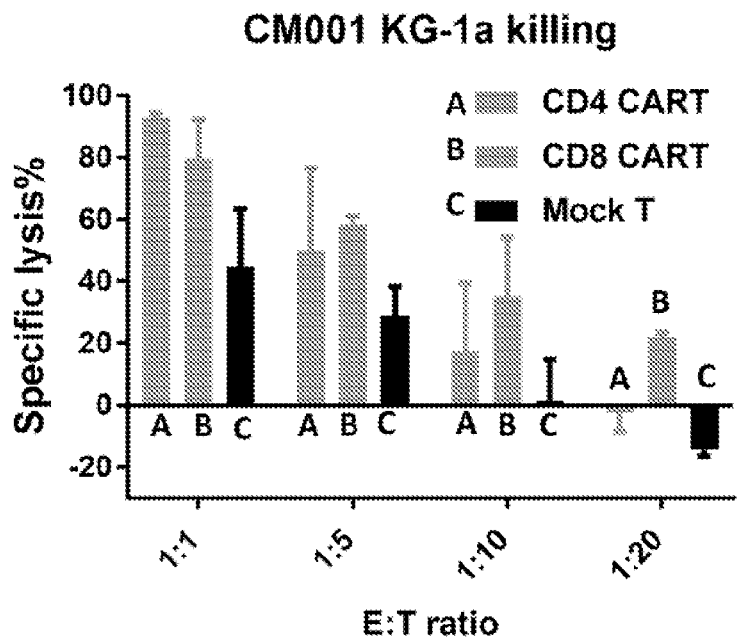
Figure 16A:
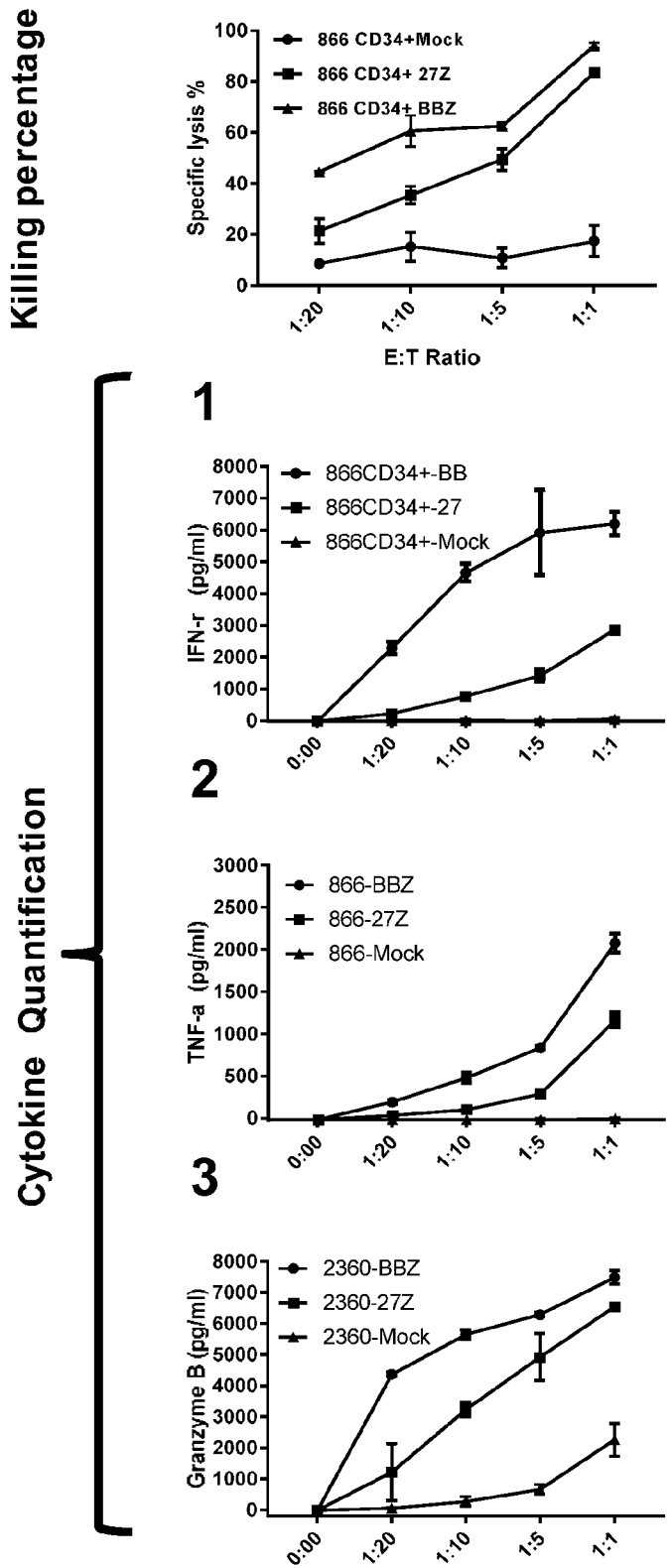
FIGS. 16A-16D. Efficacy evaluation of CM001 with CD34+ enriched AML cells. 16A: killing of CD34+ 886 AML cells by IL1RAP-specific CAR-T cells at indicated E:T ratio. Cytokines were determined by ELISA for IFN-γ (Panel 1), TNF-α (Panel 2), and Granzyme B (Panel 3). 16B: killing of CD34+ 2360AML cells by IL1RAP-specific CAR-T cells at indicated E: T ratio. Cytokines were determined by ELISA for IFN-γ (Panel 1), TNF-α(Panel 2), and Granzyme B (Panel 3). 16C: killing of CD34+ 2568 AML cells by IL1RAP-specific CAR-T cells at indicated E:T ratio.
Figure 16B:
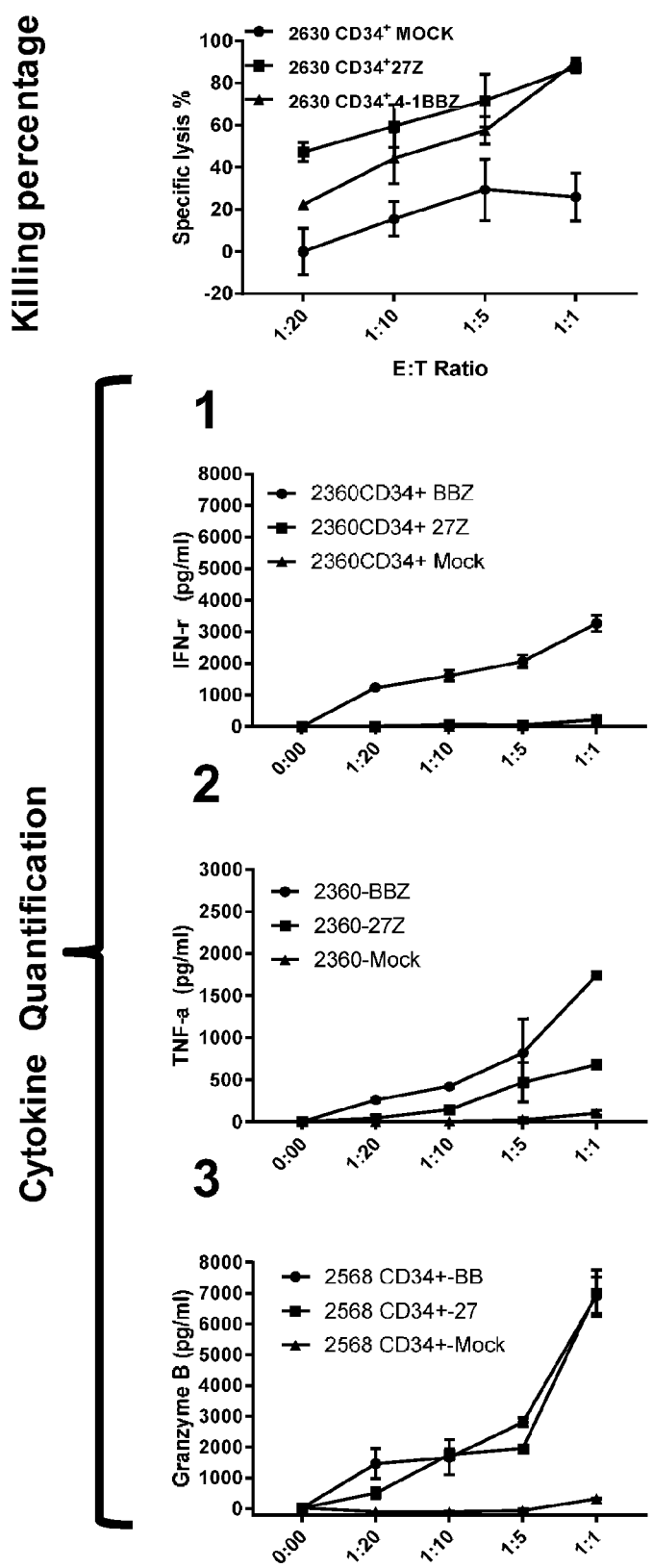
Figure 16C:
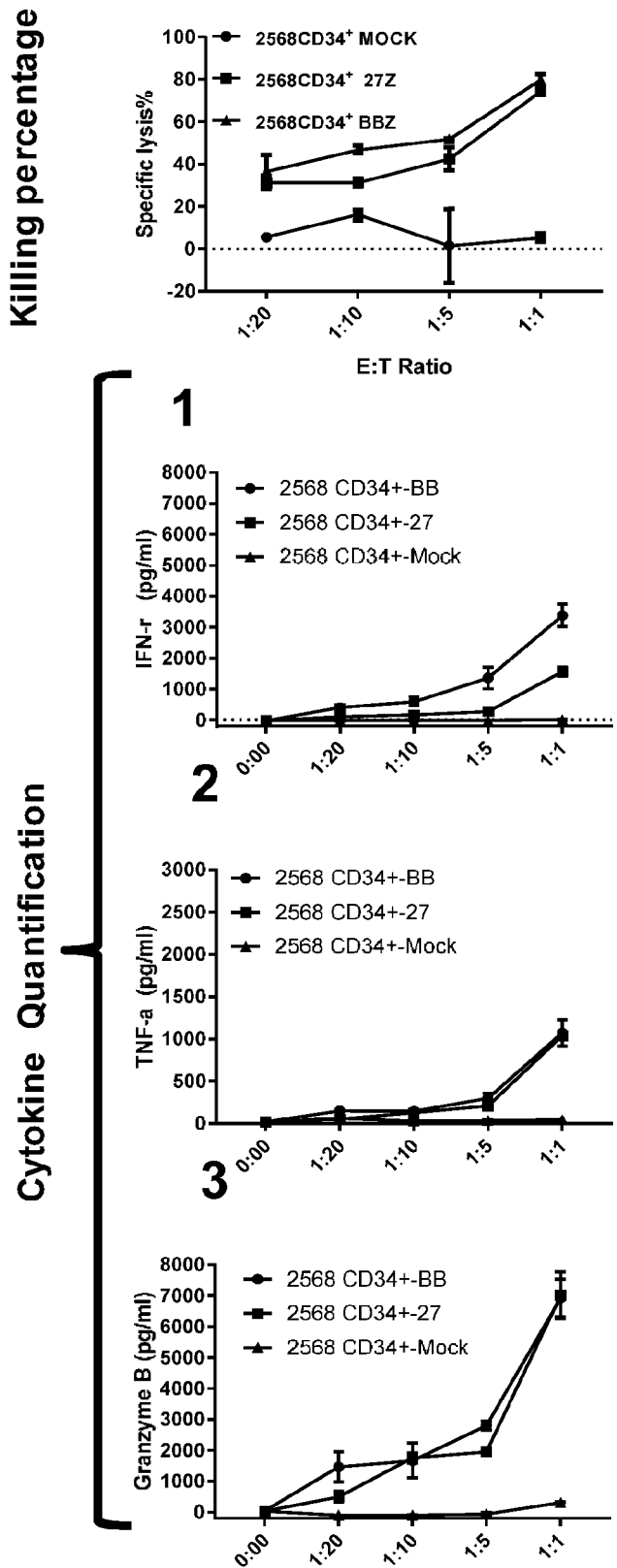
Figure 16D:
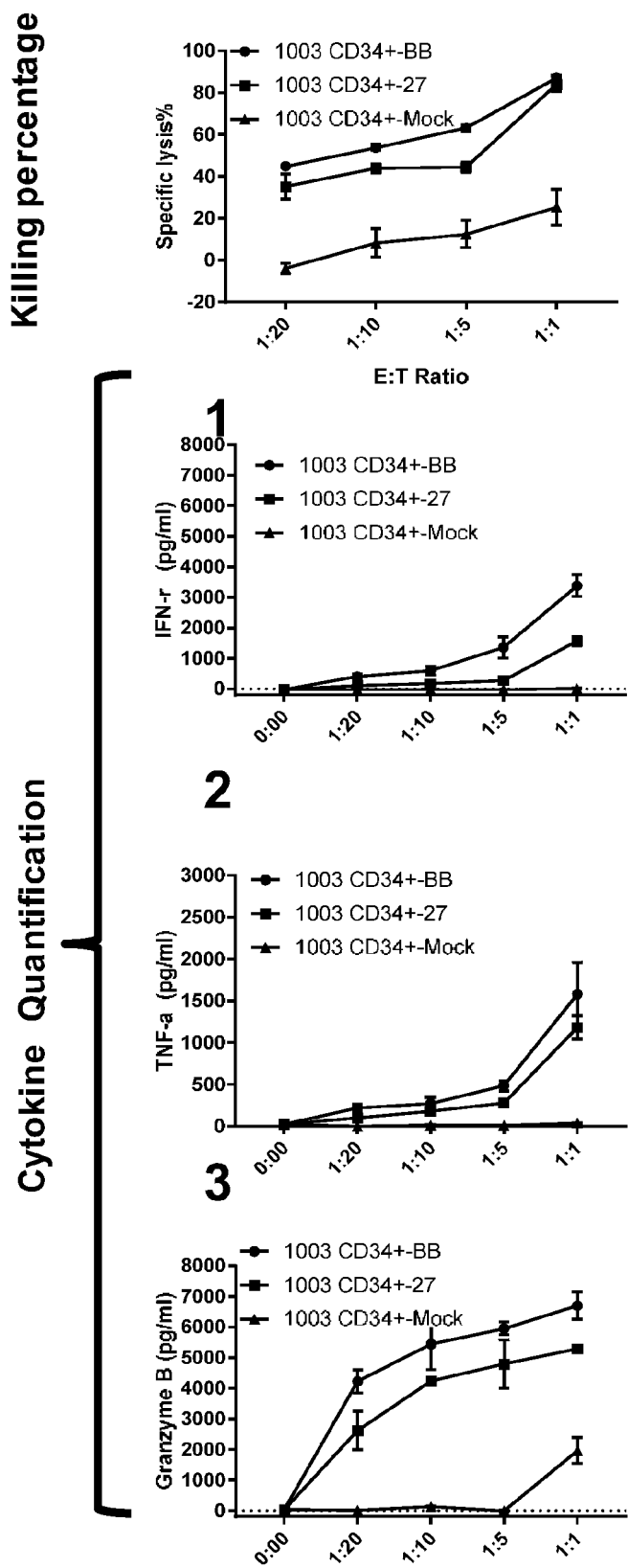

Optimize therapeutic efficacy, dose and schedule of anti-IL1RAPxCD3 BsAb to target AML LSC. T cell-redirected tumor cell killing is a promising immunologic approach to treat hematologic malignancies [7, 10, 11]. BsAb can redirect polyclonal T cells against tumor cells by binding to tumor antigen and T cell co-receptor CD3. This interaction induces activation and cytotoxicity of T effector cells against target cancer cells in a major histocompatibility complex-independent manner, bypassing an immune escape mechanism [7]. To create anti-IL1RAPxCD3 BsAb, Applicants first constructed a human phage display library from healthy donor-derived peripheral blood B cells (FIGS. 1A-1C, Table 1) and screened 12 clones producing anti-IL1RAP monoclonal antibodies (Ab). Ab from clone ID5 showed the highest binding ability to recombinant human IL1RAP protein using ELISA (FIGS. 2A-2B, 2D and Table 2, with an $EC_{50}$ of 4.9 ng/ml) and the highest specific lysis rate in Antibody Dependent Cellular Cytotoxicity (ADCC) assays (FIG. 2C), and therefore was selected for development of anti-IL1RAPxCD3 BsAb (FIGS. 3A-3C) and IL1RAP-CAR-T cells (FIGS. 7A-7B). The $EC_{50}$ values determined in the 48 hours long term killing assays with different cell lines are: 6.718 ng/ml for HL60 cells, 5.362 ng/ml for MOLM13 cells, 6.368 ng/ml for OCI-AML3 cells,

TABLE 1

List of CDR3H and CDR3L amino acid sequences from 50 randomly selected clones. The CDR3 sequences showed that no repetitive sequences could be found from these randomly picked 50 colonies.

| CDR3H-IMGT | CDR3L-IMGT |
|---|---|
| ARDESHSTITPRH (SEQ ID NO: 22) | QCGIVVVIIFM (SEQ ID NO: 56) |
| ARVGPHYSDSSGYYYIDDNSYDMDV (SEQ ID NO: 23) | LQHRSGYL (SEQ ID NO: 57) |
| ARDVWVVPAAPLYYYYGMDV (SEQ ID NO: 24) | MQGIHLPRYT (SEQ ID NO: 58) |
| ARDGDYGVWWFDP (SEQ ID NO: 25) | QQYYSSPLT (SEQ ID NO: 59) |
| ARGRLASGSWNGFDI (SEQ ID NO: 26) | QQYYSMVSLT (SEQ ID NO: 60) |
| AAESGRPGFGSYWGVFYYNHAMDV (SEQ ID NO: 27) | LVWHNRAWV (SEQ ID NO: 61) |
| ARDGNVPMASDFYGMDL (SEQ ID NO: 28) | QQYDNLLLT (SEQ ID NO: 62) |
| ARGKGDSYAFDI (SEQ ID NO: 29) | QAWDNTSQYV (SEQ ID NO: 63) |
| AKGHYYYYGMDV (SEQ ID NO: 30) | QQSYTVPYT (SEQ ID NO: 64) |
| ARAGSGWYGYFDS (SEQ ID NO: 31) | QKYNSAPYT (SEQ ID NO: 65) |
| ARDSERVVSGWYVYYYYYYMDV (SEQ ID NO: 32) | QVWDRSGDHQGV (SEQ ID NO: 66) |
| AKDLRGYSYGNYNRDAFDI (SEQ ID NO: 33) | QSYDSSLSGSGVV (SEQ ID NO: 67) |
| ARGKGDYLYYGMDV (SEQ ID NO: 34) | QYYNTYSPWT (SEQ ID NO: 68) |
| ARPEGGSSLVGGFDY (SEQ ID NO: 35) | AVWDDSLKGVV (SEQ ID NO: 69) |
| ARFGGATFDGPFDI (SEQ ID NO: 36) | LQHNTYPWT (SEQ ID NO: 70) |
| ARRDTAMENFDY (SEQ ID NO: 37) | QQRSNWPELT (SEQ ID NO: 71) |
| ARLYYDFWSGSA (SEQ ID NO: 38) | MQALQTPWT (SEQ ID NO: 72) |
| ARRSPDCSLTTCLPLH (SEQ ID NO: 39) | QQYADSPLT (SEQ ID NO: 73) |
| VRDVSPGGADV (SEQ ID NO: 40) | QQYGRSPPFA (SEQ ID NO: 74) |
| AKGGTLDAFGI (SEQ ID NO: 41) | QQSHSSSR (SEQ ID NO: 75) |
| ARAFNRYCSGGSCYPPGRYGMDV (SEQ ID NO: 42) | CSYAGAYTEI (SEQ ID NO: 76) |
| ARDHESRSPGDYHMDV (SEQ ID NO: 43) | HQYGSIPHT (SEQ ID NO: 77) |
| ASLDLTAARSVIAAFDI (SEQ ID NO: 44) | GADHGSGSNFLYV (SEQ ID NO: 78) |
| ARGDSSDYWTSTDAFDI (SEQ ID NO: 45) | QVWDSGSDQGV (SEQ ID NO: 79) |
| AIPYGDYPPAFAV (SEQ ID NO: 46) | QQYHTIPYS (SEQ ID NO: 80) |
| ARDSPEGAFDI (SEQ ID NO: 47) | QQYGSSPRT (SEQ ID NO: 81) |
| ARFNCYSSGCPLMDY (SEQ ID NO: 48) | LQYGRSPFT (SEQ ID NO: 82) |
| ARDSGSYLFDY (SEQ ID NO: 49) | CSMGCHPKCLWA (SEQ ID NO: 83) |
| ARTLPYDFWSGYSAYYYYYYMDV (SEQ ID NO: 50) | MQGLQTPIG (SEQ ID NO: 84) |

TABLE 1-continued

List of CDR3H and CDR3L amino acid sequences from 50 randomly selected clones. The CDR3 sequences showed that no repetitive sequences could be found from these randomly picked 50 colonies.

| CDR3H-IMGT | CDR3L-IMGT |
|---|---|
| AREDGHTGIYDY (SEQ ID NO: 51) | CSYVGRYTYV (SEQ ID NO: 85) |
| ARGAEYSSSSPDY (SEQ ID NO: 52) | QQYNTYPRA (SEQ ID NO: 86) |
| ARQGNIVVVVANDAFDI (SEQ ID NO: 53) | QHYGSSLWP (SEQ ID NO: 87) |
| AKEVRPGHCSGGSGGSCYSVPGRDYYGMDV (SEQ ID NO: 54) | MQALQTPVT (SEQ ID NO: 88) |
| AGPSGPAKKDAFDI (SEQ ID NO: 55) | QRYNNWPPGIT (SEQ ID NO: 89) |

TABLE 2

Figure 1D:
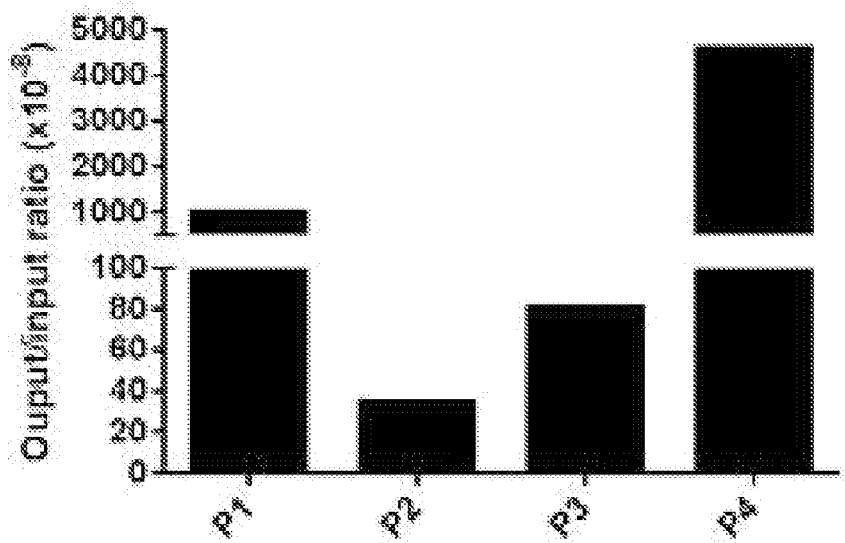

Biopanning for IL1RAP antibodies using recombinant human IL1RAP protein. Enrichment was observed at the fourth round. See also corresponding FIG. 1D

| | $1^{st}$ round | $2^{nd}$ round | $3^{rd}$ round | $4^{th}$ round |
|---|---|---|---|---|
| Input | $1 \times 10^{12}$ | $1 \times 10^{12}$ | $1 \times 10^{12}$ | $1 \times 10^{12}$ |
| Output | $1 \times 10^{8}$ | $3.5 \times 10^{5}$ | $8.1 \times 10^{5}$ | $4.6 \times 10^{7}$ |
| Output/input ratio | $10^{-5}$ | $3.5 \times 10^{-7}$ | $8.1 \times 10^{-7}$ | $4.6 \times 10^{-5}$ |

Figure 4A:
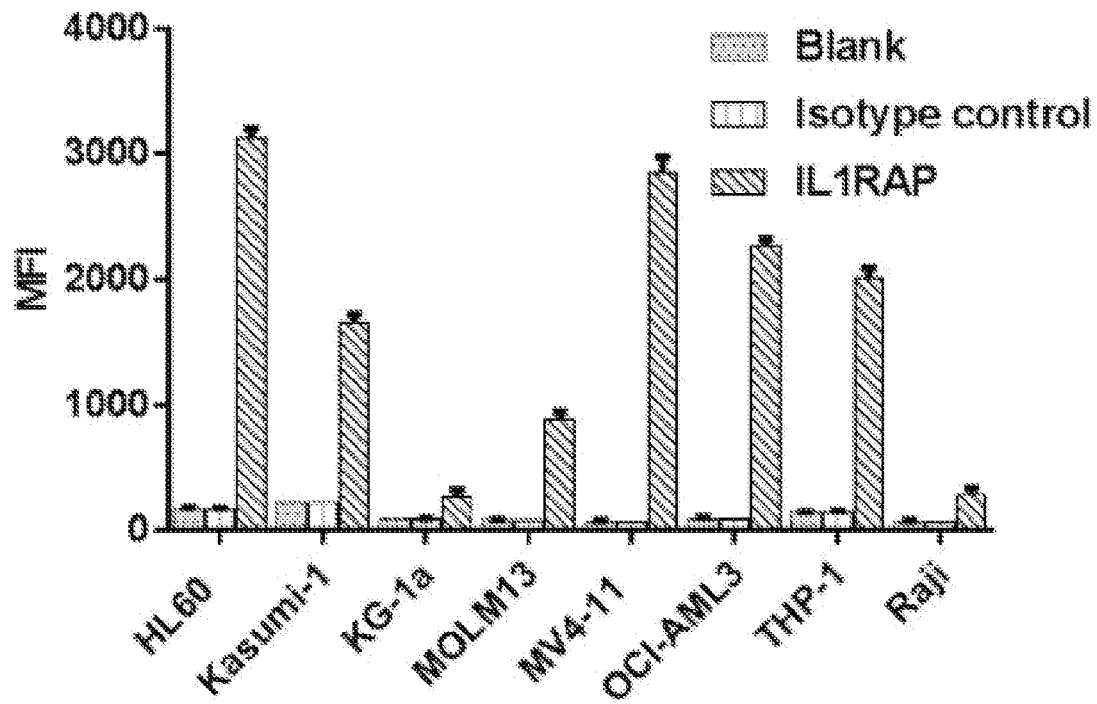
FIGS. 4A-4I. Anti-CD3XIL1RAP bispecific antibody induces T-cell activation and cytotoxicity in AML cell lines.
Figure 4B:
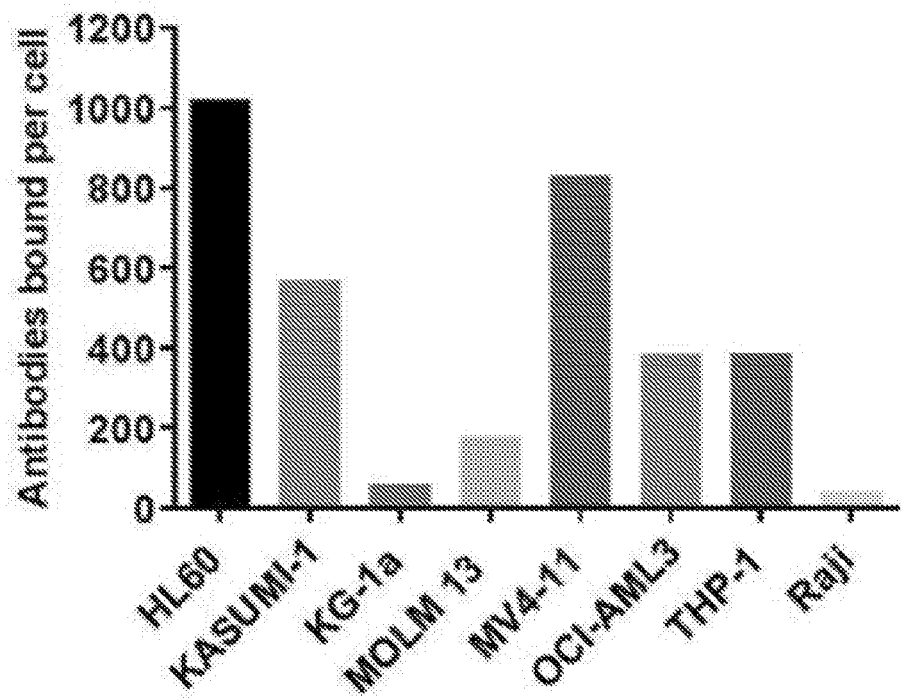
Figure 4C:
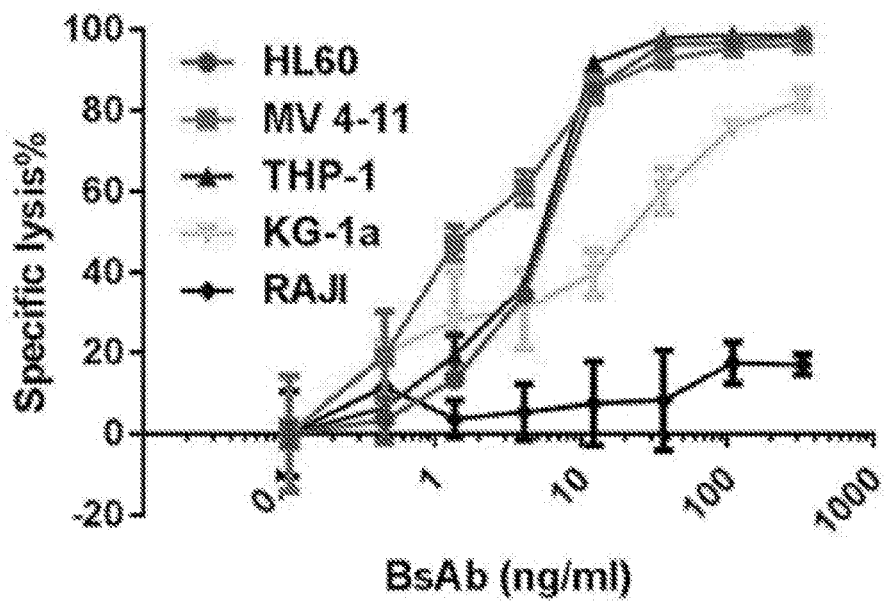
Figure 4D:
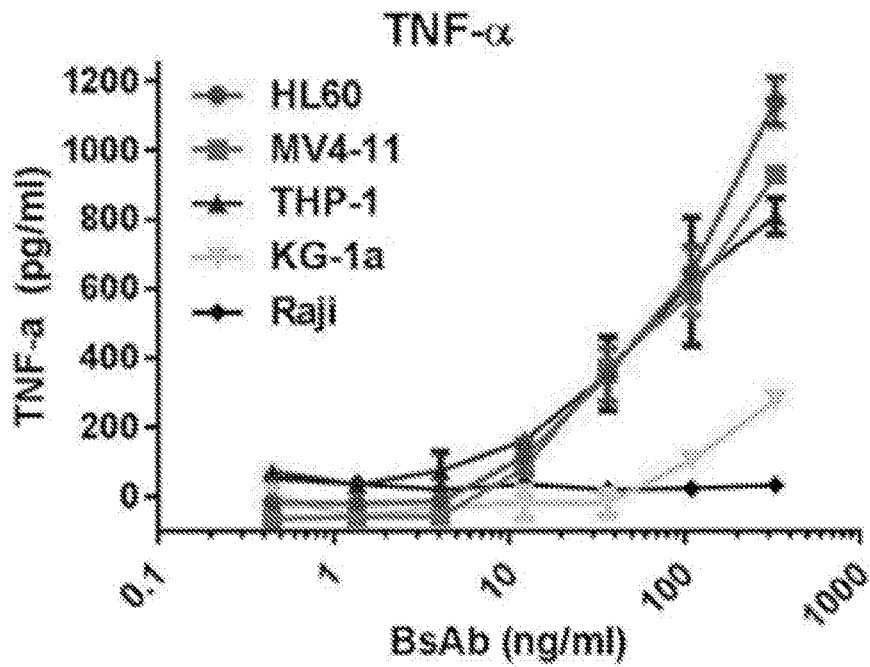
Figure 4E:
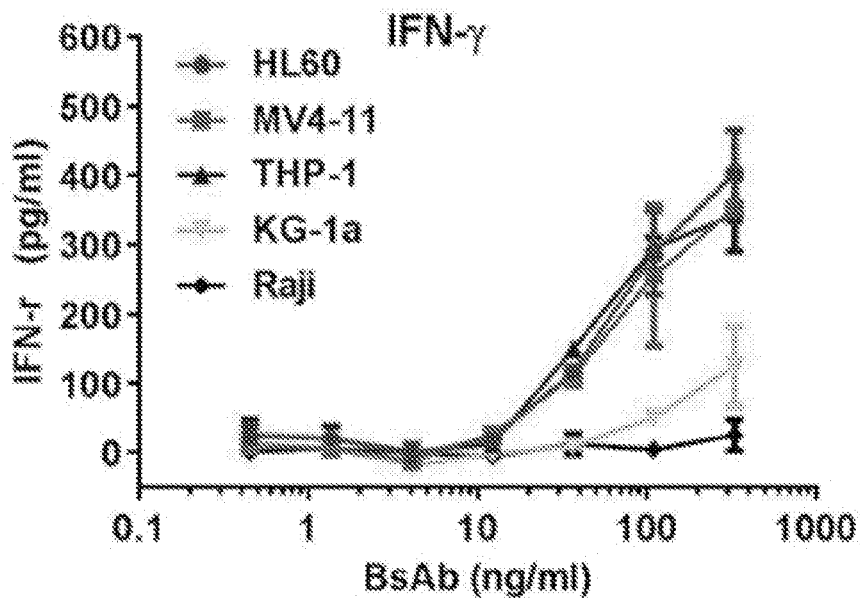
Figure 4F:
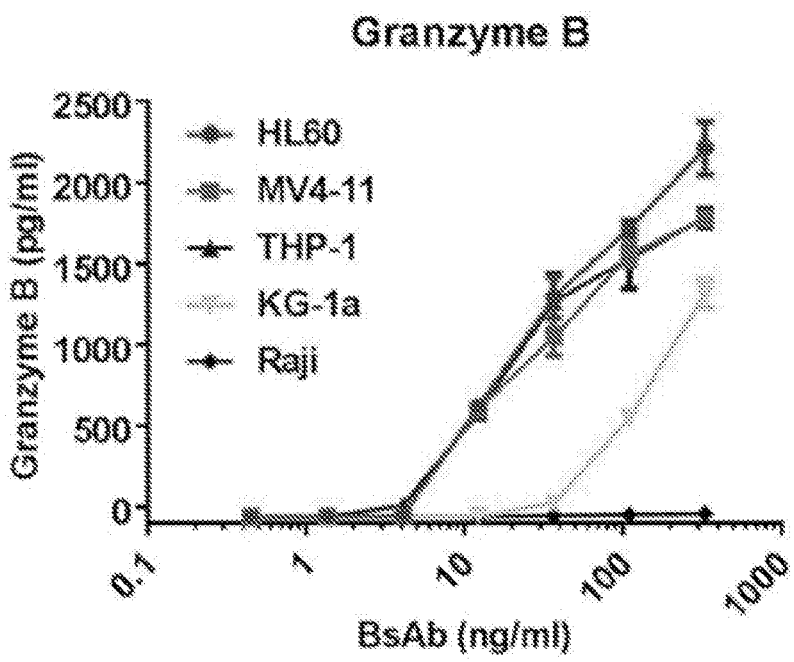
Figure 4G:
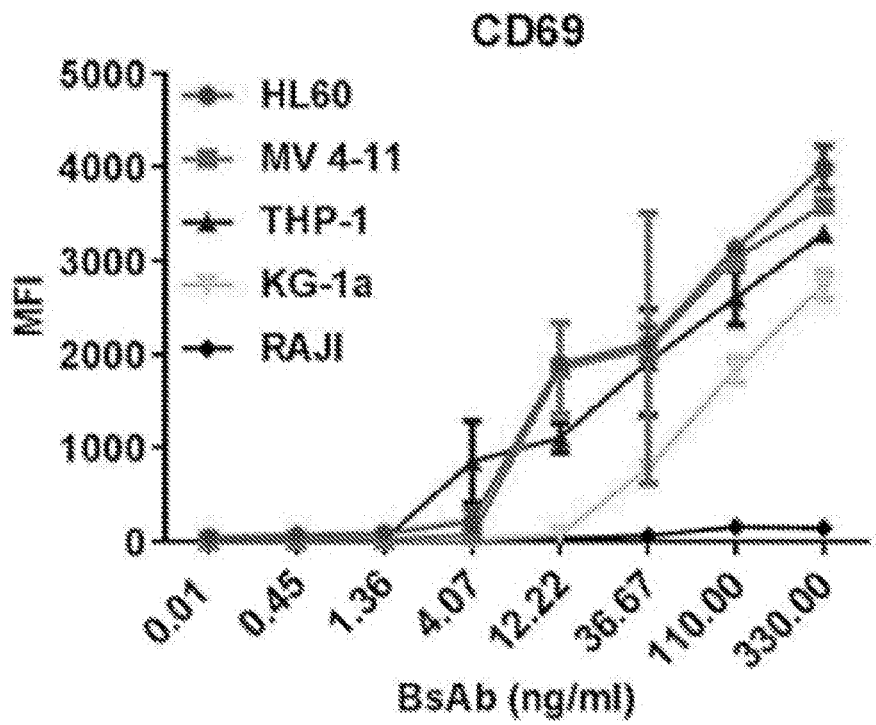
Figure 4H:
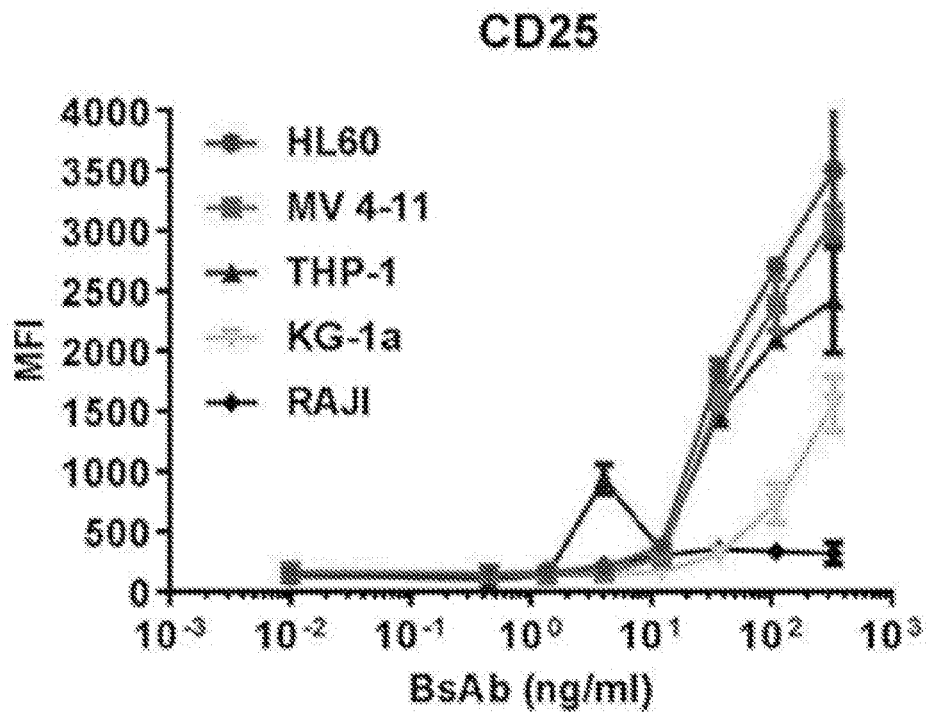
Figure 4I:
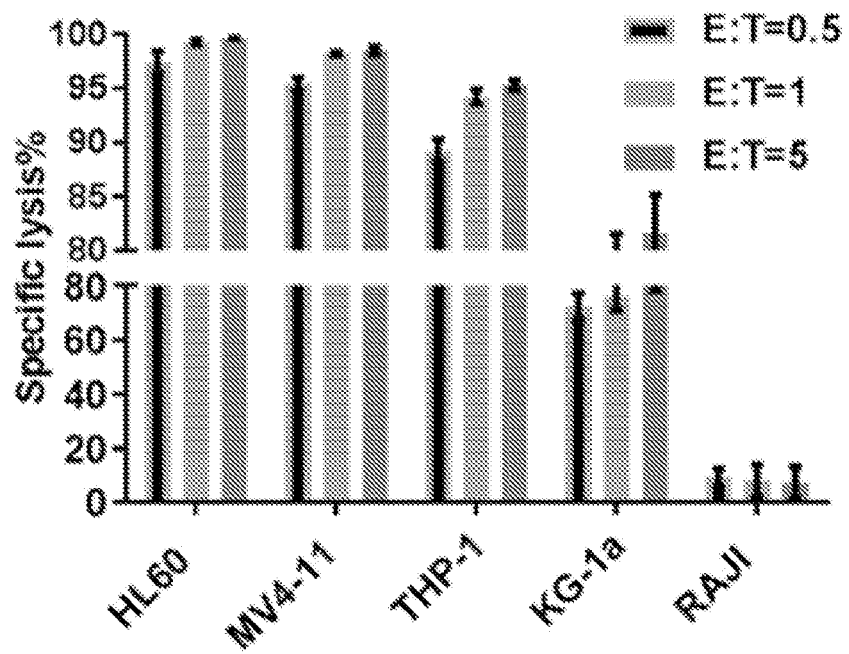
Figure 5A:
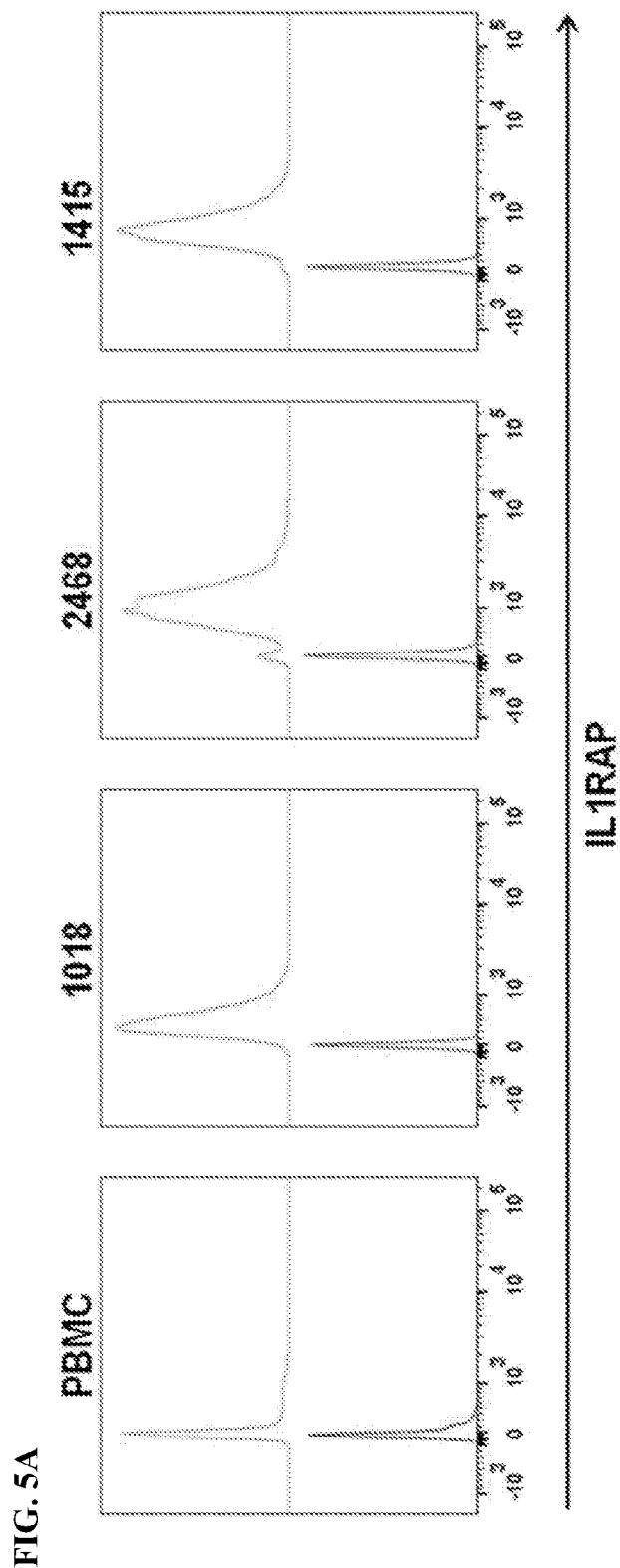
FIGS. 5A-5D. AML patient samples show high level IL1RAP expression.
Figure 5B:
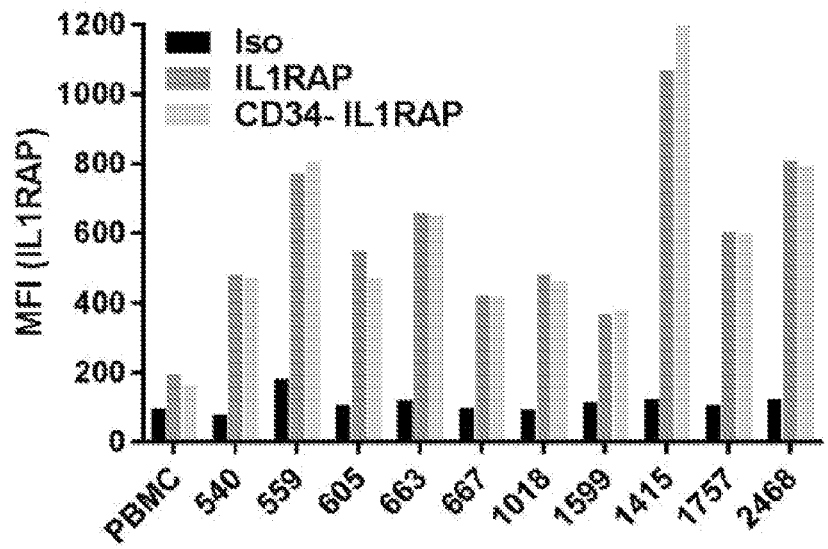
Figure 5C:
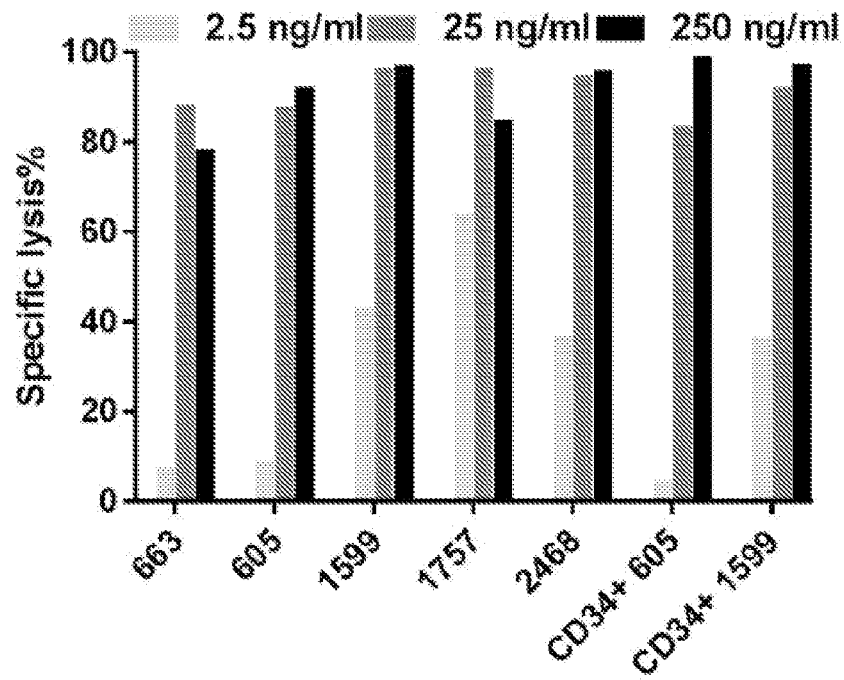
Figure 5D:
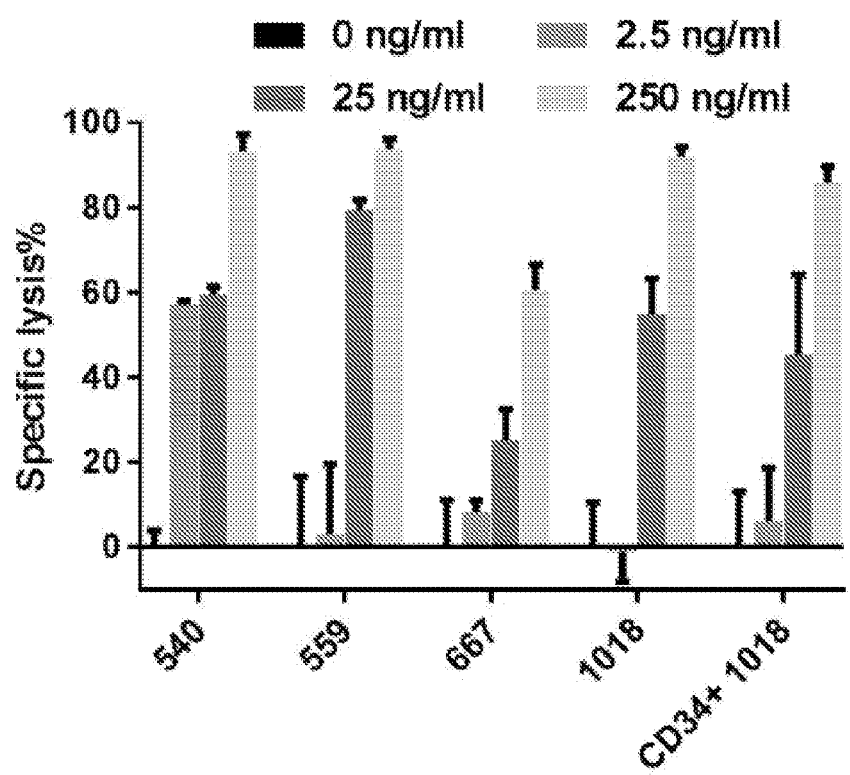

Evaluate correlation between efficacy of anti-IL1RAPxCD3 BsAb-induced T cell killing and IL1RAP expression levels in primary blasts from subsets of AML patients. Applicants showed that IL1RAP is expressed on the surface of AML cell lines (FIGS. 4A-4B) and primary patient blasts (FIGS. 5A-5B), and that Applicants' anti-IL1RAPxCD3 BsAb induces T cell activation and cytotoxicity in AML cell lines (FIGS. 4C-4I) and in AML patient samples (FIGS. 5C-5D), with killing efficiency related to IL1RAP levels on the surface of target cells. To obtain efficacy data based on different cytogenetic and molecular subsets of AML patients, Applicants propose to perform T cell Dependent Cellular Cytotoxicity (TDCC) assays with anti-IL1RAPxCD3 BsAb on 30 additional patient samples representative of the three ELN 2017 cytogenetic/molecular risk groups (favorable, intermediate and adverse) [3]. Unsorted mononuclear cells (MNC) and sorted CD34$^+$CD38$^+$ committed progenitors and CD34$^+$CD38$^-$ primitive progenitors from these 30 AML patient samples will be evaluated for IL1RAP expression by flow cytometry before exposing to anti-IL1RAPxCD3 BsAb and T cells. Since T cells may lose specific T cell markers in culture, Applicants will label AML cells with CFSE before co-culturing them with T cells to separate both cell types. Based on preliminary data, Applicants will use an effector T cell to target AML cell (E:T) ratio of 5:1 for long-term killing assays. Ab in three-fold serial dilutions starting at 330 ng/ml will be tested, in triplicate. Applicants will record counts of living target cells (DAPI$^-$CSFE$^+$) and T cells, and calculate the lysis rate: % Specific lysis=(Target cells$^{+T\ cells}$−Targetcells$^{+BsAb+T\ cells}$)]/Target cells$^{+T\ cells}$)×100%. EC$_{50}$ of BsAb for 30 AML samples will be calculated by Graphpad prism. EC$_{50}$ and IL1RAP expression levels will be correlated. Enrichment of IL1RAP in specific subsets of AML patients and efficacy of the BsAb in these subsets may re-direct efforts to develop this novel drug to target specific cytogenetic/molecular AML subsets and provide insight into employing IL1RAP as a predictive biomarker for response to BsAb.

Figure 6A:
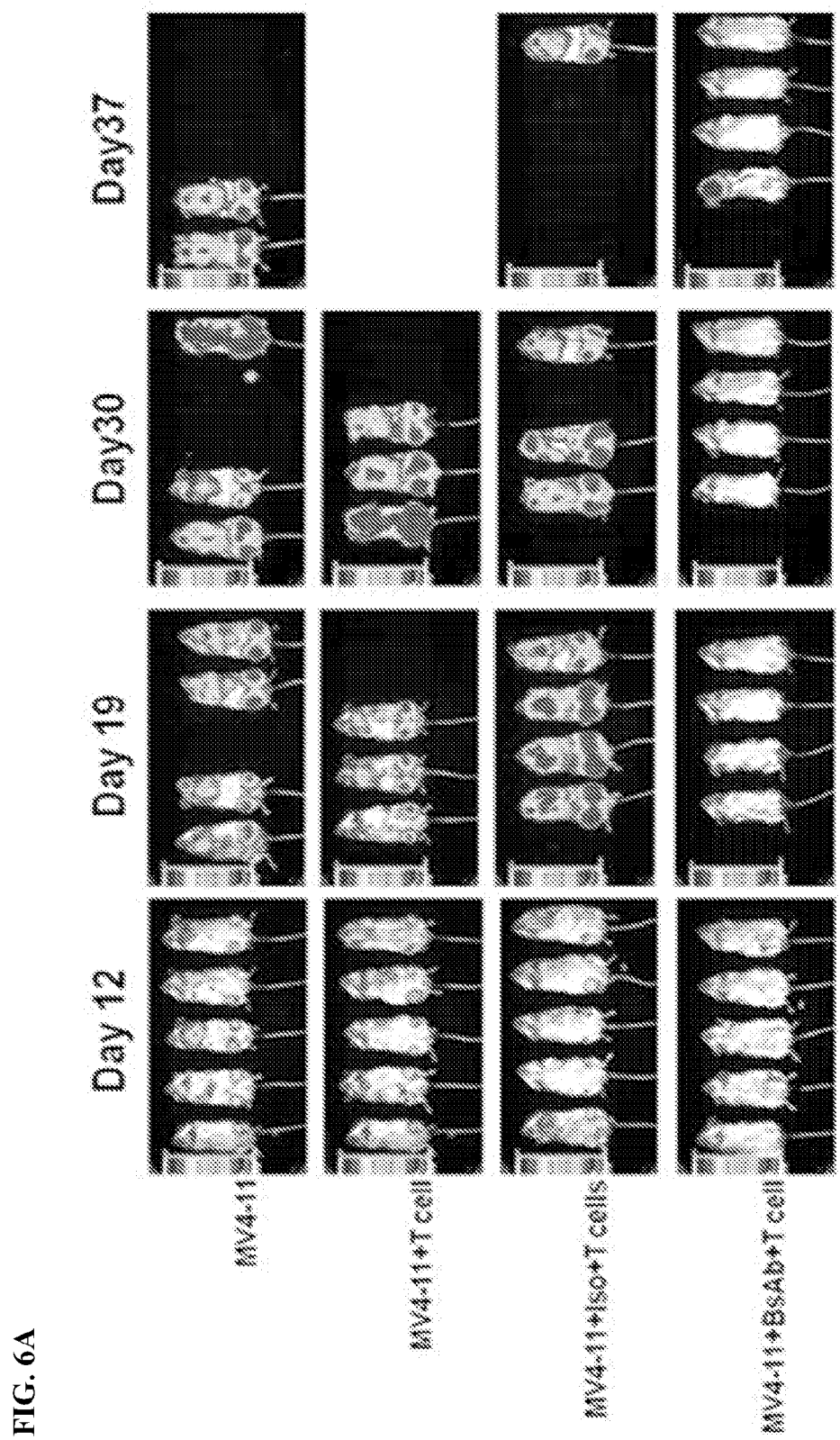
FIGS. 6A-6B. Anti-CD3XIL1RAP effectively treats MV4-11 AML in NSG mice.
Figure 6B:
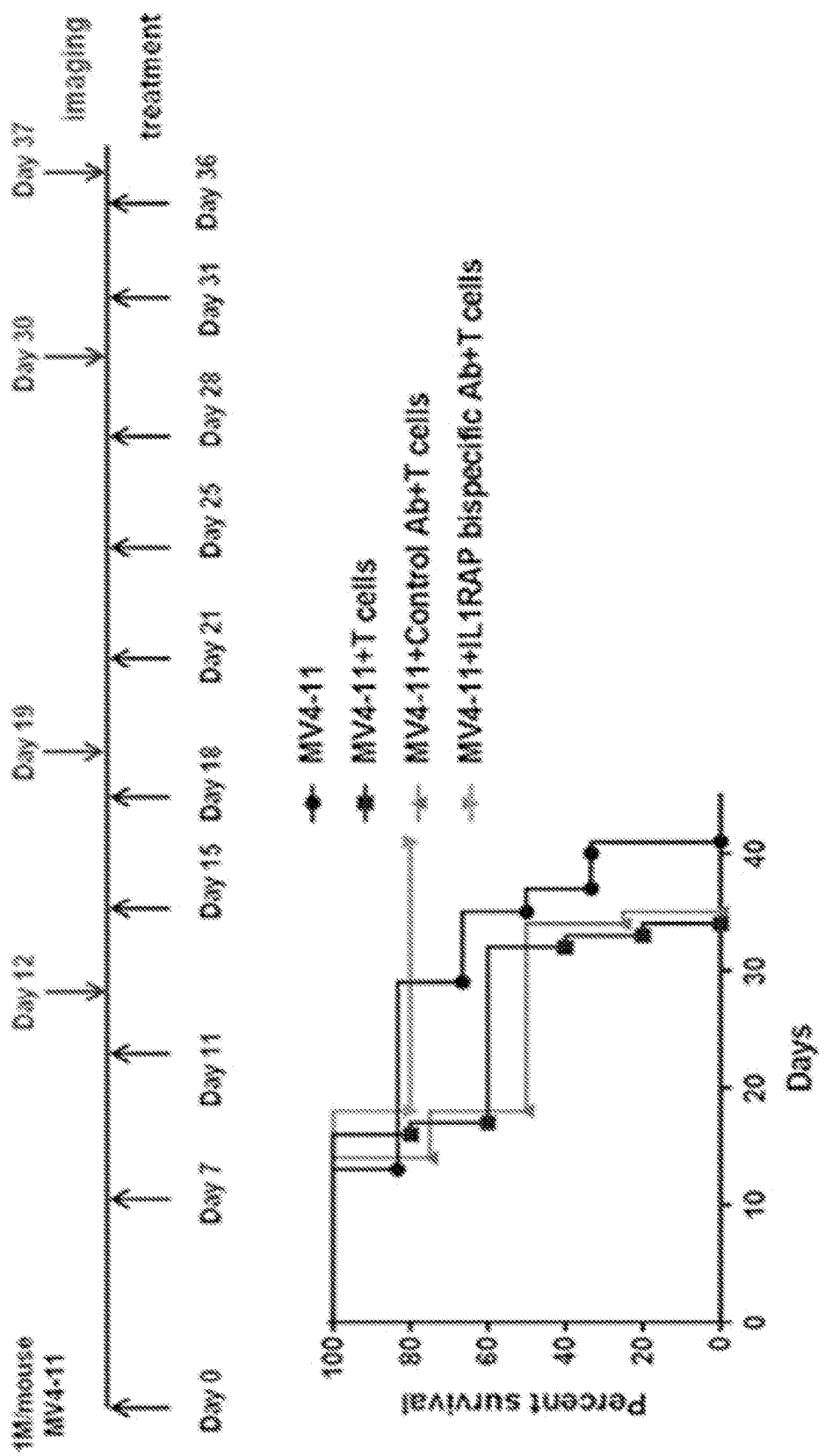

Optimize dose and schedule of administration of anti-IL1RAPXCD3 BsAb and T cells to target AML LSC in vivo. Applicants showed that anti-IL1RAPXCD3 BsAb combined with human T cells effectively eliminate leukemia burden in immunodeficient (NSG) mice transplanted with firefly luciferase-expressing human AML cell line MV4-11 (MV4-11Luci) cells (FIGS. 6A-6B). Applicants propose to conduct pharmacokinetics (PK) and pharmacodynamics (PD) studies and PK-PD modeling to allow optimization of Ab dose/schedule. NSG mice will be treated at 3 log-dose levels (1 mg/kg, 3 mg/kg, 10 mg/kg) of BsAb. Blood will be collected at 1, 2, 4, 8, 24, 48, 72, 96, 120, and 148 hours (n=6 per time points×10 time points×3 doses=180 mice). Based on extensive experience conducting preclinical mouse PK studies, 5-7 mice per time point provide adequate assessment of variability and characterization of PK and PD across the evaluated 1 log-fold dose range. BsAb serum concentration will be determined using the TDCC assay and calculated based on a standard curve obtained by serial dilution of purified BsAb. The optimal dose/schedule of administration will be determined based on BsAb blood half-life. Next, Applicants will transplant NSG mice with 1×10$^6$ MV4-11$^{Luci}$ cells and treat the mice with the optimized dose/schedule of BsAb and 3 doses (i.e., 1×10$^6$, 3×10$^6$ or 5×10$^6$) of T cells at day 7 post-transplant. In vivo imaging will be taken weekly to monitor tumor burden. Calculated total bioluminescence intensity levels in each mouse will represent the main PD endpoint. Relationships between PK and PD data will be initially evaluated using standard linear correlation and linear regression, and a PK-PD model will be built and used to simulate plasma concentration-time profiles and achievement of the correspondent PD endpoint to guide future in vivo experiments. Upon successful computer simulation of the model, Applicants will attain one or more BsAb dose/schedule regimens predicted to maximally decrease of bioluminescence. Applicants will select a regimen for in vivo validation based on the following criteria: a.) lack of toxicity, b.) achievement of maximal bioluminescence change, c.) requirement for less frequent dosing, and d.) lower cost. Validation will be performed by transplanting AML blasts from three patients into NSG mice (16 mice/group×6 groups×2 samples=192 mice) and evaluating in vivo anti-leukemic efficacy of anti-IL1RAPxCD3 BsAb and human T cells at doses predicted by Applicants' PK/PD models. A set of mice will be followed for survival while another set will be euthanized and BM and spleen MNC utilized in secondary transplantation experiments to determine the treatment impact on the residual LSC burden.

Development of IL1RAP CAR-T cells to eradicate human AML LSC and to determine their clinical applicability. T cells redirected to specific antigen targets with engineered chimeric antigen receptors (CAR) are now a powerful therapeutic approach in hematologic malignancies [12, 13]. To enhance reactivity, T cells are genetically modified using engineered receptor constructs that allow for specific targeting of tumor cell surface antigens otherwise not (or less) immunogenic in unmodified T cells. Applicants propose to pursue production and testing of IL1RAP CAR-T cells. Of note, tumor-targeting T cells must persist for a sufficient period of time in vivo for successful tumor elimination; however, mature CAR-T cells rapidly differentiate into short-lived effector cells, which limit their anti-tumor activity in vivo [6, 14, 15]. Thus, Applicants will test both mature T cells and T cell precursors generated from cord blood CD34+ cells to produce IL1RAP CAR-T cells.

Development of IL1RAP CAR-T cells. Applicants have developed lentiviral vectors encoding IL1RAP CAR [17] (FIG. 7A). Jurkat cells transduced with IL1RAP CAR lentivirus showed cell activation compared to control cells (FIG. 7B), thereby confirming effect of IL1RAP CAR construct. Applicants propose to purify T cells from peripheral blood mononuclear cells (PBMC) of healthy donors stimulated with OKT3/CD28 beads and interleukin-2 (IL-2) at 50 IU/ml and transduce them with IL1RAP CAR lentivirus as described [17]. Applicants will also generate CAR-T cell precursors as follows. Cord blood CD34+ cells will be transduced with lentiviral vectors encoding IL1RAP CAR and cultured with immobilized Notch ligand Delta-like 4 (DL4) to promote T cell differentiation. IL1RAP CAR expression in T cells will be confirmed by detecting IL1RAP-scFv via flow cytometry.

Efficacy evaluation of IL1RAP CAR-T cells. After obtaining mature and precursor IL1RAP CAR-T cells, Applicants will test their activity. First, Applicants will incubate IL1RAP CAR-T cells with AML cell lines (HL60, MV4-11, THP-1, KG-1a) and Raji cells (negative control). CD107a, IFN-γ and TNF-α levels will be monitored 6 hours later by flow cytometry as an indicator of T cell activation. Killing efficiency of target AML cells will be determined by a 4-hour $^{51}$Cr release assay. Next, IL1RAP CAR-T cells will be incubated with primary human AML cells, and T cell activation and AML cell killing will be evaluated. For in vivo killing efficacy, MV4-11$^{Luci}$ cells ($1 \times 10^6$/per mouse) will be transplanted into NSG mice, and 7 days later, mice will receive single, double (days 1 and 14), or triple (days 1, 14, 28) injections of 3 doses (i.e., $1 \times 10^6$, $3 \times 10^6$ or $5 \times 10^6$) of IL1RAP CAR-T cells. In vivo imaging will occur weekly to monitor tumor burden until all control mice die. As described, experiments with BsAb PK-PD modeling will be performed based on blood concentration of IL1RAP CAR-T cells overtime and changes in bioluminescence as leukemia burden to determine the optimal dose and frequency of IL1RAP CAR-T cells administration. Applicants will then perform similar experiments using AML patient samples and conduct in vivo efficacy, T cell persistence, and memory T cell formation and challenging studies. Serial transplant experiments, as described above for the BsAb study, will also be performed to ensure LSC elimination.

Enhancement of anti-leukemic activity of IL1RAP-based immunotherapeutics (i.e., anti-IL1RAPxCD3 BsAb or IL1RAP CAR-T cells) using immunocheckpoint inhibitors. Despite encouraging results in preclinical models and in patients, activation of immune-suppressive pathways can antagonize adoptive T-cell therapy [18]. The programmed death-1 (PD-1) pathway has emerged as a promising target for cancer therapy. PD-1 binds to ligands PD-L1 (the predominant immunosuppression mediator upregulated on many tumor types) and PD-L2 expressed on macrophages and dendritic cells [19] [20, 21]. Recent trials using a human-derived IgG4 PD-1 monoclonal Ab (mAb; BMS-936558) show that the Ab inhibits the PD1 immunocheckpoint and restores tumor cell immunogenicity, resulting in durable clinical responses in patients with advanced malignancies [19, 21-24]. Herein we hypothesize that PD-1 inhibitors could enhance adoptive T cell function when used in combination with anti-IL1RAPxCD3 BsAb or IL1RAP CAR-T cells.

Determine the anti-leukemic activity of PD-1 blocking in AML cell lines and AML patient samples. T cell stimulation reportedly enhances PD-L1 (B7-H1) expression on AML cell lines, and IFN-γ treatment significantly enhances PD-L1 expression in AML patient samples [25]. Enhanced PD-L1 expression induced by IFN-γ or TLR ligands, either as an immune response to leukemia cells or released by infectious microorganisms, may protect leukemic cells against T cells. To determine whether CAR or BsAb-induced T cell stimulation increases PD-1 expression, Applicants will employ two ways to evaluate the effect of blocking PD-1 pathway on augmenting the therapeutic efficacy of BsAb+T cells or IL1RAP CAR-T cells treatment. T cells will be co-cultured with MV4-11 AML cells (at E: T ratios of 1:1, 1:5, and 1:10) treated with and without IFN-γ to up-regulate PD-1 ligands, with and without PD-1 blocking antibody (pembrolizumab or nivolumab). The effect of PD-1 blockade on T cell cytolytic activity will be determined based on the lysis rate. Effector cytokine secretion (IL-2, IFN-γ, and TNF-alpha) will be determined by ELISA assay. PD-1 blockade will also be assessed in NSG mice engrafted with MV4-11$^{Luci}$ and treated with CAR-T, with or without PD-1 blocking antibody. Leukemia burden will be determined by in vivo imaging and blood CAR-T cells measured by flow cytometry.

Determine the anti-leukemic activity of BsAb+T cells or IL1RAP CAR-T cells in combination with PD-1 inhibitors. If PD-1/PD-L1 blockade enhances AML cell killing, Applicants will evaluate the effect of BsAb+T cells or IL1RAP CAR-T cells combined with PD-1 blocking in vivo. Applicants will treat NSG mice transplanted with MV4-11$^{Luci}$ or human AML patient samples with anti-IL1RAPXCD3 BsAb and human T cells, or IL1RAP CAR-T cells, in combination with pembrolizumab or nivolumab or isotype control antibodies (The basic protocol is described above). Tumor burden in PB, BM and spleen and survival will be determined, and a $2^{nd}$ transplantation will be performed to monitor LSC eradication.

Statistical Considerations. Based on previous experience, to attain at least 90% power to detect differences in survival, 11 mice per group are required using a one-sided test at α=0.05. Differences between Kaplan-Meier survival curves will be assessed by the log-rank test. Descriptive and graphical statistics will be used to characterize the effect of BsAb+T cells and IL1RAP CAR-T cells in other in vitro and PD studies; formal comparisons will be done using t-tests and/or Mann-Whitney U tests. Similar methods will be used to analyze functional assay data.

REFERENCES

1. Khwaja, A., et al., *Acute myeloid leukaemia*. Nat Rev Dis Primers, 2016. 2: p. 16010.
2. Cancer Genome Atlas Research, N., et al., *Genomic and epigenomic landscapes of adult de novo acute myeloid leukemia*. N Engl J Med, 2013. 368(22): p. 2059-74.

3. Dohner, H., et al., *Diagnosis and management of AML in adults:* 2017 *ELN recommendations from an international expert panel.* Blood, 2017. 129(4): p. 424-447.
4. Gyurkocza, B., A. Rezvani, and R. F. Storb, *Allogeneic hematopoietic cell transplantation: the state of the art.* Expert Rev Hematol, 2010. 3(3): p. 285-99.
5. Ringden, O. and K. Le Blanc, *Allogeneic hematopoietic stem cell transplantation: state of the art and new perspectives.* APMIS, 2005. 113(11-12): p. 813-30.
6. Kenderian, S. S., et al., *Chimeric antigen receptor T-cell therapy to target hematologic malignancies.* Cancer Res, 2014. 74(22): p. 6383-9.
7. Huehls, A M., T. A. Coupet, and C. L. Sentman, *Bispecific T-cell engagers for cancer immunotherapy.* Immunol Cell Biol, 2015. 93(3): p. 290-6.
8. Zhang, B., et al., *Inhibition of interleukin-1 signaling enhances elimination of tyrosine kinase inhibitor-treated CML stem cells.* Blood, 2016. 128(23): p. 2671-2682.
9. Barreyro, L., et al., *Overexpression of IL-1 receptor accessory protein in stem and progenitor cells and outcome correlation in AML and MDS.* Blood, 2012. 120(6): p. 1290-8.
10. Wu, J., et al., *Blinatumomab: a bispecific T cell engager (BiTE) antibody against CD19/CD3 for refractory acute lymphoid leukemia.* J Hematol Oncol, 2015. 8: p. 104.
11. Walter, R. B., *Biting back: BiTE antibodies as a promising therapy for acute myeloid leukemia.* Expert Rev Hematol, 2014. 7(3): p. 317-9.
12. Grupp, S. A., et al., *Chimeric antigen receptor-modified T cells for acute lymphoid leukemia.* N Engl J Med, 2013. 368(16): p. 1509-18.
13. Maus, M. V., et al., *Antibody-modified T cells: CARS take the front seat for hematologic malignancies.* Blood, 2014. 123(17): p. 2625-35.
14. Dolnikov, A., et al., *Antileukemic potency of CD19-specific T cells against chemoresistant pediatric acute lymphoblastic leukemia.* Exp Hematol, 2015. 43(12): p. 1001-1014 e5.
15. Gill, S. and C. H. June, *Going viral: chimeric antigen receptor T-cell therapy for hematological malignancies.* Immunol Rev, 2015. 263(1): p. 68-89.
16. Zakrzewski, J. L., et al., *Tumor immunotherapy across MHC barriers using allogeneic T-cell precursors.* Nat Biotechnol, 2008. 26(4): p. 453-61.
17. Mardiros, A., et al., *T cells expressing CD123-specific chimeric antigen receptors exhibit specific cytolytic effector functions and antitumor effects against human acute myeloid leukemia.* Blood, 2013. 122(18): p. 3138-48.
18. Pardoll, D. M., *The blockade of immune checkpoints in cancer immunotherapy.* Nat Rev Cancer, 2012. 12(4): p. 252-64.
19. Ascierto, P. A., et al., *Clinical experiences with anti-CD137 and anti PD1 therapeutic antibodies.* Semin Oncol, 2010. 37(5): p. 508-16.
20. Blank, C., T. F. Gajewski, and A. Mackensen, *Interaction of PD-L1 on tumor cells with PD-1 on tumor-specific T cells as a mechanism of immune evasion: implications for tumor immunotherapy.* Cancer Immunol Immunother, 2005. 54(4): p. 307-14.
21. Keir, M. E., et al., *PD-1 and its ligands in tolerance and immunity.* Annu Rev Immunol, 2008. 26: p. 677-704.
22. Berger, R., et al., *Phase I safety and pharmacokinetic study of CT-011, a humanized antibody interacting with PD-1, in patients with advanced hematologic malignancies.* Clin Cancer Res, 2008. 14(10): p. 3044-51.
23. Topalian, S. L., et al., *Safety, activity, and immune correlates of anti-PD-*1 *antibody in cancer.* N Engl J Med, 2012. 366(26): p. 2443-54.
24. Brahmer, J. R., et al., *Safety and activity of anti-PD-L*1 *antibody in patients with advanced cancer.* N Engl J Med, 2012. 366(26): p. 2455-65.
25. Berthon, C., et al., In acute myeloid leukemia, B7-H1 (PD-L1) protection of blasts from cytotoxic T cells is induced by TLR ligands and interferon-gamma and can be reversed using MEK inhibitors. Cancer Immunol Immunother, 2010. 59(12): p. 1839-49.

Informal Sequence Listing

```
SEQ ID NO: 1 (CDR L1):
QSLLHSNGYKY

SEQ ID NO: 2 (CDR L2):
LGS

SEQ ID NO: 3 (CDR L3):
MQALQTPLT

SEQ ID NO: 4 (CDR H1):
GYSFSSHW

SEQ ID NO: 5 (CDR H2):
IYPGDSDT

SEQ ID NO: 6 (CDR H3):
ARGELPGEAYYFDN

SEQ ID NO: 7 (Light chain variable region):
EIVMTQSPLSLPVTPGEPASISCRSSQSLLHSNGYKYLDWYLQKPGQSPQ

LLIYLGSNRASGVPDRFSGSGSGTDFTLKISRVEAEDVGVYYCMQALQTP

LTFGGGTKVEIK

SEQ ID NO: 8 (Heavy chain variable region):
QVQLVQSGAEVKKPGESLKISCKGSGYSFSSHWIGWVRQMPGKGLEWMGI

IYPGDSDTRYSPSFQGQVTISADKSISTAYLQWSSLKASDTAMYYCARGE

LPGEAYYFDNWGQGTLVTVSS

SEQ ID NO: 9 (FR L1):
EIVMTQSPLSLPVTPGEPASISCRSS

SEQ ID NO: 10 (FR L2):
LDWYLQKPGQSPQLLIY

SEQ ID NO: 11 (FR L3):
NRASGVPDRFSGSGSGTDFTLKISRVEAEDVGVYYC

SEQ ID NO: 12 (FR L4):
FGGGTKVEIK

SEQ ID NO: 13 (FR H1):
QVQLVQSGAEVKKPGESLKISCKGS

SEQ ID NO: 14 (FR H2):
IGWVRQMPGKGLEWMGI

SEQ ID NO: 15 (FR H3):
RYSPSFQGQVTISADKSISTAYLQWSSLKASDTAMYYC

SEQ ID NO: 16 (FR H4):
WGQGTLVTVSS

SEQ ID NO: 17 (Amino acid sequence of 1D5-scFv):
QVQLVQSGAEVKKPGESLKISCKGSGYSFSSHWIGWVRQMPGKGLEWMGI

IYPGDSDTRYSPSFQGQVTISADKSISTAYLQWSSLKASDTAMYYCARGE

LPGEAYYFDNWGQGTLVTVSSGGGGSGGGGSGGGGSEIVMTQSPLSLPVT
```

-continued

PGEPASISCRSSQSLLHSNGYKYLDWYLQKPGQSPQLLIYLGSNRASGVP

DRFSGSGSGTDFTLKISRVEAEDVGVYYCMQALQTPLTFGGGTKVEIK

SEQ ID NO: 18 (Nucleotide sequence of 1D5 scFv):
CAGGTGCAGCTGGTGCAGAGCGGCGCCGAAGTGAAGAAGCCCGGCGAGAG

CCTGAAGATCAGCTGCAAGGGCAGCGGCTACAGCTTCAGCAGCCACTGGA

TCGGCTGGGTCAGGCAGATGCCCGGCAAAGGCCTGGAGTGGATGGGCATC

ATCTATCCCGGCGACAGCGACACCAGGTACTCCCCCAGCTTCCAGGGCCA

GGTGACCATCTCCGCCGACAAGAGCATTAGCACCGCCTACCTGCAGTGGA

GCAGCCTCAAAGCCAGCGACACCGCCATGTACTACTGCGCCAGAGGCGAA

CTGCCCGGAGAGGCCTACTACTTCGATAACTGGGGCCAGGGCACCCTGGT

GACAGTGAGCAGCGGAGGAGGCGGCAGCGGCGGCGGCGGATCCGGAGGAG

GCGGCTCCGAGATCGTGATGACCCAGAGCCCTCTGAGCCTGCCCGTGACA

CCTGGCGAACCTGCCAGCATCAGCTGCAGAAGCAGCCAGAGCCTGCTCCA

CTCCAACGGCTACAAATACCTGGACTGGTATCTCCAGAAGCCTGGCCAGA

GCCCCCAGCTGCTCATCTACCTGGGCAGCAATAGGGCCAGCGGAGTGCCC

GACAGGTTTAGCGGCTCCGGAAGCGGCACCGATTTCACCCTGAAAATCAG

CAGAGTGGAGGCCGAGGACGTGGGCGTGTACTACTGCATGCAGGCTCTGC

AGACACCCCTGACCTTCGGCGGAGGCACCAAGGTGGAGATCAAG

SEQ ID NO: 19 (Linker region):
GGGGSGGGGSGGGGS

SEQ ID NO: 20 (1D5-scFv-Hole-FC-LA sequence):
QVQLVQSGAEVKKPGESLKISCKGSGYSFSSHWIGWVRQMPGKGLEWMGI

IYPGDSDTRYSPSFQGQVTISADKSISTAYLQWSSLKASDTAMYYCARGE

LPGEAYYFDNWGQGTLVTVSSGGGGSGGGGSGGGGSEIVMTQSPLSLPVT

PGEPASISCRSSQSLLHSNGYKYLDWYLQKPGQSPQLLIYLGSNRASGVP

DRFSGSGSGTDFTLKISRVEAEDVGVYYCMQALQTPLTFGGGTKVEIKCA

PKSCDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVSLS

CAVKGFYPSDIAVEWESNGQPENNYKTTPPVLDSDGSFFLVSKLTVDKSR

WQQGNVFSCSVMHEALHNHYTQKSLSLSPGK

SEQ ID NO: 21 (Anti-CD3-scFv-Knob-FC-LA sequence):
EVQLVESGGGLVQPGGSLKLSCAASGFTFNKYAMNWVRQAPGKGLEWVAR

IRSKYNNYATYYADSVKDRFTISRDDSKNTAYLQMNNLKTEDTAVYYCVR

HGNFGNSYISYWAYWGQGTLVTVSSGGGGSGGGGSGGGGSQTVVTQEPSL

TVSPGGTVTLTCGSSTGAVTSGNYPNWVQQKPGQAPRGLIGGTKFLAPGT

PARFSGSLLGGKAALTLSGVQPEDEAEYYCVLWYSNRWVFGGGTKLTVLC

APKSCDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

WCLVKGFYPSDIAVEWESNGQPENNYKTTPPVLDSDGSFFLYSKLTVDKS

RWQQGNVFSCSVMHEALHNHYTQKSLSLSPGK

-continued

SEQ ID NO: 90 (1D5-scFv-CAR amino acid sequence)
MLLLVTSLLLCELPHPAFLLIPQVQLVQSGAEVKKPGESLKISCKGSGYS

FSSHWIGWVRQMPGKGLEWMGIIYPGDSDTRYSPSFQGQVTISADKSIST

AYLQWSSLKASDTAMYYCARGELPGEAYYFDNWGQGTLVTVSSGGGGSGG

GGSGGGGSEIVMTQSPLSLPVTPGEPASISCRSSQSLLHSNGYKYLDWYL

QKPGQSPQLLIYLGSNRASGVPDRFSGSGSGTDFTLKISRVEAEDVGVYY

CMQALQTPLTFGGGTKVEIKVAAAAFVPVFLPAKPTTTPAPRPPTPAPTI

ASQPLSLRPEACRPAAGGAVHTRGLDFACDIYIWAPLAGTCGVLLLSLVI

TLYCNHRNRFSVVKRGRKKLLYIFKQPFMRPVQTTQEEDGCSCRFPEEEE

GGCELRVKFSRSADAPAYQQGQNQLYNELNLGRREEYDVLDKRRGRDPEM

GGKPRRKNPQEGLYNELQKDKMAEAYSEIGMKGERRRGKGHDGLYQGLST

ATKDTYDALHMQALPPR

P Embodiments

P Embodiment 1. An anti-interleukin-1 receptor accessory protein (IL1RAP) antibody comprising a light chain variable domain and a heavy chain variable domain,
wherein said light chain variable domain comprises:
a CDR L1 as set forth in SEQ ID NO:1, a CDR L2 as set forth in SEQ ID NO:2 and a CDR L3 as set forth in SEQ ID NO:3; and
wherein said heavy chain variable domain comprises:
a CDR H1 as set forth in SEQ ID NO:4, a CDR H2 as set forth in SEQ ID NO:5, and a CDR H3 as set forth in SEQ ID NO:6.

P Embodiment 2. The antibody of P embodiment 1, wherein said light chain variable domain comprises the sequence of SEQ ID NO:7.

P Embodiment 3. The antibody of P embodiment 1 or 2, wherein said heavy chain variable domain comprises the sequence of SEQ ID NO:8.

P Embodiment 4. The antibody of one of P embodiments 1-3, wherein said light chain variable domain comprises a FR L1 as set forth in SEQ ID NO:9, a FR L2 as set forth in SEQ ID NO:10, FR L3 as set forth in SEQ ID NO:11 and a FR L4 as set forth in SEQ ID NO:12.

P Embodiment 5. The antibody of one of P embodiments 1-4, wherein said heavy chain variable domain comprises a FR H1 as set forth in SEQ ID NO:13, a FR H2 as set forth in SEQ ID NO:14, FR H3 as set forth in SEQ ID NO:15 and a FR H4 as set forth in SEQ ID NO:16.

P Embodiment 6. The antibody of one of P embodiments 1-5, wherein said antibody is an IgG.

P Embodiment 7. The antibody of one of P embodiments 1-6, wherein said antibody is an IgG1.

P Embodiment 8. The antibody of one of P embodiments 1-5, wherein said antibody is a Fab' fragment.

P Embodiment 9. The antibody of one of P embodiments 1-5, wherein said antibody is a single chain antibody (scFv).

P Embodiment 10. The antibody of one of P embodiments 1-5, wherein said light chain variable domain and said heavy chain variable domain form part of a scFv.

P Embodiment 11. The antibody of P embodiment 9 or 10, wherein said scFv comprises the sequence of SEQ ID NO:17.

P Embodiment 12. The antibody of one of P embodiments 1-11, wherein said antibody is capable of binding IL1RAP with an equilibrium dissociation constant ($K_D$) of about 21 nM.

P Embodiment 13. The antibody of one of P embodiments 1-11, wherein said antibody has an $EC_{50}$ of about 4.9 ng/ml.

P Embodiment 14. The antibody of one of P embodiments 1-13, wherein said antibody is bound to an IL1RAP.

P Embodiment 15. The antibody of P embodiment 14, wherein said IL1RAP is a human IL1RAP.

P Embodiment 16. The antibody of P embodiment 14 or 15, wherein said IL1RAP forms part of a cell.

P Embodiment 17. The antibody of P embodiment 16, wherein said IL1RAP is expressed on the surface of said cell.

P Embodiment 18. The antibody of P embodiment 16 or 17, wherein said cell is a cancer cell.

P Embodiment 19. The antibody of P embodiment 18, wherein said cancer cell is a leukemia stem cell (LSC).

P Embodiment 20. The antibody of P embodiment 18, wherein said cancer cell is an acute myeloid leukemia (AML) cell.

P Embodiment 21. An isolated nucleic acid encoding an antibody of one of P embodiments 1-21.

P Embodiment 22. A pharmaceutical composition comprising a therapeutically effective amount of an antibody of one of P embodiments 1-21 and a pharmaceutically acceptable excipient.

P Embodiment 23. A method of treating cancer in a subject in need thereof, said method comprising administering to a subject a therapeutically effective amount of an antibody of one of P embodiments 1-21, thereby treating cancer in said subject.

P Embodiment 24. A recombinant protein comprising:
(i) an antibody region comprising:
(a) a light chain variable domain comprising a CDR L1 as set forth in SEQ ID NO:1, a CDR L2 as set forth in SEQ ID NO:2 and a CDR L3 as set forth in SEQ ID NO:3; and
(b) a heavy chain variable region domain a CDR H1 as set forth in SEQ ID NO:4, a CDR H2 as set forth in SEQ ID NO:5, and a CDR H3 as set forth in SEQ ID NO:6; and
(ii) a transmembrane domain.

P Embodiment 25. The recombinant protein of P embodiment 24, wherein said light chain variable domain comprises the sequence of SEQ ID NO:7.

P Embodiment 26. The recombinant protein of P embodiment 24 or 25, wherein said heavy chain variable domain comprises the sequence of SEQ ID NO:8.

P Embodiment 27. The recombinant protein of one of P embodiments 24-26, wherein said light chain variable domain comprises a FR L1 as set forth in SEQ ID NO:9, a FR L2 as set forth in SEQ ID NO:10, FR L3 as set forth in SEQ ID NO:11 and a FR L4 as set forth in SEQ ID NO:12.

P Embodiment 28. The recombinant protein of one of P embodiments 24-27, wherein said heavy chain variable domain comprises a FR H1 as set forth in SEQ ID NO:13, a FR H2 as set forth in SEQ ID NO:14, FR H3 as set forth in SEQ ID NO:15 and a FR H4 as set forth in SEQ ID NO:16.

P Embodiment 29. The recombinant protein of one of P embodiments 24-28, wherein said antibody region comprises a single-chain variable fragment (scFv).

P Embodiment 30. The recombinant protein of P embodiment 29, wherein said scFv comprises the sequence of SEQ ID NO:17.

P Embodiment 31. The recombinant protein of one of P embodiments 24-30, wherein said recombinant protein is capable of binding IL1RAP with an equilibrium dissociation constant ($K_D$) of about 21 nM.

P Embodiment 32. The recombinant protein of one of P embodiments 24-31, wherein said recombinant protein has an $EC_{50}$ of about 4.9 ng/ml.

P Embodiment 33. The recombinant protein of one of P embodiments 24-32, wherein said recombinant protein is bound to an IL1RAP.

P Embodiment 34. The recombinant protein of P embodiment 33, wherein said IL1RAP is a human IL1RAP.

P Embodiment 35. The recombinant protein of P embodiment 33 or 34, wherein said IL1RAP forms part of a cell.

P Embodiment 36. The recombinant protein of one of P embodiments 33-35, wherein said IL1RAP is expressed on the surface of said cell.

P Embodiment 37. The recombinant protein of P embodiment 36, wherein said cell is a cancer cell.

P Embodiment 38. The recombinant protein P embodiment 37, wherein said cancer cell is a leukemia stem cell (LSC).

P Embodiment 39. The recombinant protein P embodiment 37, wherein said cancer cell is an acute myeloid leukemia (AML) cell.

P Embodiment 40. The recombinant protein of one of P embodiments 24-39, wherein said antibody region comprises an Fc domain.

P Embodiment 41. The recombinant protein of P embodiment 40, wherein said Fc domain is an IgG4 Fc domain.

P Embodiment 42. The recombinant protein of one of P embodiments 24-41, further comprising an intracellular co-stimulatory signaling domain.

P Embodiment 43. The recombinant protein of P embodiment 42, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

P Embodiment 44. The recombinant protein of one of P embodiments 24-43, further comprising an intracellular T-cell signaling domain.

P Embodiment 45. The recombinant protein of P embodiment 44, wherein said intracellular T-cell signaling domain is a CD3 ζ intracellular T-cell signaling domain.

P Embodiment 46. The recombinant protein of one of P embodiments 24-45, further comprising a self-cleaving peptidyl sequence.

P Embodiment 47. The recombinant protein of P embodiment 46, wherein said self-cleaving peptidyl linker sequence is a T2A sequence or a 2A sequence.

P Embodiment 48. The recombinant protein of one of P embodiments 24-47, further comprising a detectable domain.

P Embodiment 49. The recombinant protein of P embodiment 48, wherein said detectable domain is a truncated EGFR (EGFRt) domain.

P Embodiment 50. The recombinant protein of one of P embodiments 24-49, wherein said recombinant protein forms part of a cell.

P Embodiment 51. The recombinant protein of one of P embodiments 24-49, wherein said recombinant protein forms part of a T cell.

P Embodiment 52. An isolated nucleic acid encoding a recombinant protein of one of P embodiments 24-51.

P Embodiment 53. A pharmaceutical composition comprising a therapeutically effective amount of a recombinant protein of one of P embodiments 24-51 and a pharmaceutically acceptable excipient.

P Embodiment 54. A method of treating cancer in a subject in need thereof, said method comprising administering to a subject a therapeutically effective amount of a recombinant protein of one of P embodiments 24-51, thereby treating cancer in said subject.

P Embodiment 55. A recombinant protein comprising:
(i) a first antibody region capable of binding an effector cell ligand; and
(ii) a second antibody region, comprising:
(a) a light chain variable domain comprising a CDR L1 as set forth in SEQ ID NO:1, a CDR L2 as set forth in SEQ ID NO:2 and a CDR L3 as set forth in SEQ ID NO:3; and
(b) a heavy chain variable region domain a CDR H1 as set forth in SEQ ID NO:4, a CDR H2 as set forth in SEQ ID NO:5, and a CDR H3 as set forth in SEQ ID NO:6.

P Embodiment 56. The recombinant protein of P embodiment 55, wherein said effector cell ligand is a CD3 protein.

P Embodiment 57. The recombinant protein of one of P embodiments 55-56, wherein said light chain variable domain comprises the sequence of SEQ ID NO:7.

P Embodiment 58. The recombinant protein of one of P embodiments 55-57, wherein said heavy chain variable domain comprises the sequence of SEQ ID NO:8.

P Embodiment 59. The recombinant protein of one of P embodiments 55-58, wherein said light chain variable domain comprises a FR L1 as set forth in SEQ ID NO:9, a FR L2 as set forth in SEQ ID NO:10, FR L3 as set forth in SEQ ID NO:11 and a FR L4 as set forth in SEQ ID NO:12.

P Embodiment 60. The recombinant protein of one of P embodiments 55-59, wherein said heavy chain variable domain comprises a FR H1 as set forth in SEQ ID NO:13, a FR H2 as set forth in SEQ ID NO:14, FR H3 as set forth in SEQ ID NO:15 and a FR H4 as set forth in SEQ ID NO:16.

P Embodiment 61. The recombinant protein of one of P embodiments 55-60, wherein said first antibody region is a first Fab' fragment or said second antibody region is a second Fab' fragment.

P Embodiment 62. The recombinant protein of one of P embodiments 55-60, wherein said first antibody region is a single chain variable fragment (scFv) or said second antibody region is a second single chain variable fragment (scFv).

P Embodiment 63. The recombinant protein of one of P embodiments 55-56, wherein said second scFv comprises the sequence of SEQ ID NO:17.

P Embodiment 64. The recombinant protein of one of P embodiments 55-63, wherein said second antibody region is capable of binding IL1RAP with an equilibrium dissociation constant ($K_D$) of about 21 nM.

P Embodiment 65. The recombinant protein of one of P embodiments 55-64, wherein said second antibody region has an $EC_{50}$ of about 4.9 ng/ml.

P Embodiment 66. The recombinant protein of one of P embodiments 55-65, wherein said second antibody region is bound to an IL1RAP.

P Embodiment 67. The recombinant protein of P embodiment 66, wherein said IL1RAP is a human IL1RAP.

P Embodiment 68. The recombinant protein of one of P embodiments 66-67, wherein said IL1RAP forms part of a cell.

P Embodiment 69. The recombinant protein of one of P embodiments 66-68, wherein said IL1RAP is expressed on the surface of said cell.

P Embodiment 70. The recombinant protein of P embodiment 69, wherein said cell is a cancer cell.

P Embodiment 71. The recombinant protein of P embodiment 70, wherein said cancer cell is a leukemia stem cell (LSC).

P Embodiment 72. The recombinant protein of P embodiment 70, wherein said cancer cell is an acute myeloid leukemia (AML) cell.

P Embodiment 73. A pharmaceutical composition comprising a therapeutically effective amount of a recombinant protein of one of P embodiments 55-72 and a pharmaceutically acceptable excipient.

P Embodiment 74. A method of treating cancer in a subject in need thereof, said method comprising administering to a subject a therapeutically effective amount of a recombinant protein of one of P embodiments 55-72, thereby treating cancer in said subject.

P Embodiment 75. The method of one of P embodiments 23, 54 or 74, wherein said cancer is leukemia.

P Embodiment 76. The method of one of P embodiments 23, 54 or 74, wherein said cancer is acute myeloid leukemia.

P Embodiment 77. The method of one of P embodiments 23, 54 or 74, said method further comprising administering to said subject a second therapeutic agent.

P Embodiment 78. A method of inhibiting proliferation of a cell, said method comprising:
(i) contacting a cell with an anti-IL1RAP antibody of one of P embodiments 1-21, a recombinant protein of one of P embodiments 24-51 or a recombinant protein of one of P embodiments 55-72, thereby forming a contacted cell; and
(ii) allowing said anti-IL1RAP antibody of one of P embodiments 1-21, said recombinant protein of one of P embodiments 24-51 or said recombinant protein of one of P embodiments 55-72 to bind an IL1RAP on said contacted cell, thereby inhibiting proliferation of said cell.

P Embodiment 79. The method of P embodiment 78, wherein said cell is a cancer cell.

P Embodiment 80. The method of P embodiment 78 or 79, wherein said cell is a leukemia stem cell (LSC).

---

What is claimed is:

1. An anti-interleukin-1 receptor accessory protein (IL1RAP) antibody comprising a light chain variable domain and a heavy chain variable domain,
wherein said light chain variable domain comprises:
a CDR L1 as set forth in SEQ ID NO:1, a CDR L2 as set forth in SEQ ID NO:2 and a CDR L3 as set forth in SEQ ID NO:3; and
wherein said heavy chain variable domain comprises:
a CDR H1 as set forth in SEQ ID NO:4, a CDR H2 as set forth in SEQ ID NO:5, and a CDR H3 as set forth in SEQ ID NO:6.

2. The anti-IL1RAP antibody of claim 1, wherein said light chain variable domain comprises the sequence of SEQ ID NO:7.

3. The anti-IL1RAP antibody of claim 1, wherein said heavy chain variable domain comprises the sequence of SEQ ID NO:8.

4. The anti-IL1RAP antibody of claim 1, wherein said antibody is capable of binding IL1RAP with an equilibrium dissociation constant ($K_D$) of about 21 nM.

5. An isolated nucleic acid encoding the anti-IL1 RAP antibody of claim 1.

6. A pharmaceutical composition comprising a therapeutically effective amount of the anti-IL1 RAP antibody of claim 1 and a pharmaceutically acceptable excipient.

7. A method of treating cancer that expresses IL1 RAP in a subject in need thereof, said method comprising administering to said subject a therapeutically effective amount of the anti-IL1 RAP antibody of claim 1, thereby treating cancer in said subject.

8. A recombinant protein comprising:
(i) an antibody region comprising:
(a) a light chain variable domain comprising a CDR L1 as set forth in SEQ ID NO:1, a CDR L2 as set forth in SEQ ID NO:2 and a CDR L3 as set forth in SEQ ID NO:3; and
(b) a heavy chain variable domain comprising a CDR H1 as set forth in SEQ ID NO:4, a CDR H2 as set forth in SEQ ID NO:5, and a CDR H3 as set forth in SEQ ID NO:6; and
(ii) a transmembrane domain.

9. The recombinant protein of claim 8, wherein said light chain variable domain comprises the sequence of SEQ ID NO:7.

10. The recombinant protein of claim 8, wherein said heavy chain variable domain comprises the sequence of SEQ ID NO:8.

11. The recombinant protein of claim 8, further comprising an intracellular co-stimulatory signaling domain.

12. The recombinant protein of claim 8, further comprising an intracellular T-cell signaling domain.

13. The recombinant protein of claim 8, wherein said recombinant protein forms part of a T cell.

14. An isolated nucleic acid encoding the recombinant protein of claim 8.

15. A pharmaceutical composition comprising a therapeutically effective amount of the recombinant protein of claim 8 and a pharmaceutically acceptable excipient.

16. A method of treating cancer in a subject in need thereof, said method comprising administering to a subject a therapeutically effective amount of the recombinant protein of claim 8, thereby treating cancer in said subject.

17. A recombinant protein comprising:
(i) a first antibody region capable of binding an effector cell ligand; and
(ii) a second antibody region, comprising:
(a) a light chain variable domain comprising a CDR L1 as set forth in SEQ ID NO:1, a CDR L2 as set forth in SEQ ID NO:2 and a CDR L3 as set forth in SEQ ID NO:3; and
(b) a heavy chain variable domain comprising a CDR H1 as set forth in SEQ ID NO:4, a CDR H2 as set forth in SEQ ID NO:5, and a CDR H3 as set forth in SEQ ID NO:6.

18. The recombinant protein of claim 17, wherein said effector cell ligand is a CD3 protein.

19. The recombinant protein of claim 17, wherein said light chain variable domain comprises the sequence of SEQ ID NO:7.

20. The recombinant protein of claim 17, wherein said heavy chain variable domain comprises the sequence of SEQ ID NO:8.

* * * * *